(12) United States Patent
Shalev et al.

(10) Patent No.: US 7,117,033 B2
(45) Date of Patent: Oct. 3, 2006

(54) STIMULATION FOR ACUTE CONDITIONS

(75) Inventors: Alon Shalev, Ra'anana (IL); Amir Natan, Tel Aviv (IL)

(73) Assignee: Brainsgate, Ltd., Ra'Anana (IL)

( * ) Notice: Subject to any disclaimer, the term of this patent is extended or adjusted under 35 U.S.C. 154(b) by 243 days.

(21) Appl. No.: 10/783,113

(22) Filed: Feb. 20, 2004

(65) Prior Publication Data

US 2004/0220644 A1    Nov. 4, 2004

Related U.S. Application Data

(63) Continuation-in-part of application No. 10/258,714, filed as application No. PCT/IL01/00402 on May 7, 2001.

(60) Provisional application No. 60/506,165, filed on Sep. 26, 2003, provisional application No. 60/203,172, filed on May 8, 2000.

(51) Int. Cl.
*A61N 1/08* (2006.01)
(52) U.S. Cl. .......................................................... 607/2
(58) Field of Classification Search .................... 607/2, 607/45, 46
See application file for complete search history.

(56) References Cited

U.S. PATENT DOCUMENTS

| 4,979,511 A | 12/1990 | Terry, Jr. |
| 5,025,807 A * | 6/1991 | Zabara ........................ 607/45 |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,223,254 A | 6/1993 | Paradiso et al. |
| 5,231,988 A | 8/1993 | Wernicke et al. |
| 5,235,980 A | 8/1993 | Varrichio et al. |
| 5,237,991 A | 8/1993 | Baker, Jr. et al. |

(Continued)

FOREIGN PATENT DOCUMENTS

CA    2 408 097    11/2001

(Continued)

OTHER PUBLICATIONS

U.S. Appl. No. 60/531,224, filed Dec. 19, 2003 for Skull-Mounted Electrical Stimulation System and Method for Treating Patients by Todd K. Whitehurst and Rafael Carbunaru.

(Continued)

*Primary Examiner*—Scott M. Getzow
(74) *Attorney, Agent, or Firm*—RatnerPrestia

(57) ABSTRACT

A method for treating a subject is provided, comprising positioning at least one electrode at least one site of the subject for less than about 3 hours, applying an electrical current to the site of the subject, and configuring the current to increase cerebral blood flow (CBF) of the subject, so as to treat a condition of the subject. The site is selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject.

30 Claims, 26 Drawing Sheets

U.S. PATENT DOCUMENTS

| | | |
|---|---|---|
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,304,632 A | 4/1994 | Vaudry et al. |
| 5,330,515 A | 7/1994 | Rutecki et al. |
| 5,335,657 A | 8/1994 | Terry, Jr. et al. |
| 5,351,394 A | 10/1994 | Weinberg |
| 5,531,778 A | 7/1996 | Maschino et al. |
| 5,540,730 A | 7/1996 | Terry, Jr. et al. |
| 5,571,150 A | 11/1996 | Wernicke et al. |
| 5,639,853 A | 6/1997 | Paradiso et al. |
| 5,707,400 A | 1/1998 | Terry, Jr. et al. |
| 5,725,471 A | 3/1998 | Davey et al. |
| 5,752,515 A | 5/1998 | Jolesz et al. |
| 5,756,071 A | 5/1998 | Mattern et al. |
| 5,928,272 A | 7/1999 | Adkins et al. |
| 5,938,689 A | 8/1999 | Fischell et al. |
| 6,006,124 A | 12/1999 | Fischell et al. |
| 6,016,449 A | 1/2000 | Fischell et al. |
| 6,061,593 A | 5/2000 | Fischell et al. |
| 6,086,525 A | 7/2000 | Davey et al. |
| 6,128,538 A | 10/2000 | Fischell et al. |
| 6,134,474 A | 10/2000 | Fischell et al. |
| 6,161,045 A | 12/2000 | Fischell et al. |
| 6,230,049 B1 | 5/2001 | Fischell et al. |
| 6,232,326 B1 | 5/2001 | Nelson |
| 6,277,841 B1 | 8/2001 | Rajagopalan et al. |
| 6,325,475 B1 | 12/2001 | Hayes et al. |
| 6,338,715 B1 | 1/2002 | Hayes et al. |
| 6,353,754 B1 | 3/2002 | Fischell et al. |
| 6,354,299 B1 | 3/2002 | Fischell et al. |
| 6,360,122 B1 | 3/2002 | Fischell et al. |
| 6,405,079 B1 | 6/2002 | Ansarinia |
| 6,427,086 B1 | 7/2002 | Fischell et al. |
| 6,432,986 B1 | 8/2002 | Levin |
| 6,459,936 B1 | 10/2002 | Fischell et al. |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,480,743 B1 | 11/2002 | Kirkpatrick et al. |
| 6,491,940 B1 | 12/2002 | Levin |
| 6,526,318 B1 | 2/2003 | Ansarinia |
| 6,529,774 B1 | 3/2003 | Greene |
| 6,531,454 B1 | 3/2003 | Leary et al. |
| 6,587,719 B1 | 7/2003 | Barrett et al. |
| 6,591,137 B1 | 7/2003 | Fischell et al. |
| 6,591,138 B1 | 7/2003 | Fischell et al. |
| 6,597,953 B1 | 7/2003 | Boling |
| 6,597,954 B1 | 7/2003 | Pless et al. |
| 6,606,521 B1 | 8/2003 | Paspa et al. |
| 6,609,025 B1 | 8/2003 | Barrett et al. |
| 6,609,956 B1 | 8/2003 | Margaria |
| 6,618,623 B1 | 9/2003 | Pless et al. |
| 6,622,038 B1 | 9/2003 | Barrett et al. |
| 6,622,041 B1 | 9/2003 | Terry, Jr. et al. |
| 6,622,047 B1 | 9/2003 | Barrett et al. |
| 6,647,296 B1 | 11/2003 | Fischell et al. |
| 6,662,035 B1 | 12/2003 | Sochor |
| 6,690,974 B1 | 2/2004 | Archer et al. |
| 6,810,285 B1 | 10/2004 | Pless et al. |
| 6,811,788 B1 | 11/2004 | Yu |
| 6,853,858 B1 | 2/2005 | Shalev |
| 6,905,827 B1 | 6/2005 | Wohlgemuth et al. |
| 2001/0004644 A1 | 6/2001 | Levin |
| 2002/0026652 A1 | 2/2002 | Allen et al. |
| 2002/0044919 A1 | 4/2002 | Yu |
| 2002/0099412 A1 | 7/2002 | Fischell et al. |
| 2002/0133841 A1 | 9/2002 | Leviten |
| 2002/0169307 A1 | 11/2002 | Klein |
| 2002/0169485 A1 | 11/2002 | Pless et al. |
| 2003/0005473 A1 | 1/2003 | Brennan et al. |
| 2003/0005477 A1 | 1/2003 | Leviten |
| 2003/0013136 A1 | 1/2003 | Balser et al. |
| 2003/0014772 A1 | 1/2003 | Allen |
| 2003/0018988 A1 | 1/2003 | Allen et al. |
| 2003/0018989 A1 | 1/2003 | Brennan et al. |
| 2003/0050527 A1 | 3/2003 | Fox et al. |
| 2003/0051268 A1 | 3/2003 | Allen |
| 2003/0056238 A1 | 3/2003 | Wisotzkey |
| 2003/0073917 A1 | 4/2003 | Echauz et al. |
| 2003/0074033 A1 | 4/2003 | Pless et al. |
| 2003/0079742 A1 | 5/2003 | Giroux |
| 2003/0106083 A1 | 6/2003 | Allen |
| 2003/0131367 A1 | 7/2003 | Guenther et al. |
| 2003/0133877 A1 | 7/2003 | Levin |
| 2003/0144711 A1 | 7/2003 | Pless et al. |
| 2003/0149457 A1 | 8/2003 | Tcheng et al. |
| 2003/0166099 A1 | 9/2003 | Sabbadini et al. |
| 2003/0166279 A1 | 9/2003 | Sabbadini et al. |
| 2003/0172390 A1 | 9/2003 | Wisotzkey et al. |
| 2003/0176898 A1 | 9/2003 | Gross et al. |
| 2003/0177514 A1 | 9/2003 | Leviten |
| 2003/0190601 A1 | 10/2003 | Sabbadini et al. |
| 2003/0190683 A1 | 10/2003 | Sabbadini et al. |
| 2003/0190749 A1 | 10/2003 | Surber et al. |
| 2003/0194714 A1 | 10/2003 | Sabbadini et al. |
| 2003/0195588 A1 | 10/2003 | Fischell et al. |
| 2003/0195602 A1 | 10/2003 | Boling |
| 2003/0198995 A1 | 10/2003 | Sabbadini et al. |
| 2003/0198996 A1 | 10/2003 | Surber et al. |
| 2003/0199005 A1 | 10/2003 | Sabbadini et al. |
| 2003/0199088 A1 | 10/2003 | Sabbadini et al. |
| 2003/0199089 A1 | 10/2003 | Surber et al. |
| 2003/0202937 A1 | 10/2003 | Sabbadini et al. |
| 2003/0203411 A1 | 10/2003 | Sabbadini et al. |
| 2003/0203481 A1 | 10/2003 | Surber et al. |
| 2003/0207833 A1 | 11/2003 | Berkley et al. |
| 2003/0211086 A1 | 11/2003 | Berkley et al. |
| 2003/0211599 A1 | 11/2003 | Sabbadini et al. |
| 2003/0219408 A1 | 11/2003 | Sabbadini et al. |
| 2003/0219888 A1 | 11/2003 | Segall et al. |
| 2003/0224369 A1 | 12/2003 | Surber et al. |
| 2003/0224444 A1 | 12/2003 | Sabbadini et al. |
| 2003/0232335 A1 | 12/2003 | Surber et al. |
| 2004/0015068 A1 | 1/2004 | Shalev et al. |
| 2004/0033491 A1 | 2/2004 | Alsobrook, II et al. |
| 2004/0054297 A1 | 3/2004 | Wingeier et al. |
| 2004/0136950 A1 | 7/2004 | Ni et al. |
| 2004/0136951 A1 | 7/2004 | Ni et al. |
| 2004/0153129 A1 | 8/2004 | Pless et al. |
| 2004/0210269 A1 | 10/2004 | Shalev et al. |
| 2004/0220644 A1 | 11/2004 | Shalev et al. |
| 2005/0020519 A1 | 1/2005 | Albiston et al. |
| 2005/0074506 A1 | 4/2005 | Natan et al. |
| 2005/0112090 A9 | 5/2005 | Ni et al. |
| 2005/0118187 A1 | 6/2005 | Yu |
| 2005/0137646 A1 | 6/2005 | Wallace et al. |
| 2005/0137647 A1 | 6/2005 | Wallace et al. |
| 2005/0159790 A1 | 7/2005 | Shalev |
| 2005/0266099 A1 | 12/2005 | Shalev |

FOREIGN PATENT DOCUMENTS

| | | |
|---|---|---|
| CA | 2 401 098 A1 | 1/2002 |
| CA | 2 433 376 A1 | 8/2002 |
| EP | 0 814 089 A2 | 12/1997 |
| EP | 0 610 301 B1 | 2/1998 |
| EP | 0 726 791 B1 | 6/2000 |
| EP | 0 588 957 B1 | 9/2000 |
| EP | 0 613 389 B1 | 9/2001 |
| WO | WO 89/02935 | 4/1989 |
| WO | WO 93/03762 | 3/1993 |

| | | |
|---|---|---|
| WO | WO 93/09841 | 5/1993 |
| WO | WO 93/25271 | 12/1993 |
| WO | WO 94/00185 | 1/1994 |
| WO | WO 94/00188 | 1/1994 |
| WO | WO 94/00189 | 1/1994 |
| WO | WO 95/14028 | 5/1995 |
| WO | WO 98/30709 | 7/1998 |
| WO | WO 99/03473 | 1/1999 |
| WO | WO 99/56822 | 11/1999 |
| WO | WO 00/44432 | 8/2000 |
| WO | WO 01/26729 A1 | 4/2001 |
| WO | WO 01/38581 A2 | 5/2001 |
| WO | WO 01/43733 A2 | 6/2001 |
| WO | WO 01/43733 A3 | 6/2001 |
| WO | WO 01/52868 A1 | 7/2001 |
| WO | WO 01/53455 A2 | 7/2001 |
| WO | WO 01/57190 A2 | 8/2001 |
| WO | WO 01/64835 A2 | 9/2001 |
| WO | WO 01/67855 A2 | 9/2001 |
| WO | WO 01/85094 A2 | 11/2001 |
| WO | WO 01/85094 A3 | 11/2001 |
| WO | WO 01/88088 A2 | 11/2001 |
| WO | WO 01/97905 A1 | 12/2001 |
| WO | WO 01/98508 A2 | 12/2001 |
| WO | WO 02/04068 A1 | 1/2002 |
| WO | WO 02/06339 A2 | 1/2002 |
| WO | WO 02/06445 A2 | 1/2002 |
| WO | WO 02/16439 A2 | 2/2002 |
| WO | WO 02/32504 A2 | 4/2002 |
| WO | WO 02/32504 A3 | 4/2002 |
| WO | WO 02/42735 A2 | 5/2002 |
| WO | WO 02/45498 A2 | 6/2002 |
| WO | WO 02/46229 A2 | 6/2002 |
| WO | WO 02/46390 A2 | 6/2002 |
| WO | WO 02/46409 A2 | 6/2002 |
| WO | WO 02/47477 A2 | 6/2002 |
| WO | WO 02/48345 A2 | 6/2002 |
| WO | WO 02/057450 A2 | 7/2002 |
| WO | WO 02/059315 A2 | 8/2002 |
| WO | WO 02/062291 A2 | 8/2002 |
| WO | WO 02/064791 A2 | 8/2002 |
| WO | WO 02/066643 A2 | 8/2002 |
| WO | WO 02/068029 A2 | 9/2002 |
| WO | WO 02/068029 A3 | 9/2002 |
| WO | WO 02/068031 A2 | 9/2002 |
| WO | WO 02/068031 A3 | 9/2002 |
| WO | WO 02/079424 A2 | 10/2002 |
| WO | WO 02/079438 A2 | 10/2002 |
| WO | WO 02/079439 A2 | 10/2002 |
| WO | WO 02/079440 A2 | 10/2002 |
| WO | WO 02/079444 A2 | 10/2002 |
| WO | WO 02/081510 A2 | 10/2002 |
| WO | WO 02/081658 A2 | 10/2002 |
| WO | WO 03/000046 A1 | 1/2003 |
| WO | WO 03/000310 A2 | 1/2003 |
| WO | WO 03/001883 A2 | 1/2003 |
| WO | WO 03/011304 A1 | 2/2003 |
| WO | WO 03/011392 A2 | 2/2003 |
| WO | WO 03/011393 A1 | 2/2003 |
| WO | WO 03/018107 A2 | 3/2003 |
| WO | WO 03/018108 A2 | 3/2003 |
| WO | WO 03/020350 A1 | 3/2003 |
| WO | WO 03/026395 A2 | 4/2003 |
| WO | WO 03/026401 A2 | 4/2003 |
| WO | WO 03/033672 A2 | 4/2003 |
| WO | WO 03/063959 A1 | 8/2003 |
| WO | WO 03/072014 A2 | 9/2003 |
| WO | WO 03/076008 A1 | 9/2003 |
| WO | WO 03/080795 A2 | 10/2003 |
| WO | WO 03/084591 A1 | 10/2003 |
| WO | WO 03/090599 A2 | 11/2003 |
| WO | WO 03/105658 A2 | 12/2003 |
| WO | WO 2004/098515 A2 | 11/2004 |
| WO | WO 2004/113391 A2 | 12/2004 |
| WO | WO 2005/002467 A2 | 1/2005 |
| WO | WO 2005/015404 A2 | 2/2005 |
| WO | WO 2005/030025 A2 | 4/2005 |
| WO | WO 2005/030118 A2 | 4/2005 |

OTHER PUBLICATIONS

U.S. Appl. No. 10/428,743, filed May 24, 2002 for Treatment of Epilepsy by Brian Stimulation by Todd K. Whitehurst.

U.S. Appl. No. 60/265,008, filed Jan. 30, 2001 for Fully Implantable Miniature Neurostimulator for Stimulation as a Therapy for Epilepsy by Todd K. Whitehurst and James P. McGivern.

U.S. Appl. No. 60/383,317, filed May 24, 2002 for Electrical Stimulation and Drug Infusion Systems and Methods for Treatment of Epilepsy by Todd K. Whitehurst.

U.S. Appl. No. 60/505,831, filed Sep. 25, 2003 for Skull-Mounted Electrical Stimulation System by Todd K. Whitehurst and Rafael Carbunaru.

USPTO Non-Final Office Action mailed Dec. 16, 2005 for U.S. Appl. No. 10/753,882.

USPTO Non-Final Office Action mailed Oct. 4, 2005 for U.S. Appl. No. 10/294,310.

Delépine, L. et al., "Plasma Protein Extravasation Induced in the Rat Dura Mater by Stimulation of the Parasympathetic Spenopalatine Ganglion," Experimental Neurology 147, 389-400, 1997, Article No. EN976614.

Hara, H. et al., "Parasympathetic Cerebrovascular Innervation: An Anterograde Tracing from the Spenopalatine Ganglion in the Rat," Neurosurgery 32(5), 822-827, May 1993.

Kroll, R. A. et al., "Outwitting the Blood Brain Barrier for Therapeutic Purposes: Osmotic Opening and Other Means," Neurosurgery, 42(5), 1083-1099, May 1998.

Sanders, M. et al., "Efficacy of spenopalatine ganglion blockade in 66 patients suffering from cluster headache: a 12- to 70- month follow-up evaluation," Journal of Neurosurgery, 87, 876-880, Dec. 1997.

Suzuki, N. et al., "Selective Stimulation of Postganglionic Cerebrovascular Parasympathetic Nerve Fibers Originating from the Spenopalatine Ganglion Enhances Cortical Blood Flow in the Rat," Journal of Cerebral Blood Flow and Metabolism, 10:383-391, 1990.

Major, A. et al., "Odorants Presented to the Rat Nasal Cavity Increase Cortical Blood Flow," Chem. Senses, 24:665-669, 1999.

Fusco, B.M. et al., "'Capsaicin-Sensitive' Sensory Neurons in Cluster Headache: Pathophysiological Aspects and Therapeutic Indication," Headache, 34:132-137, Mar. 1994.

Silver, W.L., "Neural and Pharmacological Basis for Nasal Irritation," in Tucker WG, Leaderer BP, Molhave L, Cain WS (eds), Sources of Indoor Air Contaminants, Annals New York Academy of Sciences, 641, 152-163, 1992.

Toda, N. et al., "Cerebral Vasodilatation Induced by Stimulation of the Pterygopalatine Ganglion and Greater Petrosal Nerve in Anesthetized Monkeys," Neuroscience 96(2): 393-398, 2000.

Roth, B.J. et al., "In vitro evaluation of a 4-leaf coil design for magnetic stimulation of peripheral nerve," Electroencephalography and Clinical Neurophysiology, 93, 68-74, 1994.

* cited by examiner

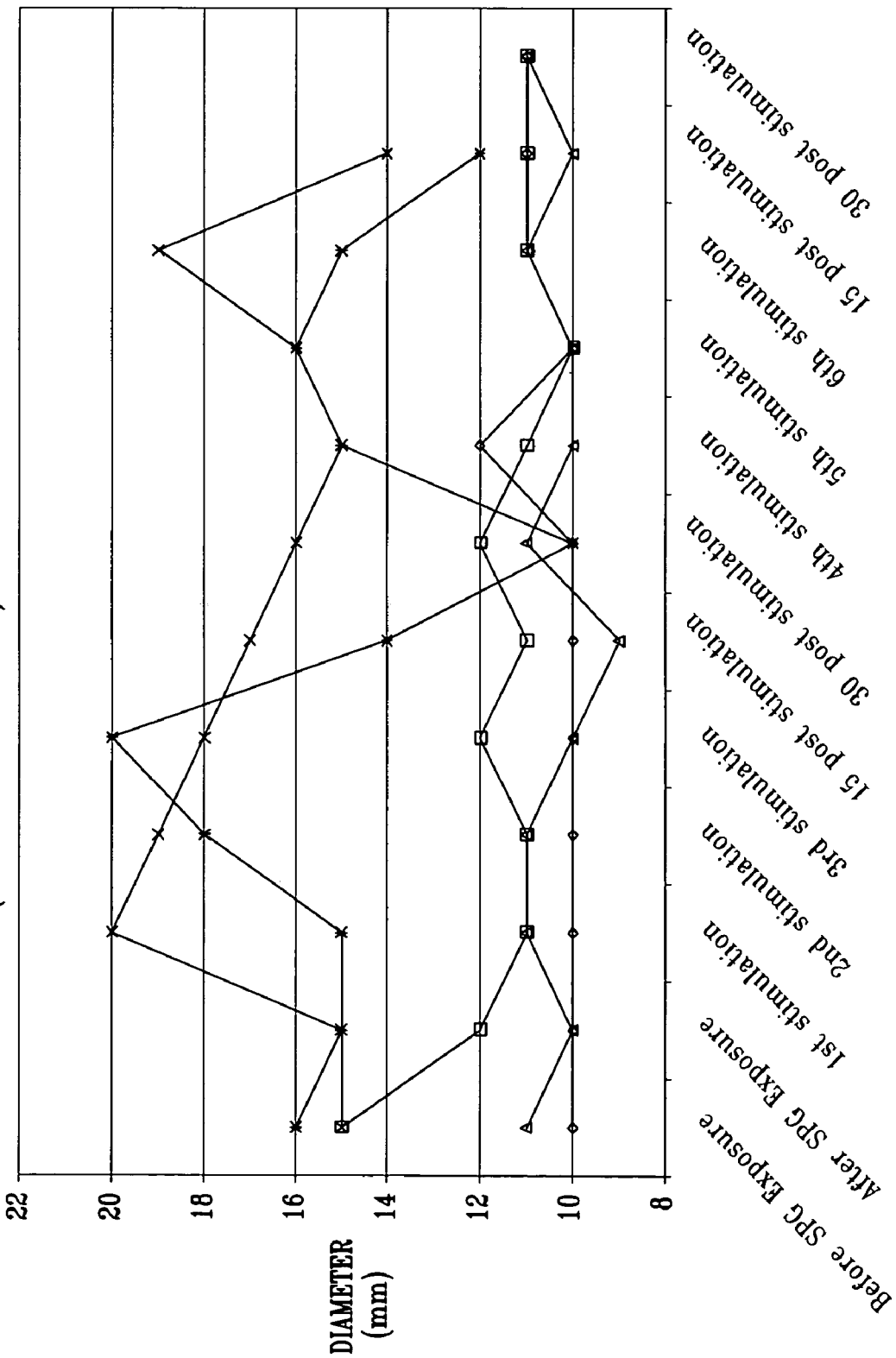
FIG. 17C RIGHT (NON-STIMULATION SIDE) MIDDLE CEREBRAL ARTERY

STIMULATION FOR ACUTE CONDITIONS

CROSS-REFERENCE TO RELATED APPLICATIONS

This application is a continuation-in-part of U.S. patent application Ser. No. 10/258,714, filed Jan. 22, 2003 entitled, "Method and apparatus for stimulating the sphenopalatine ganglion to modify properties of the BBB and cerebral blood flow," which is the US National Phase of PCT Application PCT/IL01/00402, filed May 7, 2001, which claims priority from U.S. Provisional Patent Application 60/203,172, filed May 8, 2000.

This application claims priority from U.S. provisional patent application 60/506,165, filed Sep. 26, 2003, entitled, "Diagnostic applications of stimulation."

Each of the above-cited patent applications is assigned to the assignee of the present patent application and is incorporated herein by reference.

FIELD OF THE INVENTION

The present invention relates generally to medical procedures and devices. More specifically, the invention relates to the use of electrical, magnetic, electromagnetic, chemical, and/or mechanical stimulation for treating medical conditions.

BACKGROUND OF THE INVENTION

The blood-brain barrier (BBB) is a unique feature of the central nervous system (CNS) which isolates the brain from the systemic blood circulation. To maintain the homeostasis of the CNS, the BBB prevents access to the brain of many substances circulating in the blood.

The BBB is formed by a complex cellular system of endothelial cells, astroglia, pericytes, perivascular macrophages, and a basal lamina. Compared to other tissues, brain endothelia have the most intimate cell-to-cell connections: endothelial cells adhere strongly to each other, forming structures specific to the CNS called "tight junctions" or zonula occludens. They involve two opposing plasma membranes which form a membrane fusion with cytoplasmic densities on either side. These tight junctions prevent cell migration or cell movement between endothelial cells. A continuous uniform basement membrane surrounds the brain capillaries. This basal lamina encloses contractile cells called pericytes, which form an intermittent layer and probably play some role in phagocytosis activity and defense if the BBB is breached. Astrocytic end feet, which cover the brain capillaries, build a continuous sleeve and maintain the integrity of the BBB by the synthesis and secretion of soluble growth factors (e.g., gamma-glutamyl transpeptidase) essential for the endothelial cells to develop their BBB characteristics.

PCT Patent Publication WO 01/85094 to Shalev and Gross, which is assigned to the assignee of the present patent application and is incorporated herein by reference, describes apparatus for modifying a property of a brain of a patient, including electrodes applied to a sphenopalatine ganglion (SPG) or a neural tract originating in or leading to the SPG. A control unit drives the electrodes to apply a current capable of inducing (a) an increase in permeability of a blood-brain barrier (BBB) of the patient, (b) a change in cerebral blood flow of the patient, and/or (c) an inhibition of parasympathetic activity of the SPG.

U.S. Pat. No. 5,756,071 to Mattern et al., which is incorporated herein by reference, describes a method for nasally administering aerosols of therapeutic agents to enhance penetration of the blood brain barrier. The patent describes a metering spray designed for per nasal application, the spray containing at least one sex hormone or at least one metabolic precursor of a sex hormone or at least one derivative of a sex hormone or combinations of these, excepting the precursors of testosterone, or at least one biogenic amine, with the exception of catecholamines.

U.S. Pat. No. 5,752,515 to Jolesz et al., which is incorporated herein by reference, describes apparatus for image-guided ultrasound delivery of compounds through the blood-brain barrier. Ultrasound is applied to a site in the brain to effect in the tissues and/or fluids at that location a change detectable by imaging. At least a portion of the brain in the vicinity of the selected location is imaged, e.g., via magnetic resonance imaging, to confirm the location of that change. A compound, e.g., a neuropharmaceutical, in the patient's bloodstream is delivered to the confirmed location by applying ultrasound to effect opening of the blood-brain barrier at that location and, thereby, to induce uptake of the compound there.

U.S. Pat. No. 6,526,318 to Ansarinia and related PCT Publication WO 01/97905 to Ansarinia, which are incorporated herein by reference, describe a method for the suppression or prevention of various medical conditions, including pain, movement disorders, autonomic disorders, and neuropsychiatric disorders. The method includes positioning an electrode on or proximate to at least one of the patient's SPG, sphenopalatine nerves, or vidian nerves, and activating the electrode to apply an electrical signal to such nerve. In a further embodiment for treating the same conditions, the electrode used is activated to dispense a medication solution or analgesic to such nerve. The '318 patent and '905 publication also describe surgical techniques for implanting the electrode.

U.S. Pat. No. 6,405,079 to Ansarinia, which is incorporated herein by reference, describes a method for the suppression or prevention of various medical conditions, including pain, movement disorders, autonomic disorders, and neuropsychiatric disorders. The method includes positioning an electrode adjacent to or around a sinus, the dura adjacent a sinus, or falx cerebri, and activating the electrode to apply an electrical signal to the site. In a further embodiment for treating the same conditions, the electrode dispenses a medication solution or analgesic to the site. The '079 patent also describes surgical techniques for implanting the electrode.

PCT Publications WO 03/084591, WO 03/020350, WO 03/000310, WO 02/068031, and WO 02/068029 to Djupesland, which are incorporated herein by reference, describe nasal delivery devices. US Patent Application Publication 2003/0079742 to Giroux, which is incorporated herein by reference, describes a nasal nebulizer.

U.S. Pat. Nos. 5,725,471 and 6,086,525 to Davey et al., which are incorporated herein by reference, describe a magnetic nerve stimulator system comprising a core of highly saturable material with a coil winding. A thyristor capacitive discharge circuit pulses the device. A rapidly changing magnetic field is guided by the core, preferably vanadium permendur. A C-shape is employed for focusing the stimulation.

PCT Publication WO 02/32504 to Zanger et al., which is incorporated herein by reference, describes a transcranial magnetic stimulation (TMS) device for treating certain physiological conditions, such as cardiovascular or neurophysiological conditions, or for studying the physiology of the body.

US Patent Application Publication 2003/0050527 to Fox et al., which is incorporated herein by reference, describes apparatus and methods for delivery of TMS. The apparatus includes a TMS coil which when energized generates an electric field substantially parallel to a long axis of the coil and substantially normal to a surface of the coil.

U.S. Pat. No. 6,432,986 to Levin and PCT Publication Wo 99/03473 to Levin, which are incorporated herein by reference, describe techniques for inhibiting a cerebral neurovascular disorder or a muscular headache. The techniques include intranasally administering a pharmaceutical composition comprising a long-acting local anesthetic.

U.S. Pat. No. 6,491,940 to Levin, U.S. Patent Application 2003/0133877 to Levin, and PCT Publication WO 00/44432 to Levin, which are incorporated herein by reference, describe techniques for inhibiting a cerebral neurovascular disorder or a muscular headache. The techniques include intranasally administering a pharmaceutical composition comprising a long-acting local anesthetic. Apparatus for delivering or applying the composition is also described.

U.S. Patent Application 2001/0004644 to Levin and PCT Publication WO 01/43733 to Levin, which are incorporated herein by reference, describe techniques for inhibiting cephalic inflammation, including meningeal inflammation and cerebral inflammation. The techniques include intranasally administering a long-acting local anesthetic. Apparatus for delivering or applying the composition is also described, including a dorsonasally implanted electronic neural stimulator, such as a transepithelial neural stimulation device.

An article entitled "Endoscopic transnasal neurolytic sphenopalatine ganglion block for head and neck cancer pain," by Varghese et al., J Laryngol Otol. 2001 May; 115(5):385–7, which is incorporated herein by reference, describes nasal endoscopy as a valuable adjunct to the localization of the sphenopalatine ganglion. Twenty-two patients with advanced malignancies of the head and neck region whose pain was not adequately controlled with conventional medications, including oral morphine, were given nasal endoscopically-guided neurolytic sphenopalatine ganglion block with six percent phenol, after a prognostic block with local anesthetic solution. Seventeen patients had good immediate relief. One had partial relief and four had inadequate relief. On follow-up for one month, the patients had significantly lower pain intensity and the pain was more manageable with oral medication.

The following references, which are incorporated herein by reference, may be useful:

Delepine L, Aubineau P, "Plasma protein extravasation induced in the rat dura mater by stimulation of the parasympathetic sphenopalatine ganglion," Experimental Neurology, 147, 389–400 (1997)

Hara H, Zhang Q J, Kuroyanagi T, Kobayashi S, "Parasympathetic cerebrovascular innervation: An anterograde tracing from the sphenopalatine ganglion in the rat," Neurosurgery, 32, 822–827 (1993)

Jolliet-Riant P, Tillement J P, "Drug transfer across the blood-brain barrier and improvement of brain delivery," Fundam. Clin. Pharmacol., 13, 16–25 (1999)

Kroll R A, Neuwelt E A, "Outwitting the blood brain barrier for therapeutic purposes: Osmotic opening and other means," Neurosurgery, 42, 1083–1100 (1998)

Sanders M, Zuurmond W W, "Efficacy of sphenopalatine ganglion blockade in 66 patients suffering from cluster headache: A 12–70 month follow-up evaluation," Journal of Neurosurgery, 87, 876–880 (1997)

Syelaz J, Hara H, Pinard E, Mraovitch S, MacKenzie E T, Edvinsson L, "Effects of stimulation of the sphenopalatine ganglion on cortical blood flow in the rat," Journal of Cerebral Blood Flow and Metabolism," 8, 875–878 (1988)

Van de Waterbeemd H, Camenisch G, Folkers G, Chretien J R, Raevsky O A, "Estimation of blood brain barrier crossing of drugs using molecular size and shape and h bonding descriptors," Journal of Drug Targeting," 6, 151–165, (1998)

Suzuki N, Hardebo J E, Kahrstrom J, Owman C, "Selective electrical stimulation of postganglionic cerebrovascular parasympathetic nerve fibers originating from the sphenopalatine ganglion enhances cortical blood flow in the rat," Journal of Cerebral Blood Flow and Metabolism, 10, 383–391 (1990)

Suzuki N, Hardebo J E, Kahrstrom J, Owman C H, "Effect on cortical blood flow of electrical stimulation of trigeminal cerebrovascular nerve fibres in the rat," Acta Physiol. Scand., 138, 307–315 (1990)

Major A, Silver W, "Odorants presented to the rat nasal cavity increase cortical blood flow," Chem. Senses, 24, 665–669 (1999)

Fusco B M, Fiore G, Gallo F, Martelletti P, Giacovazzo M, "'Capsaicin-sensitive' sensory neurons in cluster headache: pathophysiological aspects and therapeutic indications," Headache, 34, 132–137 (1994)

Lambert G A, Bogduk N, Goadsby P J, Duckworth J W, Lance J W, "Decreased carotid arterial resistance in cats in response to trigeminal stimulation," Journal of Neurosurgery, 61, 307–315 (1984)

Silver W L, "Neural and pharmacological basis for nasal irritation," in Tucker W G, Leaderer B P, Mølhave L, Cain W S (eds), Sources of Indoor Air Contaminants, Ann. NY Acad. Sci., 641, 152–163 (1992)

Silver W, "Chemesthesis: the burning questions," ChemoSense, Vol. 2, 1–2 (1999)

Devoghel J C, "Cluster headache and sphenopalatine block," Acta Anaesthesiol Belg., 32(1):101–7 (1981)

Branston N M, "The physiology of the cerebrovascular parasympathetic innervation," British Journal of Neurosurgery 9:319–329 (1995)

Branston N M et al., "Contribution of cerebrovascular parasympathetic and sensory innervation to the short-term control of blood flow in rat cerebral cortex," J Cereb Blood Flow Metab 15(3):525–31 (1995)

Toda N et al., "Cerebral vasodilation induced by stimulation of the pterygopalatine ganglion and greater petrosal nerve in anesthetized monkeys," Neuroscience 96(2):393–398 (2000)

Seylaz J et al., "Effect of stimulation of the sphenopalatine ganglion on cortical blood flow in the rat," J Cereb Blood Flow Metab 8(6):875–8 (1988)

Nollet H et al., "Transcranial magnetic stimulation: review of the technique, basic principles and applications," The Veterinary Journal 166:28–42 (2003)

Van Gijn J et al., "Subarachnoid haemorrhage: diagnosis, causes and management," Brain 124:249–278 (2001)

Goadsby P J et al., "Effect of stimulation of trigeminal ganglion on regional cerebral blood flow in cats," Am J Physiol 22:R270–R274 (1987)

Walters B B et al., "Cerebrovascular projections from the sphenopalatine and otic ganglia to the middle cerebral artery of the cat," Stroke 17:488–494 (1986)

Suzuki N et al., "Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595–604 (1989)

Roth B J et al., "In vitro evaluation of a 4-leaf coil design for magnetic stimulation of peripheral nerve," Electroencephalography and Clinical Neurophysiology 93:68–74 (1994)

SUMMARY OF THE INVENTION

In some embodiments of the present invention, an acute and/or emergency medical condition of a subject is treated by stimulating at least one "modulation target site" (MTS), as defined hereinbelow, by applying electrical, magnetic, electromagnetic, chemical, and/or mechanical stimulation to the site. Such treatment is typically applied as soon as possible after diagnosis of the condition, such as in an emergency room or wherever the subject happens to be. For some conditions, such as acute brain injury (e.g., ischemic stroke, vasospasm following subarachnoid hemorrhage (SAH), traumatic brain injury (TBI), or seizure), the stimulation is configured so as to dilate cerebral vessels, thereby increasing blood flow to affected brain tissue and tissue in a vicinity thereof, and decreasing damage caused by the condition. For other conditions, such as occlusion within the retinal circulation, the stimulation is configured so as to dilate blood vessels, thereby increasing retinal blood flow and treating the condition. For treating complications of SAH, the stimulation is typically applied after surgery has been performed to treat an aneurysm that caused the SAH; the stimulation counteracts the reduced cerebral blood flow (CBF) sometimes caused by blood passage into the subarachnoid space.

In the present patent application, a "modulation target site" (MTS) consists of:
- a sphenopalatine ganglion (SPG) (also called a pterygopalatine ganglion);
- a nerve of the pterygoid canal (also called a vidian nerve), such as a greater superficial petrosal nerve (a preganglionic parasympathetic nerve) or a lesser deep petrosal nerve (a postganglionic sympathetic nerve);
- a greater palatine nerve;
- a lesser palatine nerve;
- a sphenopalatine nerve;
- a communicating branch between the maxillary nerve and the sphenopalatine ganglion;
- an otic ganglion;
- an afferent fiber going into the otic ganglion;
- an efferent fiber going out of the otic ganglion; or
- an infraorbital nerve.

In some embodiments of the present invention, electrical stimulation is applied to the SPG system, as defined hereinbelow, and/or to at least one other appropriate MTS, using a substantially rigid support element comprising one or more electrodes, adapted to be quickly inserted into the site and removed upon completion of the acute treatment. For applications in which the MTS includes an SPG of the subject, the support element is typically inserted, (a) via the nose, through the sphenopalatine foramen, or (b) via the roof of the oral cavity, through the greater palatine canal. The support element typically comprises a mark or stopper that indicates the point at which the support element has been sufficiently inserted via the appropriate foramen.

In the present patent application, "SPG system" means the SPG and associated neuroanatomical structures, including neural tracts originating in or reaching the SPG, including outgoing and incoming parasympathetic and sympathetic tracts, which tracts include preganglionic fibers of the SPG (e.g., fibers contained within the vidian nerve) and postganglionic fibers of the SPG (fibers that travel anterogradely from the SPG toward the brain vascular bed, including the retro-orbital branches of the SPG, which are fibers that connect the SPG with orbital neural structures).

In some embodiments of the present invention, magnetic stimulation is applied to at least one MTS using a magnetic induction device that comprises a control unit, and at least one coil that is adapted to be placed in a vicinity of the MTS. For some applications, e.g., in which the MTS includes an SPG of the subject, the coil is adapted to be inserted into a nasal cavity of the subject. Alternatively, the coil is adapted to be placed in a vicinity of a temporomandibular joint, in a vicinity of the MTS. Further alternatively, the coil is adapted to be placed completely or partially around the head, and to focus the magnetic field on the MTS.

In some embodiments of the present invention, chemical stimulation of the SPG system, and/or of at least one other appropriate MTS, is achieved by presenting chemicals, for example in a liquid or gaseous state, to an air passage of the subject, such as a nasal cavity or a throat, or in a vicinity thereof. The temporal profile and other quantitative characteristics of such chemical modulation are believed by the present inventors to have a mechanism of action that has a neuroanatomical basis overlapping with that of the electrical modulation of the MTS. Furthermore, experimental animal evidence collected by the inventors and described in U.S. Provisional Patent Application 60/368,657 to Shalev and Gross entitled, "SPG stimulation," filed Mar. 28, 2002, which is assigned to the assignee of the present invention and is incorporated herein by reference, suggest a correlation between the mechanisms of increasing cerebral blood flow and increased cerebrovascular permeability. For some applications, chemical-presentation techniques described herein are practiced in combination with techniques described in U.S. Provisional Patent Application 60/376,048, filed Apr. 25, 2002, entitled, "Methods and apparatus for modifying properties of the BBB and cerebral circulation by using the neuroexcitatory and/or neuroinhibitory effects of odorants on nerves in the head," which is assigned to the assignee of the present patent application and is incorporated herein by reference.

Chemicals that may increase or decrease cerebral blood flow and/or the permeability of the blood-brain barrier (e.g., via modulation of SPG-related fibers), include, but are not limited to, propionic acid, cyclohexanone, amyl acetate, acetic acid, citric acid, carbon dioxide, sodium chloride, ammonia, menthol, alcohol, nicotine, piperine, gingerol, zingerone, allyl isothiocyanate, cinnamaldehyde, cuminaldehyde, 2-propenyl/2-phenylethyl isothiocyanate, thymol, and eucalyptol. The chemicals reach the appropriate neural structures and induce vasodilatation, vasoconstriction and/or cerebrovascular permeability changes.

In some embodiments of the present invention, chemical stimulation is applied to the SPG system, and/or to at least one other appropriate MTS, using (a) a nasal applicator adapted to deliver the stimulating chemical to an upper region of the nasal cavity, or (b) a transpalatine applicator inserted via the greater palatine canal.

In some embodiments of the present invention, stimulation of the MTS is achieved by applying mechanical stimulation to the MTS, e.g., vibration.

In some embodiments of the present invention, stimulation of at least one MTS is achieved by applying a neuroexcitatory agent to the MTS. Suitable neuroexcitatory agents include, but are not limited to, acetylcholine and urocholine. For some applications, the MTS is stimulated by applying a neuroinhibitory agent, such as atropine, hexamethonium, or a local anesthetic (e.g., lidocaine).

In some embodiments of the present invention, the short-term MTS stimulation techniques described herein are used in order to facilitate a diagnosis of a condition of the central nervous system (CNS). For some applications, stimulation of the MTS enhances delivery of diagnostic molecules across the BBB by modulation of at least one MTS and/or another parasympathetic center. These techniques typically stimulate the nerve fibers of the MTS, thereby inducing the middle and anterior cerebral arteries to dilate, and also result in increased CNS bioavailability of various compounds. In this manner, the movement of large diagnostic molecules from within blood vessels to the CNS parenchyma, is substantially increased.

For other applications, stimulation of the MTS enhances clearance of at least one constituent of the CNS, such as a protein, from the CNS, across the BBB, and into the systemic blood circulation of the subject. Once the constituent is in the blood circulation, a conventional blood assay is performed in order to detect the constituent. In the absence of the increased permeability of the BBB caused by the stimulation techniques described herein, these constituents do not generally cross the BBB to the blood circulation in quantities sufficient for accurate detection and diagnosis.

In some embodiments of the present invention, an SPG of the subject is indirectly activated by stimulating afferent fibers of the trigeminal nerve (cranial nerve V) of the subject, either electrically, magnetically, or electromagnetically. A reflex response to such stimulation leads to activation of the SPG. (For example, the maxillary branch of the trigeminal nerve directly contacts the SPG.) Typically, but not necessarily, such stimulation is performed while the subject is under general anesthesia or sedation. For some applications, cranial nerve V is stimulated by non-invasively attaching electrodes to the surface of the face of the subject, typically using techniques commonly used for transcutaneous electrical nerve stimulation (TENS). For example, TENS may be applied to a cheek or a tip of a nose of a subject.

In an embodiment of the present invention, an oral appliance is provided that is adapted to be brought into contact with a mucous membrane of a palate of an oral cavity of a subject. The appliance comprises one or more electrodes, which are driven to apply transmucosal electrical stimulation to nerve fibers within or immediately above the mucous membrane, which fibers directly innervate an SPG of the subject. Typically, but not necessarily, such stimulation is performed while the subject is under general anesthesia or sedation. Such transmucosal stimulation may require less current than the transcutaneous stimulation described hereinabove.

It is to be appreciated that references herein to specific modulation target sites are to be understood as including other modulation target sites, as appropriate.

It is further to be appreciated that insertion and modulation sites, methods of insertion and/or implantation, and parameters of modulation are described herein by way of illustration and not limitation, and that the scope of the present invention includes other possibilities which would be obvious to someone of ordinary skill in the art who has read the present patent application.

It is yet further to be appreciated that while some embodiments of the invention are generally described herein with respect to electrical transmission of power and electrical modulation of tissue, other modes of energy transport may be used as well. Such energy includes, but is not limited to, direct or induced electromagnetic energy, radiofrequency (RF) transmission, mechanical vibration, ultrasonic transmission, optical power, and low power laser energy (via, for example, a fiber optic cable).

It is additionally to be appreciated that whereas some embodiments of the present invention are described with respect to application of electrical currents to tissue, this is to be understood in the context of the present patent application and in the claims as being substantially equivalent to applying an electrical field, e.g., by creating a voltage drop between two electrodes.

There is therefore provided, in accordance with an embodiment of the present invention, apparatus for treating a subject, including:

an elongated generally rigid support element having a length of at least 1.8 cm, and having a distal end;

one or more electrodes fixed to the support element in a vicinity of the distal end thereof, and configured to be positioned in a vicinity of a site of the subject when the support element is inserted into a body of the subject, such that a portion of the support element remains outside of the body, the site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and a control unit, coupled to the support element, and adapted to drive the electrodes to apply an electrical current to the site, and to configure the current to increase cerebral blood flow (CBF) of the subject, so as to treat a condition of the subject.

For some applications, the condition includes one or more of the following, and the control unit is adapted to configure the current to increase the CBF to a level sufficient to treat the condition:

an acute ischemic condition of a brain of the subject;
a complication of subarachnoid hemorrhage (SAH) of the subject;
an acute brain injury of the subject;
vasospasm after stroke of the subject;
traumatic brain injury (TBI) of the subject;
a seizure of the subject;
occlusion within a retinal circulation of the subject;
retinal artery occlusion (RAO) of the subject; and/or
retinal venous occlusion (RVO) of the subject.

In an embodiment, the site includes the SPG of the subject, and the electrodes are configured to be positioned in the vicinity of the SPG.

For some applications, the support element is substantially straight. For some applications, the support element has a length between about 7 cm and about 13 cm. For some applications, a portion of the support element adapted for insertion into the body has a length of between about 2.5 cm and about 3 cm.

For some applications, the control unit is adapted to configure the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

In an embodiment, the support element is adapted to be positioned in the vicinity of the site by insertion through a roof of an oral cavity of the subject. For some applications, the support element is adapted to be positioned in the vicinity of the site by insertion through a greater palatine canal of the subject.

In an embodiment, the support element is adapted to be positioned in the vicinity of the site by insertion through a nose of the subject. For some applications, the support element is adapted to be positioned in the vicinity of the site by insertion through a sphenopalatine foramen of the subject.

For some applications, the support element includes at least one mark, adapted to indicate a depth of insertion of the support element in the body. For some applications, a distance of the mark from the distal end of the support element is between about 2.5 cm and about 3 cm.

For some applications, the support element includes a stopper, adapted to prevent insertion of the support element into the body beyond a certain depth. For some applications, a distance of the stopper from the distal end of the support element is between about 2.5 cm and about 3 cm.

For some applications, the support element is bent at one or more locations. For some applications, an angle of a bend of the support element is between about 20 and about 40 degrees. For some applications, a distance of a bend of the support element from the distal end of the support element is between about 2 cm and about 3 cm.

There is further provided, in accordance with an embodiment of the present invention, apparatus for treating a complication of subarachnoid hemorrhage (SAH) of a subject, including:
a medical vehicle, adapted to directly treat the SAH; and
a stimulator adapted to stimulate at least one site of the subject, so as to treat a complication arising from use of the medical vehicle, the site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject.

In an embodiment, the site includes the SPG of the subject, and the stimulator is adapted to stimulate the SPG.

In an embodiment, the stimulator is adapted to configure the stimulation to increase cerebral blood flow (CBF) of the subject.

For some applications, the medical vehicle includes a tool for clipping an aneurysm that caused the SAH. Alternatively or additionally, the medical vehicle includes a pharmaceutical composition for treating an aneurysm that caused the SAH.

For some applications, the stimulator includes an electrical stimulator, adapted to apply an electrical current to the site. Alternatively or additionally, the stimulator includes a magnetic stimulator, adapted to apply a magnetic field to the site. Further alternatively or additionally, the stimulator includes a chemical stimulator, adapted to apply a chemical to the site. Still further alternatively or additionally, the stimulator includes a mechanical stimulator, adapted to apply mechanical energy to the site.

There is also provided, in accordance with an embodiment of the present invention, apparatus for treating a condition of a subject, including:
a coil, adapted to be positioned in a vicinity of a site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and
a control unit, adapted to drive the coil to generate a magnetic field in the vicinity of the site capable of inducing an increase in cerebral blood flow (CBF) of the subject.

In an embodiment, the site includes the SPG of the subject, and the coil is adapted to be positioned in the vicinity of the SPG.

For some applications, the control unit is adapted to generate the magnetic field with a strength sufficient to stimulate the site, and insufficient to substantially stimulate brain tissue of the subject.

For some applications, the apparatus includes a cooling element, adapted to prevent excessive heating of the coil.

For some applications, the coil includes between about 4 and about 30 loops of wire.

In an embodiment, the coil is adapted to be inserted into a nasal cavity of the subject.

For some applications, the coil is substantially figure-eight-shaped. Alternatively, the coil is substantially 4-leaf-shaped. Further alternatively, the coil is substantially circular.

For some applications, the coil has a diameter of between about 3 mm and about 12 mm.

In an embodiment, the coil is adapted to be placed in a vicinity of a temporomandibular joint of the subject. For some applications, the coil has a diameter of between about 3 cm and about 12 cm.

In an embodiment, the coil is adapted to be placed around at least a portion of a head of the subject. For some applications, the coil has a diameter of between about 3 cm and about 12 cm.

There is additionally provided, in accordance with an embodiment of the present invention, apparatus for treating a condition of a subject, including:
a coil, adapted to be positioned in a vicinity of a site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and a control unit, adapted to drive the coil to generate a magnetic field in the vicinity of the site capable of inducing an increase in permeability of a blood-brain barrier (BBB) of the subject.

In an embodiment, the site includes the SPG of the subject, and the coil is adapted to be positioned in the vicinity of the SPG.

For some applications, the control unit is adapted to generate the magnetic field with a strength sufficient to stimulate the site, and insufficient to substantially stimulate brain tissue of the subject.

For some applications, the apparatus includes a cooling element, adapted to prevent excessive heating of the coil.

For some applications, the coil includes between about 4 and about 30 loops of wire.

In an embodiment, the coil is adapted to be inserted into a nasal cavity of the subject.

For some applications, the coil is substantially figure-eight-shaped. Alternatively, the coil is substantially 4-leaf-shaped. Further alternatively, the coil is substantially circular. For some applications, the coil has a diameter of between about 3 mm and about 12 mm.

In an embodiment, the coil is adapted to be placed in a vicinity of a temporomandibular joint of the subject. For some applications, the coil has a diameter of between about 30 mm and about 120 mm.

In an embodiment, the coil is adapted to be placed around at least a portion of a head of the subject. For some applications, the coil has a diameter of between about 10 cm and about 25 cm.

There is yet additionally provided, in accordance with an embodiment of the present invention, apparatus for facilitating a diagnosis of a condition of a subject, including:

an elongated generally rigid support element having a length of at least 1.8 cm, and having a distal end;

one or more electrodes fixed to the support element in a vicinity of the distal end thereof, and configured to be positioned in a vicinity of a site of the subject when the support element is inserted into a body of the subject, such that a portion of the support element remains outside of the body, the site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and a control unit, coupled to the support element, and adapted to:

drive the electrodes to apply an electrical current to the site, and configure the current to induce an increase in permeability of a blood-brain barrier (BBB) of the subject sufficient to increase passage of a diagnostic agent across the BBB into a central nervous system (CNS) of the subject.

In an embodiment, the site includes the SPG of the subject, and the electrodes are configured to be positioned in the vicinity of the SPG.

For some applications, the support element is substantially straight. For some applications, the support element has a length between about 7 cm and about 13 cm. For some applications, a portion of the support element adapted for insertion into the body has a length of between about 2.5 cm and about 3 cm.

For some applications, the control unit is adapted to configure the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

In an embodiment, the support element is adapted to be positioned in the vicinity of the site by insertion through a roof of an oral cavity of the subject. For some applications, the support element is adapted to be positioned in the vicinity of the site by insertion through a greater palatine canal of the subject.

In an embodiment, the support element is adapted to be positioned in the vicinity of the site by insertion through a nose of the subject. For some applications, the support element is adapted to be positioned in the vicinity of the site by insertion through a sphenopalatine foramen of the subject.

For some applications, the support element includes at least one mark, adapted to indicate a depth of insertion of the support element in the body. For some applications, a distance of the mark from the distal end of the support element is between about 2.5 cm and about 3 cm.

For some applications, the support element includes a stopper, adapted to prevent insertion of the support element into the body beyond a certain depth. For some applications, a distance of the stopper from the distal end of the support element is between about 2.5 cm and about 3 cm.

For some applications, the support element is bent at one or more locations. For some applications, an angle of a bend of the support element is between about 20 and about 40 degrees. For some applications, a distance of a bend of the support element from the distal end of the support element is between about 2 cm and about 3 cm.

There is still additionally provided, in accordance with an embodiment of the present invention, apparatus for facilitating delivery of a drug to a subject, including:

an elongated generally rigid support element having a length of at least 1.8 cm, and having a distal end;

one or more electrodes fixed to the support element in a vicinity of the distal end thereof, and configured to be positioned in a vicinity of a site of the subject when the support element is inserted into a body of the subject, such that a portion of the support element remains outside of the body, the site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and a control unit, coupled to the support element, and adapted to:

drive the electrodes to apply an electrical current to the site, and configure the current to induce an increase in permeability of a blood-brain barrier (BBB) of the subject sufficient to increase passage of the drug across the BBB into a central nervous system (CNS) of the subject.

In an embodiment, the site includes the SPG of the subject, and the electrodes are configured to be positioned in the vicinity of the SPG.

In an embodiment, the support element is substantially straight. For some applications, the support element has a length between about 7 cm and about 13 cm.

For some applications, a portion of the support element adapted for insertion into the body has a length of between about 2.5 cm and about 3 cm.

For some applications, the control unit is adapted to configure the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

In an embodiment, the support element is adapted to be positioned in the vicinity of the site by insertion through a roof of an oral cavity of the subject. For some applications, the support element is adapted to be positioned in the vicinity of the site by insertion through a greater palatine canal of the subject.

In an embodiment, the support element is adapted to be positioned in the vicinity of the site by insertion through a nose of the subject. For some applications, the support element is adapted to be positioned in the vicinity of the site by insertion through a sphenopalatine foramen of the subject.

For some applications, the support element includes at least one mark, adapted to indicate a depth of insertion of the support element in the body. For some applications, a distance of the mark from the distal end of the support element is between about 2.5 cm and about 3 cm.

For some applications, the support element includes a stopper, adapted to prevent insertion of the support element into the body beyond a certain depth. For some applications, a distance of the stopper from the distal end of the support element is between about 2.5 cm and about 3 cm.

In an embodiment, the support element is bent at one or more locations. For some applications, an angle of a bend of the support element is between about 20 and about 40 degrees. For some applications, a distance of a bend of the support element from the distal end of the support element is between about 2 cm and about 3 cm.

There is still further provided, in accordance with an embodiment of the present invention, apparatus for facilitating a diagnosis of a condition of a subject, including:

an elongated generally rigid support element having a length of at least 1.8 cm, and having a distal end;

one or more electrodes fixed to the support element in a vicinity of the distal end thereof, and configured to be positioned in a vicinity of a site of the subject when the support element is inserted into a body of the subject, such that a portion of the support element remains outside of the body, the site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and a control unit, coupled to the support element, and adapted to:

drive the electrodes to apply an electrical current to the site, and configure the current to induce an increase in permeability of a blood-brain barrier (BBB) of the subject sufficient to increase passage of a constituent of a central nervous system (CNS) of the subject across the BBB into a systemic blood circulation of the subject.

In an embodiment, the site includes the SPG of the subject, and the electrodes are configured to be positioned in the vicinity of the SPG.

For some applications, the support element is substantially straight.

For some applications, the support element has a length between about 7 cm and about 13 cm. For some applications, a portion of the support element adapted for insertion into the body has a length of between about 2.5 cm and about 3 cm.

For some applications, the control unit is adapted to configure the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

In an embodiment, the support element is adapted to be positioned in the vicinity of the site by insertion through a roof of an oral cavity of the subject. For some applications, the support element is adapted to be positioned in the vicinity of the site by insertion through a greater palatine canal of the subject.

In an embodiment, the support element is adapted to be positioned in the vicinity of the site by insertion through a nose of the subject. For some applications, the support element is adapted to be positioned in the vicinity of the site by insertion through a sphenopalatine foramen of the subject.

In an embodiment, the support element includes at least one mark, adapted to indicate a depth of insertion of the support element in the body. For some applications, a distance of the mark from the distal end of the support element is between about 2.5 cm and about 3 cm.

In an embodiment, the support element includes a stopper, adapted to prevent insertion of the support element into the body beyond a certain depth. For some applications, a distance of the stopper from the distal end of the support element is between about 2.5 cm and about 3 cm.

For some applications, the support element is bent at one or more locations. For some applications, an angle of a bend of the support element is between about 20 and about 40 degrees. For some applications, a distance of a bend of the support element from the distal end of the support element is between about 2 cm and about 3 cm.

There is also provided, in accordance with an embodiment of the present invention, apparatus for facilitating a diagnosis of a condition of a subject, including:

a coil, adapted to be positioned in a vicinity of a site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and a control unit, adapted to drive the coil to generate a magnetic field in the vicinity of the site capable of inducing an increase in permeability of a blood-brain barrier (BBB) of the subject sufficient to increase passage of a diagnostic agent across the BBB into a central nervous system (CNS) of the subject.

In an embodiment, the site includes the SPG of the subject, and the coil is adapted to be positioned in the vicinity of the SPG.

For some applications, the control unit is adapted to generate the magnetic field with a strength sufficient to stimulate the site, and insufficient to substantially stimulate brain tissue of the subject.

For some applications, the apparatus includes a cooling element, adapted to prevent excessive heating of the coil.

For some applications, the coil includes between about 4 and about 30 loops of wire.

In an embodiment, the coil is adapted to be inserted into a nasal cavity of the subject. For some applications, the coil is substantially figure-eight-shaped. Alternatively, the coil is substantially 4-leaf-shaped. Further alternatively, the coil is substantially circular. For some applications, the coil has a diameter of between about 3 mm and about 12 mm.

In an embodiment, the coil is adapted to be placed in a vicinity of a temporomandibular joint of the subject. For some applications, the coil has a diameter of between about 3 cm and about 12 cm.

In an embodiment, the coil is adapted to be placed around at least a portion of a head of the subject. For some applications, the coil has a diameter of between about 3 cm and about 12 cm.

There is further provided, in accordance with an embodiment of the present invention, apparatus for facilitating delivery of a drug to a subject, including:

a coil, adapted to be positioned in a vicinity of a site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and a control unit, adapted to drive the coil to generate a magnetic field in the vicinity of the site capable of inducing an increase in permeability of a blood-brain barrier (BBB) of the subject sufficient to increase passage of the drug across the BBB into a central nervous system (CNS) of the subject.

In an embodiment, the site includes the SPG of the subject, and the coil is adapted to be positioned in the vicinity of the SPG.

For some applications, the control unit is adapted to generate the magnetic field with a strength sufficient to stimulate the site, and insufficient to substantially stimulate brain tissue of the subject.

For some applications, the apparatus includes a cooling element, adapted to prevent excessive heating of the coil.

For some applications, the coil includes between about 4 and about 30 loops of wire.

In an embodiment, the coil is adapted to be inserted into a nasal cavity of the subject. For some applications, the coil is substantially figure-eight-shaped. Alternatively, the coil is substantially 4-leaf-shaped. Further alternatively, the coil is substantially circular. For some applications, the coil has a diameter of between about 3 mm and about 12 mm.

In an embodiment, the coil is adapted to be placed in a vicinity of a temporomandibular joint of the subject. For some applications, the coil has a diameter of between about 3 cm and about 12 cm.

In an embodiment, the coil is adapted to be placed around at least a portion of a head of the subject. For some applications, the coil has a diameter of between about 3 cm and about 12 cm.

There is still further provided, in accordance with an embodiment of the present invention, apparatus for facilitating a diagnosis of a condition of a subject, including:

a coil, adapted to be positioned in a vicinity of a site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and a control unit, adapted to drive the coil to generate a magnetic field in the vicinity of the site capable of inducing an increase in permeability of a blood-brain barrier (BBB) of the subject sufficient to increase passage of a constituent of a central nervous system (CNS) of the subject across the BBB into a systemic blood circulation of the subject.

In an embodiment, the site includes the SPG of the subject, and the coil is adapted to be positioned in the vicinity of the SPG.

For some applications, the control unit is adapted to generate the magnetic field with a strength sufficient to stimulate the site, and insufficient to substantially stimulate brain tissue of the subject.

For some applications, the apparatus includes a cooling element, adapted to prevent excessive heating of the coil.

For some applications, the coil includes between about 4 and about 30 loops of wire.

In an embodiment, the coil is adapted to be inserted into a nasal cavity of the subject. For some applications, the coil is substantially figure-eight-shaped. Alternatively, the coil is substantially 4-leaf-shaped. Alternatively, the coil is substantially circular. For some applications, the coil has a diameter of between about 3 mm and about 12 mm.

In an embodiment, the coil is adapted to be placed in a vicinity of a temporomandibular joint of the subject. For some applications, the coil has a diameter of between about 3 cm and about 12 cm.

In an embodiment, the coil is adapted to be placed around at least a portion of a head of the subject. For some applications, the coil has a diameter of between about 3 cm and about 12 cm.

There is additionally provided, in accordance with an embodiment of the present invention, apparatus for application to a subject, including:

an elongated support element having a length of between about 1.8 cm and about 4 cm, and having a proximal end and a distal end;

one or more electrodes fixed to the support element in a vicinity of the distal end thereof; and a control unit, coupled to the support element in a vicinity of the proximal end thereof, and including a battery, the control unit adapted to:

drive the electrodes to apply an electrical current to tissue of the subject, and configure the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

In an embodiment, the tissue is selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject, and the control unit is adapted to drive the electrodes to apply the current to the selected tissue.

In an embodiment, the apparatus includes an oral appliance, coupled to the support element, and shaped so as to define a surface that fits closely to a roof of an oral cavity.

For some applications, the support element has a length of between about 1.8 cm and about 3 cm. For some applications, the control unit has a volume, including the battery, of less than about 3 cm$^3$.

For some applications, the control unit is adapted to apply the current having on periods of between about 60 seconds and about 105 seconds, and off periods of between about 30 seconds and 90 seconds. For some applications, the control unit is adapted to apply the current having on periods of about 90 seconds, and off periods of about 60 seconds.

There is yet additionally provided, in accordance with an embodiment of the present invention, apparatus for application to a subject, including:

an elongated support element having a length of between about 1.8 cm and about 4 cm, and having a proximal end and a distal end;

one or more electrodes fixed to the support element in a vicinity of the distal end thereof;

a receiver, fixed to the support element in a vicinity of the proximal end thereof; and a control unit, adapted to be coupled to the receiver, and adapted to:

drive the electrodes to apply an electrical current to tissue of the subject, and configure the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

In an embodiment, the tissue is selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject, and the control unit is adapted to drive the electrodes to apply the current to the selected tissue.

For some applications, the support element has a length of between about 1.8 cm and about 3 cm.

For some applications, the receiver includes an electrical contact site, and the control unit is adapted to be coupled to the receiver by being brought into physical contact with the electrical contact site.

For some applications, the receiver includes a transducer, and the control unit includes a wireless transmitter, which is adapted to couple the control unit to the receiver via wireless electromagnetic communication with the transducer. For some applications, the transducer includes a coil. For some applications, the control unit is adapted to be positioned outside of a head of the subject during operation.

For some applications, the control unit is adapted to be positioned inside an oral cavity of the subject. For some applications, the apparatus includes an oral appliance, adapted to be-fixed to the control unit, and shaped so as to define a surface that fits closely to a roof of the oral cavity.

For some applications, the receiver has a volume of less than about 0.8 cm$^3$. For some applications, the receiver has a volume of less than about 0.15 cm$^3$.

For some applications, the control unit is adapted to apply the current having on periods of between about 60 seconds and about 105 seconds, and off periods of between about 30 seconds and 90 seconds. For some applications, the control unit is adapted to apply the current having on periods of about 90 seconds, and off periods of about 60 seconds.

There is also provided, in accordance with an embodiment of the present invention, apparatus for application to a subject, including:

an ENT endoscope, having at least one working channel;

at least one electrode, adapted to be passed through the working channel, and positioned in a vicinity of tissue of the subject; and a control unit, coupled to the electrode, and adapted to drive the electrode to apply a non-ablating electrical signal to the tissue.

For some applications, the control unit is adapted to configure the signal to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

In an embodiment, the tissue is selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject, and the control unit is adapted to drive the electrode to apply the signal to the selected tissue.

For some applications, the ENT endoscope includes a side-viewing scope having a viewing angle of between about 30 and about 120 degrees relative to a longitudinal axis of the endoscope. For some applications, the electrode is adapted to be positioned so as to be viewable by the side-viewing scope.

There is further provided, in accordance with an embodiment of the present invention, apparatus for modifying a property of a brain of a subject, including:

at least one electrode, adapted to be positioned in a vicinity of a mucous membrane of a palate of an oral cavity of the subject; and a control unit, adapted to drive the electrode to apply an electrical current to the mucous membrane, and to configure the current to be capable of inducing an increase in permeability of a blood-brain barrier (BBB) of the subject.

For some applications, the control unit is adapted to configure the current to have a magnitude sufficient to activate a sphenopalatine ganglion (SPG) of the subject via nerve fibers in physical contact with the mucous membrane.

For some applications, the control unit is adapted to configure the current to increase the permeability of the BBB to a magnitude sufficient to treat a condition of the subject. Alternatively or additionally, the control unit is adapted to configure the current to increase the permeability of the BBB to a magnitude sufficient to perform a diagnosis of a condition of the subject.

There is still further provided, in accordance with an embodiment of the present invention, apparatus for modifying a property of a brain of a subject, including:

at least one electrode, adapted to be positioned in a vicinity of a mucous membrane of a palate of an oral cavity of the subject; and a control unit, adapted to drive the electrode to apply an electrical current to the mucous membrane, and to configure the current to be capable of inducing an increase in cerebral blood flow (CBF) of the subject.

For some applications, the control unit is adapted to configure the current to have a magnitude sufficient to activate a sphenopalatine ganglion (SPG) of the subject via nerve fibers in physical contact with the mucous membrane.

For some applications, the control unit is adapted to configure the current to increase the CBF to a magnitude sufficient to treat a condition of the subject.

There is additionally provided, in accordance with an embodiment of the present invention, a method for treating a subject, including:

positioning at least one electrode at at least one site of the subject for less than about 3 hours, the site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject;

applying an electrical current to the site of the subject; and
configuring the current to increase cerebral blood flow (CBF) of the subject, so as to treat a condition of the subject.

For some applications, positioning the electrode includes:
applying the electrical current to the site;
observing one or more physiological responses of the subject to the current; and
verifying desired placement of the electrode responsive to the observation.

There is yet additionally provided, in accordance with an embodiment of the present invention, a method for treating a complication of subarachnoid hemorrhage (SAH) of a subject, including stimulating at least one site of the subject in conjunction with treating the SAH, the site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject.

For some applications, stimulating the site includes stimulating the site prior to treating the SAH. Alternatively or additionally, stimulating the site includes stimulating the site while treating the SAH. Further alternatively or additionally, stimulating the site includes stimulating the site after treating the SAH.

There is also provided, in accordance with an embodiment of the present invention, a method for treating a condition of a subject, including:

selecting a site from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and generating a magnetic field in the vicinity of the site capable of inducing an increase in cerebral flood flow of the subject, so as to treat the condition.

There is further provided, in accordance with an embodiment of the present invention, a method for treating a condition of a subject, including:

selecting a site from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and generating a magnetic field in the vicinity of the site capable of inducing an increase in permeability of a blood-brain barrier (BBB) of the subject, so as to treat the condition.

There is still further provided, in accordance with an embodiment of the present invention, a method for facilitating a diagnosis of a condition of a subject, including:

positioning at least one electrode at at least one site of the subject for less than about 3 hours, the site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject;

applying an electrical current to the site of the subject; and configuring the current to induce an increase in permeability of a blood-brain barrier (BBB) of the subject sufficient to increase passage of a diagnostic agent across the BBB into a central nervous system (CNS) of the subject.

For some applications, positioning the electrode includes:
applying the electrical current to the site;
observing one or more physiological responses of the subject to the current; and
verifying desired placement of the electrode responsive to the observation.

There is additionally provided, in accordance with an embodiment of the present invention, a method for facilitating delivery of a drug to a subject, including:

positioning at least one electrode at at least one site of the subject for less than about 3 hours, the site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject;

applying an electrical current to the site of the subject; and configuring the current to induce an increase in permeability of a blood-brain barrier (BBB) of the subject sufficient to increase passage of the drug across the BBB into a central nervous system (CNS) of the subject.

In an embodiment, the method includes administering the drug to a body of the subject, in conjunction with applying the current.

For some applications, positioning the electrode includes:
applying the electrical current to the site;
observing one or more physiological responses of the subject to the current; and
verifying desired placement of the electrode responsive to the observation.

There is yet additionally provided, in accordance with an embodiment of the present invention, a method for facilitating a diagnosis of a condition of a subject, including:

positioning at least one electrode at at least one site of the subject for less than about 3 hours, the site selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and applying an electrical current to the site of the subject; and configuring the current to induce an increase in permeability of a blood-brain barrier (BBB) of the subject sufficient to increase passage of a constituent of a central nervous system (CNS) of the subject across the BBB into a systemic blood circulation of the subject.

For some applications, the method includes measuring a concentration of the constituent in the systemic blood circulation.

For some applications, positioning the electrode includes:
applying the electrical current to the site;
observing one or more physiological responses of the subject to the current; and
verifying desired placement of the electrode responsive to the observation.

There is also provided, in accordance with an embodiment of the present invention, a method for facilitating a diagnosis of a condition of a subject, including:

selecting a site from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and generating a magnetic field in the vicinity of the site capable of inducing an increase in permeability of a blood-brain barrier (BBB) of the subject sufficient to increase passage of a diagnostic agent across the BBB into a central nervous system (CNS) of the subject.

There is further provided, in accordance with an embodiment of the present invention, a method for facilitating delivery of a drug to a subject, including:

selecting a site from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and generating a magnetic field in the vicinity of the site capable of inducing an increase in permeability of a blood-brain barrier (BBB) of the subject sufficient to increase passage of the drug across the BBB into a central nervous system (CNS) of the subject.

In an embodiment, the method includes administering the drug to a body of the subject, in conjunction with generating the magnetic field.

There is still further provided, in accordance with an embodiment of the present invention, a method for facilitating a diagnosis of a condition of a subject, including:

selecting a site from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and generating a magnetic field in the vicinity of the site capable of inducing an increase in permeability of a blood-brain barrier (BBB) of the subject sufficient to increase passage of a constituent of a central nervous system (CNS) of the subject across the BBB into a systemic blood circulation of the subject.

For some applications, the method includes measuring a concentration of the constituent in the systemic blood circulation.

There is additionally provided, in accordance with an embodiment of the present invention, a method including:

inserting an elongated support element into a body of a subject, the element having a length of between about 1.8 cm and about 4 cm, and having a distal end;

applying, from the distal end, an electrical current to tissue of the subject; and configuring the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

There is yet additionally provided, in accordance with an embodiment of the present invention, a method including:

inserting an elongated support element into a body of a subject, the element having a length of between about 1.8 cm and about 4 cm, and having a distal end;

receiving electromagnetic energy;

using the electromagnetic energy, applying an electrical current to tissue of the subject; and configuring the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

There is still additionally provided, in accordance with an embodiment of the present invention, a method including:

inserting an ENT endoscope, having at least one working channel, into a body of a subject;

passing at least one electrode through the working channel;

positioning the electrode in a vicinity of tissue of the subject; and driving the electrode to apply a non-ablating electrical signal to the tissue.

There is further provided, in accordance with an embodiment of the present invention, a method for modifying a property of a brain of a subject, including applying to a branch of a cranial nerve V of the subject an electrical current configured to affect physiological activity of a sphenopalatine ganglion (SPG) of the subject at a level sufficient to induce an increase in permeability of a blood-brain barrier (BBB) of the subject.

There is still further provided, in accordance with an embodiment of the present invention, a method for modifying a property of a brain of a subject, including applying to a branch of cranial nerve V of the subject an electrical current configured to affect physiological activity of a sphenopalatine ganglion (SPG) of the subject at a level sufficient to induce an increase in cerebral blood flow (CBF) of the subject.

There is also provided, in accordance with an embodiment of the present invention, a method for modifying a property of a brain of a subject, including generating a magnetic field in the vicinity of a branch of a cranial nerve V of the subject configured to affect physiological activity of a sphenopalatine ganglion (SPG) of the subject at a level sufficient to induce an increase in permeability of a blood-brain barrier (BBB) of the subject.

There is further provided, in accordance with an embodiment of the present invention, a method for modifying a property of a brain of a subject, including generating a magnetic field in the vicinity of a branch of a cranial nerve V of the subject configured to affect physiological activity of a sphenopalatine ganglion (SPG) of the subject at a level sufficient to induce an increase in cerebral blood flow (CBF) of the subject.

There is still further provided, in accordance with an embodiment of the present invention, a method for application to a subject, including:

selecting a site from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject; and positioning a distal region of an elongated stimulator in a vicinity of the site;

generating a neuroexcitatory electrical current at the distal region;

confirming accurate positioning of the distal region, responsively to an observation of an expected physiological response to the neuroexcitatory current; and in response to confirming the positioning, applying, from the distal region, a chemical substance to the vicinity of the site.

There is additionally provided, in accordance with an embodiment of the present invention, a method for modifying a property of a brain of a subject, including applying an electrical current to a mucous membrane of a palate of an oral cavity of the subject, the current capable of inducing an increase in permeability of a blood-brain barrier (BBB) of the subject.

In an embodiment, the method includes administering a sedative to the subject in conjunction with applying the current. Alternatively or additionally, the method includes administering an anesthetic to the subject in conjunction with applying the current.

In an embodiment, the method includes performing a diagnostic activity with respect to a condition of the subject, in conjunction with the increase in permeability of the BBB.

There is yet additionally provided, in accordance with an embodiment of the present invention, a method for modifying a property of a brain of a subject, including applying an electrical current to a mucous membrane of a palate of an oral cavity of the subject, the current capable of inducing an increase in cerebral blood flow (CBF) of the subject.

The present invention will be more fully understood from the following detailed description of the embodiments thereof, taken together with the drawings, in which:

BRIEF DESCRIPTION OF THE DRAWINGS

FIGS. 16A–D, 17A–D, and 18A–D are graphs showing in vivo experimental results, measured in accordance with an embodiment of the present invention.

DETAILED DESCRIPTION OF THE INVENTION

Figure 1A:
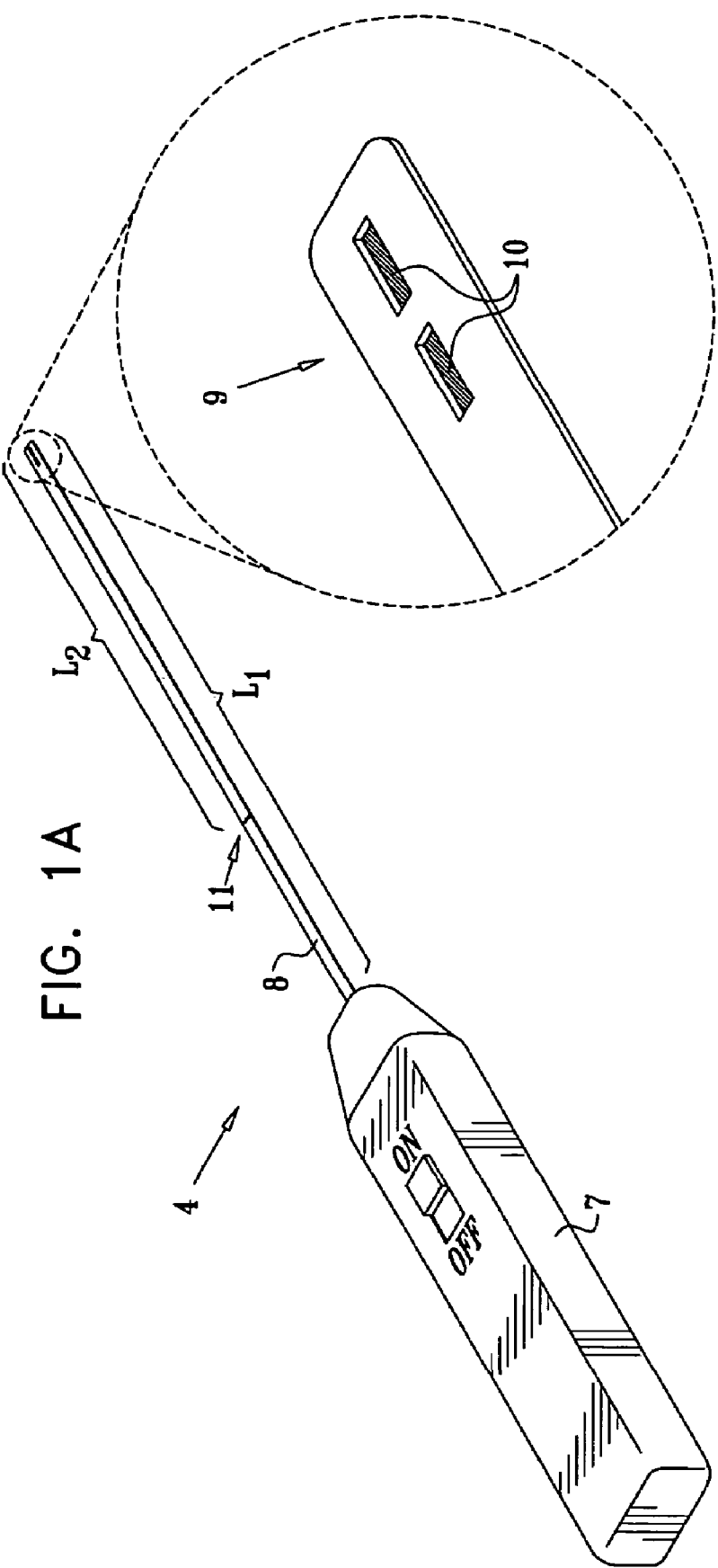
FIGS. 1A and 1B are schematic pictorial views of an insertable stimulator for stimulation of a modulation target site, in accordance with embodiments of the present invention.
Figure 1B:
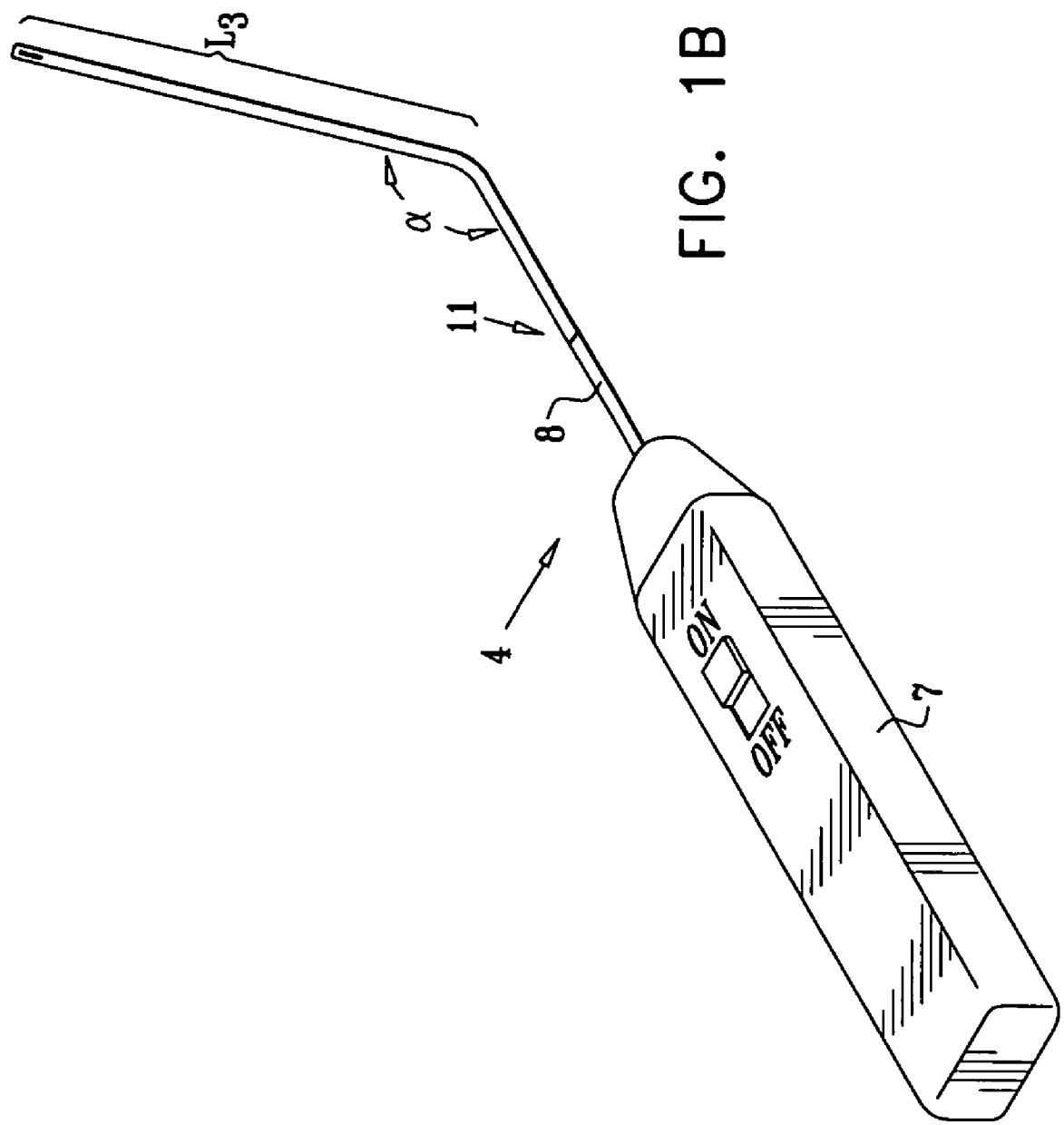

FIGS. 1A and 1B are schematic pictorial views of an electrical stimulator 4, for stimulation of a sphenopalatine ganglion (SPG) system, as defined hereinabove, and/or at least one other appropriate "modulation target site" (MTS), as defined hereinabove, such as an SPG 6 (FIGS. 2A and 2B), in accordance with embodiments of the present invention. Electrical stimulator 4 comprises a control handle 7 and, typically, a substantially rigid support element 8. For some embodiments, support element 8 is not rigid. A distal end 9 of support element 8 typically comprises one or more electrodes 10. It is noted that although control handle 7 is shown in FIG. 1A as being of generally the same length as support element 8, for some embodiments, the control handle is considerably shorter. For some applications, electrodes 10 are recessed within support element 8, as shown in the figure, while for other applications the electrodes are flush with the surface of the support element, or protrude therefrom.

Support element 8 typically comprises a mark 11 that indicates the point at which the support element has been sufficiently inserted into a canal of the nasal cavity, as described hereinbelow with reference to FIGS. 2A and 2B. Alternatively or additionally, support element 8 comprises a stopper (not shown) in a vicinity of mark 11, that mechanically prevents further insertion of the support element into the canal.

For some applications, such as insertion via the greater palatine canal in the roof of the oral cavity, support element 8 is substantially straight, as shown in FIG. 1A. For these applications, support element 8 typically has a total length $L_1$ of between about 7 cm and about 13 cm, and the distal portion of the support element that is inserted into the canal typically has a length $L_2$ of between about 2.5 and about 3 cm, such as about 2.6 cm. For some patients, values of $L_1$ and/or $L_2$ outside of this range are used. For other applications, such as insertion via the nose, support element 8 is typically bent at one or more points, such as shown in FIG. 1B. It is noted that for some applications, insertion via the mouth or via the nose may be accomplished via a straight, bent, or jointed support element. For example, support element 8 may be bent at an angle a of between about 20 degrees and about 40 degrees, such as about 30 degrees at a point positioned a distance $L_3$ of between about 2 cm and about 3 cm from the distal end of the support element.

Figure 2A:
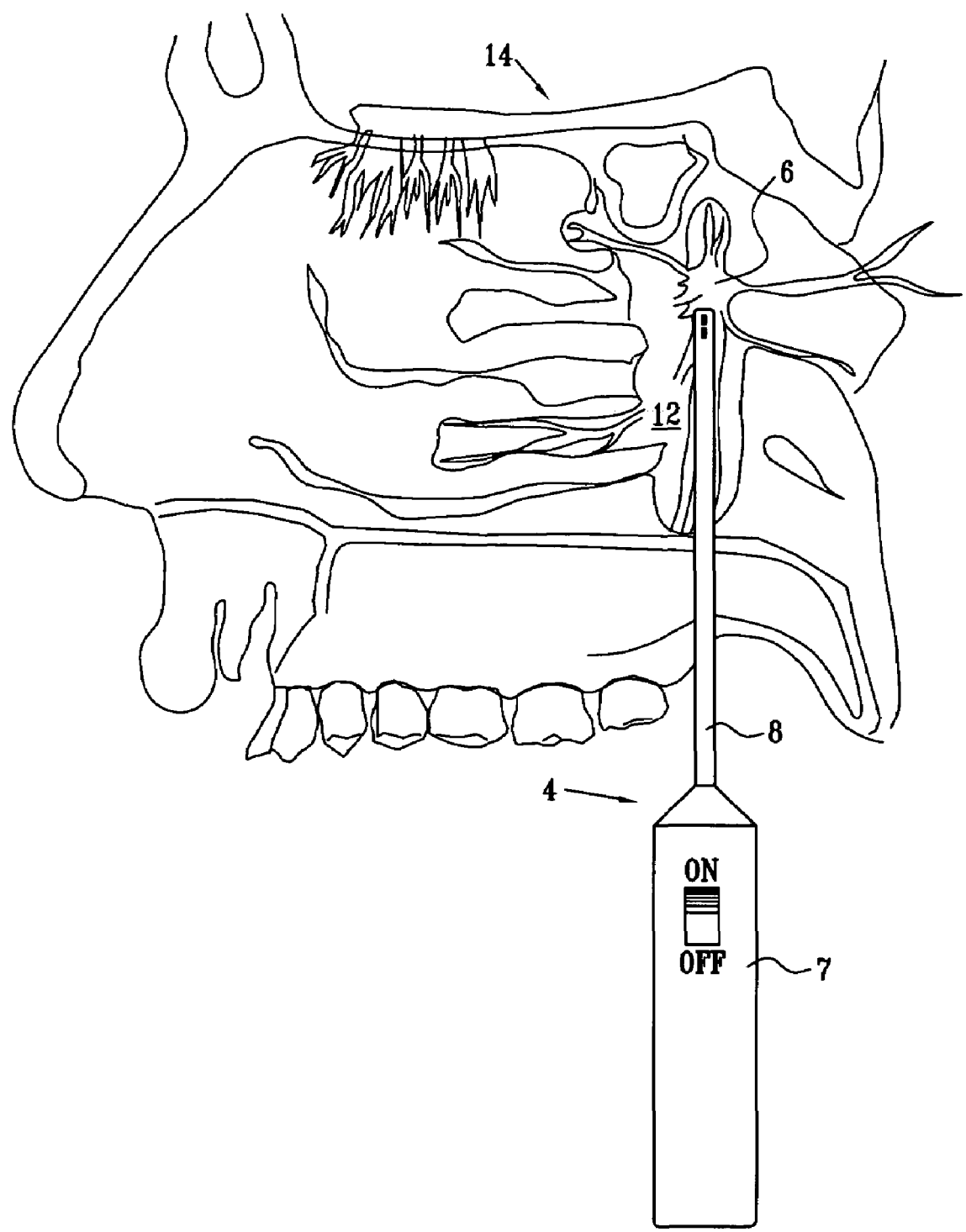
FIGS. 2A and 2B are schematic pictorial views of a support element of the stimulator of FIGS. 1A and 1B inserted into a human nasal cavity, in accordance with embodiments of the present invention.
Figure 2B:
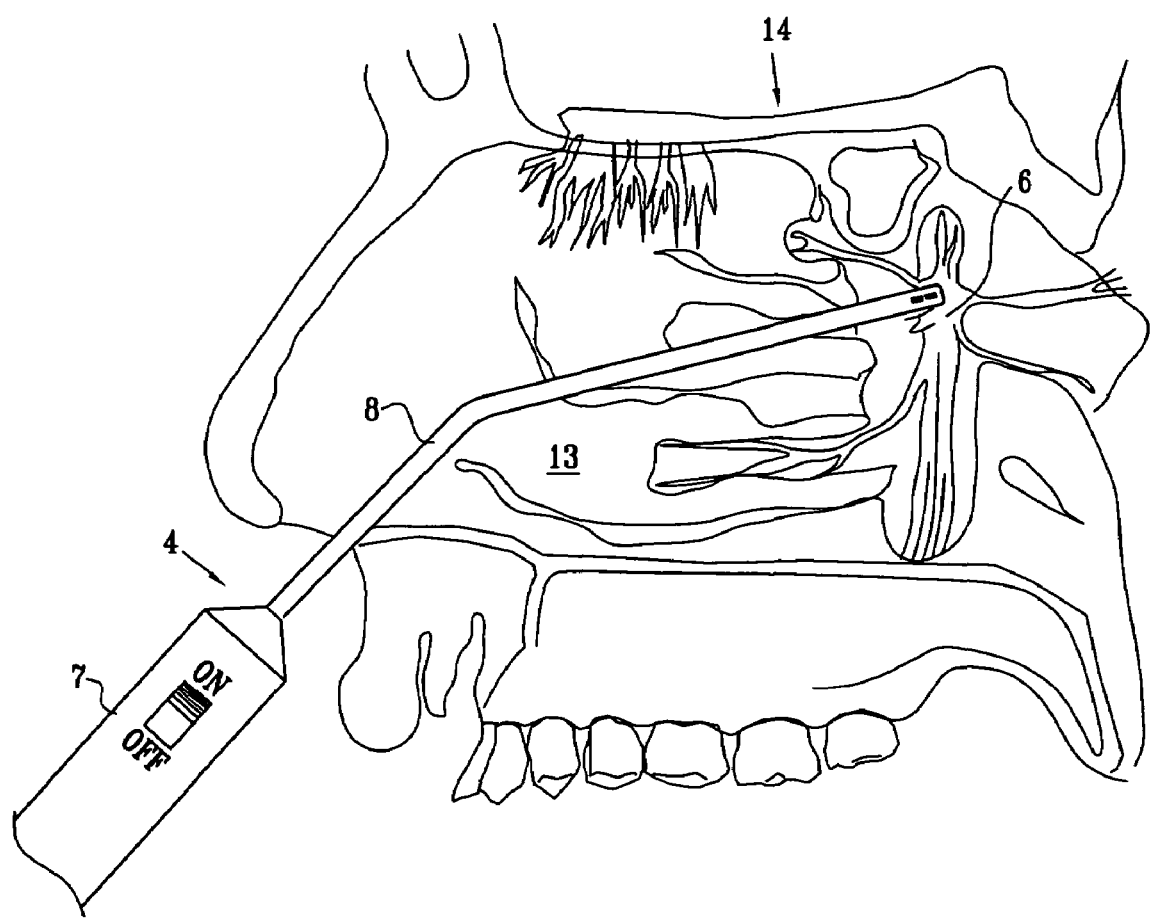

Reference is now made to FIGS. 2A and 2B, which are schematic pictorial views of support element 8 inserted into a human nasal cavity 14, in accordance with embodiments of the present invention. In FIG. 2A, support element 8 is shown inserted into a vicinity of SPG 6 via the roof of the oral cavity, through a greater palatine canal 12. In FIG. 2B, support element 8 is shown inserted into a vicinity of SPG 6 via the nose, through a sphenopalatine foramen canal 13.

Support element 8 and electrodes 10 are typically adapted to be rapidly delivered to a desired point within nasal cavity 14, such as for treatment of an acute and/or emergency medical condition of a subject. Support element 8 and electrodes 10 are typically not adapted to be implanted at the site for long-term, chronic stimulation, but rather to be positioned in place on a short-term basis (e.g., (a) for several seconds or minutes, (b) for less than about three hours, or, (c) for some applications, for less than about three hours per day or for about a week), until completion of the treatment session. As appropriate, the placement process may be facilitated by fluoroscopy, x-ray guidance, standard endoscopy, fine endoscopic surgery (FES) techniques or by any other effective guidance method known in the art, or by combinations of the aforementioned. It is noted, however, that these facilitation techniques are not necessarily utilized, and that in many acute situations, an emergency medical technician is able to rapidly guide support element 8 and electrodes 10 to the target using only basic techniques.

For some applications, the patient's body temperature (see FIGS. 4A and 4B) and/or cerebral blood flow (CBF) is measured concurrently with insertion. The CBF may be measured with, for example, a laser Doppler unit positioned at the subject's forehead or transcranial Doppler measurements. Verification of proper placement of electrodes 10 onto the appropriate neural structure may be performed by activating electrical stimulator 4, and generally simultaneously monitoring CBF. Alternatively or additionally, the dilation of blood vessels near the surface of one or both of the patient's eyes is visually monitored. The onset of such dilation is easily observed, and indicates that the SPG is being stimulated. Further alternatively or additionally, lacrimation and/or nasal discharge are used as an indication of SPG stimulation.

It is to be understood that support element 8 (FIGS. 1A and 1B) comprises one or more electrodes 10, e.g., two electrodes, or an array of microelectrodes. For some applications in which support element 8 comprises a metal outer surface, such that the support element can function as an electrode, a single electrode 10 is used, operating in a monopolar mode. Regardless of the total number of electrodes in use, typically only a single or a double electrode extends to SPG 6.

Each of electrodes 10 typically comprises a suitable conductive material, for example, a physiologically-acceptable material such as silver, iridium, platinum, a platinum iridium alloy, titanium, nitinol, or a nickel-chrome alloy. For some applications, one or more of the electrodes have surface areas ranging from about 1 mm$^2$ to about 3 mm$^2$.

Each electrode is typically insulated with a physiologically-acceptable material such as polyethylene, polyurethane, or a co-polymer of either of these. The electrodes are typically spiral in shape, for better contact, and may have a hook shaped distal end for hooking into or near the SPG. Alternatively or additionally, the electrodes may comprise simple wire electrodes, spring-loaded "crocodile" electrodes, or adhesive probes, as appropriate. Further alternatively or additionally, the electrodes may comprise needle-like elements, similar to standard EMG stimulation electrodes.

In an embodiment of the invention, electrodes 10 comprise a substantially smooth surface, except that the distal end of each such electrode is configured or treated to have a large surface area. For example, the distal tip may be porous platinized. Alternatively or additionally, at least the tips of electrodes 10, and/or support element 8 includes a coating comprising an anti-inflammatory drug, such as beclomethasone sodium phosphate or beclomethasone phosphate. Alternatively, such an anti-inflammatory drug is injected or otherwise applied.

Figure 3:
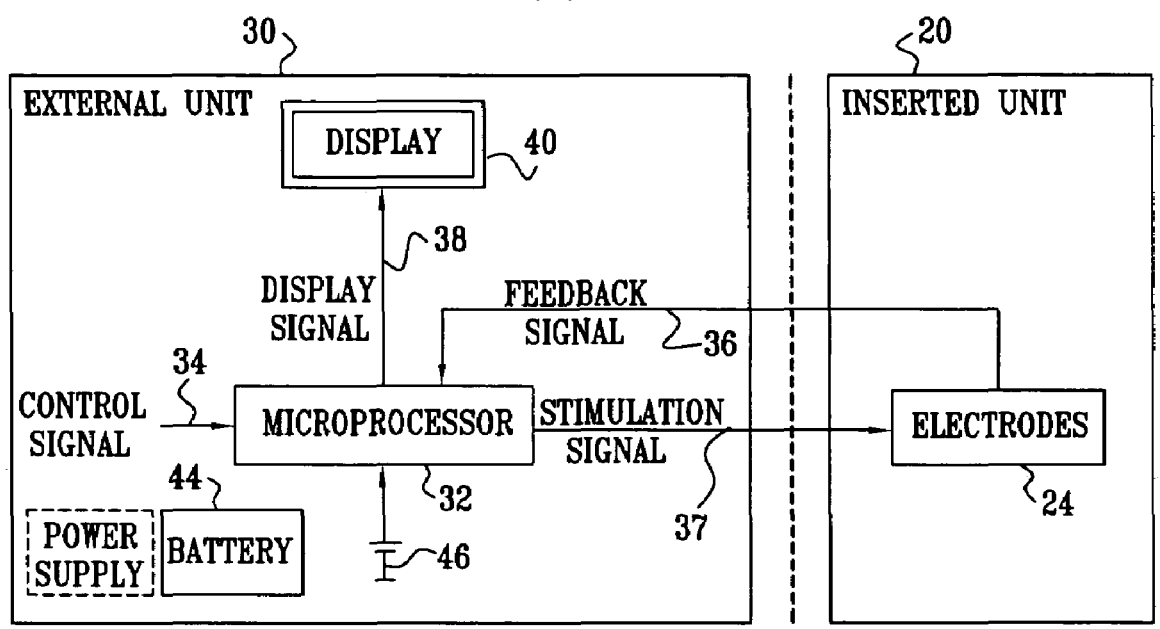
FIG. 3 is a schematic block diagram illustrating circuitry for use with the stimulator shown in FIGS. 1A and 1B, in accordance with an embodiment of the present invention.

FIG. 3 is a schematic block diagram illustrating circuitry comprising an inserted unit 20 and an external unit 30, for use with stimulator 4 (FIG. 1A), in accordance with an embodiment of the present invention. Inserted unit 20 typically comprises one or more sensing or signal application electrodes 24. External unit 30 typically comprises a microprocessor 32 which receives an external control signal 34 (e.g., from a physician or from the patient), and a feedback signal 36 measured by one or more of electrodes 24. Control signal 34 may include, for example, operational parameters such as a schedule of operation, patient parameters such as the patient's weight, or signal parameters, such as desired frequencies or amplitudes of a signal to be applied to an MTS. If appropriate, control signal 34 can comprise an emergency override signal, entered by the patient or a healthcare provider to terminate stimulation or to modify it in accordance with a predetermined program. Microprocessor 32, in turn, typically (but not necessarily) processes control signal 34 and feedback signal 36 so as to determine one or more parameters of the electric current to be applied through electrodes 24. Responsive to this determination, microprocessor 32 typically generates a stimulation signal 37 having a desired current or voltage to be applied by electrodes 24 to an MTS, such as SPG 6, or other tissue. The configuration of circuitry in units 20 or 30 may determine the intensity, frequency, shape, monophasic or biphasic mode, or DC offset of the signal (e.g., a series of pulses) applied to designated tissue. In an embodiment, control handle 7 comprises the circuitry of external unit 30, and support element 8 comprises the circuitry of inserted unit 20.

Power for microprocessor 32 is typically supplied by a battery 44 or, optionally, another DC power supply. Grounding is provided by battery 44 or a separate ground 46. If appropriate, microprocessor 32 generates a display signal 38 that drives a display block 40 of external unit 30. Typically, but not necessarily, the display is activated to show feedback data received from electrodes 24, or to provide a user interface for the external unit.

For some applications, the waveform applied by one or more of electrodes 10 to designated tissue of an MTS (e.g., the SPG) comprises a waveform with an exponential decay, a ramp up or down, a square wave, a sinusoid, a saw tooth, a DC component, or any other shape known in the art to be suitable for application to tissue. Alternatively or additionally, the waveform comprises one or more bursts of short shaped or square pulses—each pulse typically less than about 1 ms in duration. Generally, appropriate waveforms and parameters thereof are determined during an initial test period of electrical stimulator 4. For some applications, the waveform is dynamically updated according to measured physiological parameters, measured during a period in which electrical stimulator 4 is stimulating an MTS, and/or during a non-activation (i.e., standby) period.

Figure 4A:
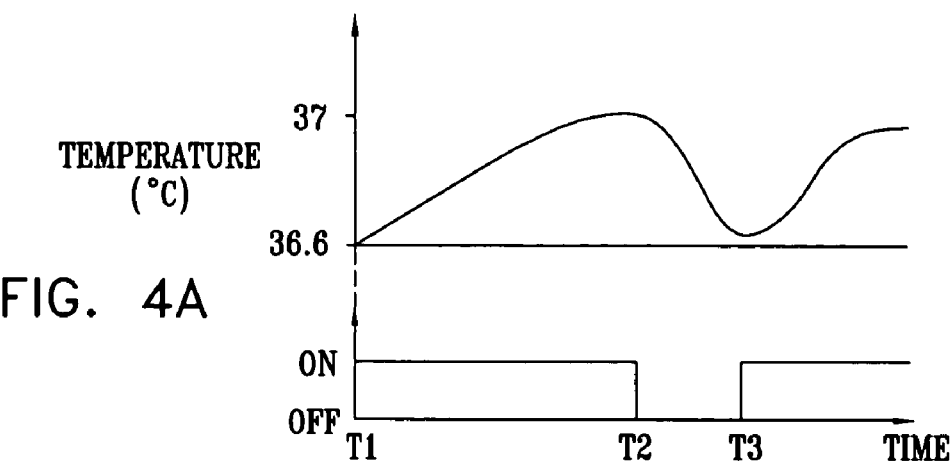
FIGS. 4A and 4B are schematic illustrations depicting different modes of operation of stimulators such as those shown in FIGS. 1A and 1B, in accordance with embodiments of the present invention.

FIG. 4A is a graph schematically illustrating a mode of operation of one or more of the devices shown in FIGS. 1–3, in accordance with an embodiment of the present invention. Typically, the effect of the applied stimulation is monitored by means of a temperature transducer at an MTS-affected organ (e.g., the forehead) or elsewhere in the head, e.g., in the nasal cavity. As shown in FIG. 4A for a step (ON/OFF) mode of stimulation, stimulation of an MTS or related tissue is initiated at a time T1, and this is reflected by a measurable rise in temperature (due to increased blood flow). Once the temperature rises to a predetermined or dynamically-varying threshold (e.g., 37° C.), stimulation is terminated (time T2), responsive to which the temperature falls. As appropriate, when the temperature drops to a designated or dynamically-determined point, the stimulation is reinitiated (time T3). Typically, suitable temperatures or other physiological parameters are determined for each patient so as to provide the optimal treatment. If appropriate, control instructions may also be received from the operator, which may be either the patient himself, or a healthcare worker.

Figure 4B:
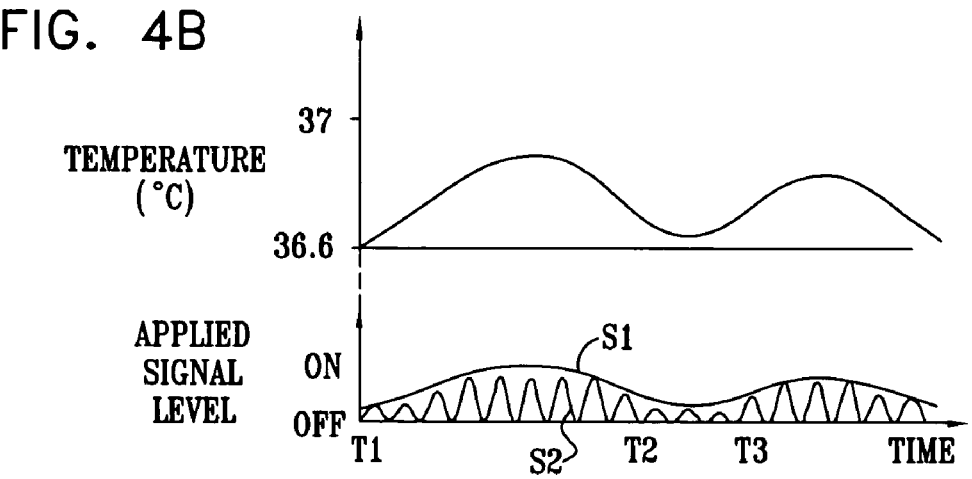

FIG. 4B is a graph schematically illustrating a mode of operation of one or more of the devices shown in FIGS. 1–3, in accordance with another embodiment of the present invention. In this embodiment, the amplitude of the waveform applied to an MTS is varied among a continuous set of values (S1), or a discrete set of values (S2), responsive to the measured temperature, in order to achieve the desired performance. It will be appreciated that other feedback parameters measured in the head (e.g., intraocular pressure, intracranial pressure and/or CBF), as well as measured systemic parameters (e.g., heart rate) and subjective patient inputs may be used in conjunction with or separately from temperature measurements, in order to achieve generally optimal performance of the implanted apparatus.

Figure 5:
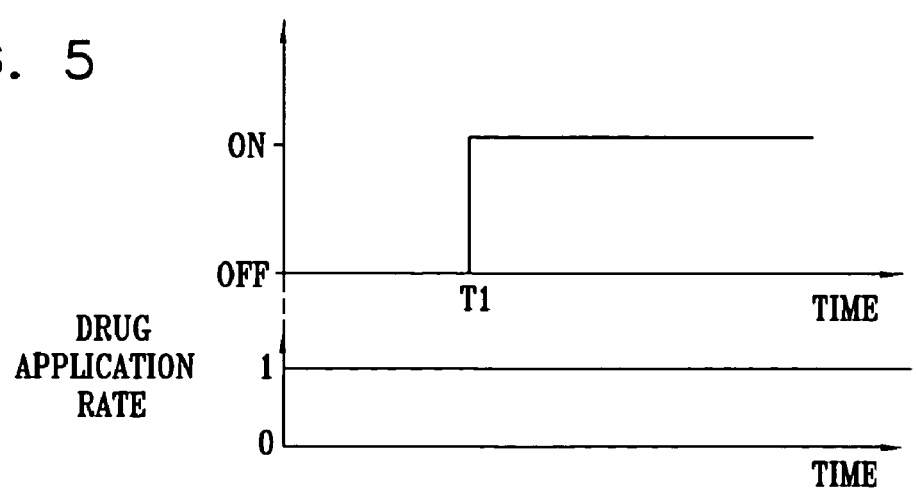
FIG. 5 is a schematic illustration of a mode of operation of the stimulators shown in FIGS. 1A and 1B, in accordance with an embodiment of the present invention.

FIG. 5 is a graph schematically illustrating a mode of operation of one or more of the devices shown in FIGS. 1–3, in accordance with an embodiment of the present invention. In this embodiment, a diagnostic agent is administered to the patient, e.g., intravenously, prior to the initiation of electrical, chemical, magnetic, electromagnetic and/or mechanical stimulation of an MTS at time T1. Advantageously, this prior generation of heightened concentrations of the diagnostic agent in the blood tends to provide relatively rapid transfer of the diagnostic agent across the BBB and into the central nervous system (CNS), without unnecessarily prolonging the enhanced permeability of the BBB while waiting for the blood concentration of the diagnostic agent to reach an appropriate level. Alternatively, for some applications it is desirable to give a single bolus injection of the diagnostic agent shortly before or after initiation of stimulation of an MTS. Typically, combined administration and stimulation schedules are determined by the patient's physician based on the pharmacokinetic properties of each diagnostic agent targeted at the CNS.

Figure 6:
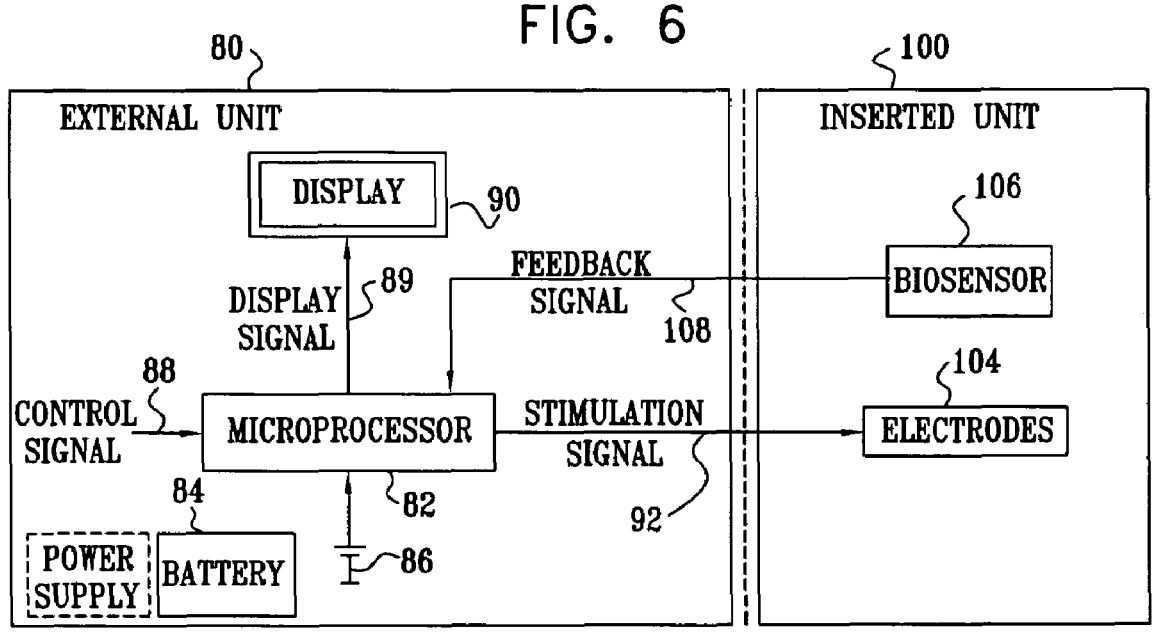
FIG. 6 is a schematic block diagram illustrating circuitry for use with the stimulator shown in FIGS. 1A and 1B, where the stimulator is driven by an external controller and energy source using a modulator and a demodulator, in accordance with an embodiment of the present invention.

FIG. 6 is a schematic block diagram showing circuitry for parasympathetic stimulation, which is particularly useful in combination with the embodiments shown in FIGS. 1A and 1B, in accordance with an embodiment of the present invention. An external unit 80 typically comprises a microprocessor 82 that is powered by a battery 84 and/or an AC power source. Microprocessor 82 is grounded through battery 84 or through an optional ground 86.

In a typical mode of operation, an external control signal 88 is input to microprocessor 82, along with a feedback signal 108 from one or more biosensors 106, which are typically disposed in a vicinity of an inserted unit 100 or elsewhere on or in the patient's body. Responsive to signals 88 and 108, microprocessor 82 typically generates a display signal 89 which drives a display 90, as described hereinabove. In addition, microprocessor 82 typically processes external control signal 88 and feedback signal 108, to determine parameters of a stimulation signal 92 which is applied by at least one electrode 104 to an MTS or to other tissue, as appropriate.

Typically, biosensor 106 comprises implantable or external medical apparatus including, for example, one or more of the following:
  a blood flow sensor,
  a temperature sensor,
  a chemical sensor,
  an ultrasound sensor,
  transcranial Doppler (TCD) apparatus,
  laser-Doppler apparatus,
  a systemic or intracranial blood pressure sensor (e.g., comprising a piezoelectric crystal or capacitive sensor fixed to a major cerebral blood vessel),
  a tissue vitality sensor, e.g., comprising laser Doppler or other optical apparatus for detecting a NAD/NADH ratio in tissue, using optical techniques known in the art for detecting the metabolic state of a tissue,
  a kinetics sensor, comprising, for example, an acceleration, velocity, or level sensor (e.g., a mercury switch), for indicating body dispositions such as a sudden change in body attitude (as in collapsing),
  an electroencephalographic (EEG) sensor comprising EEG electrodes attached to, or implanted in, the patients head, for indicating changes in neurological patterns, such as symptoms of stroke, or
  other monitors of physiological quantities suitable for carrying out the objects of this or other embodiments of the present invention.

Figures 7A, 7B:
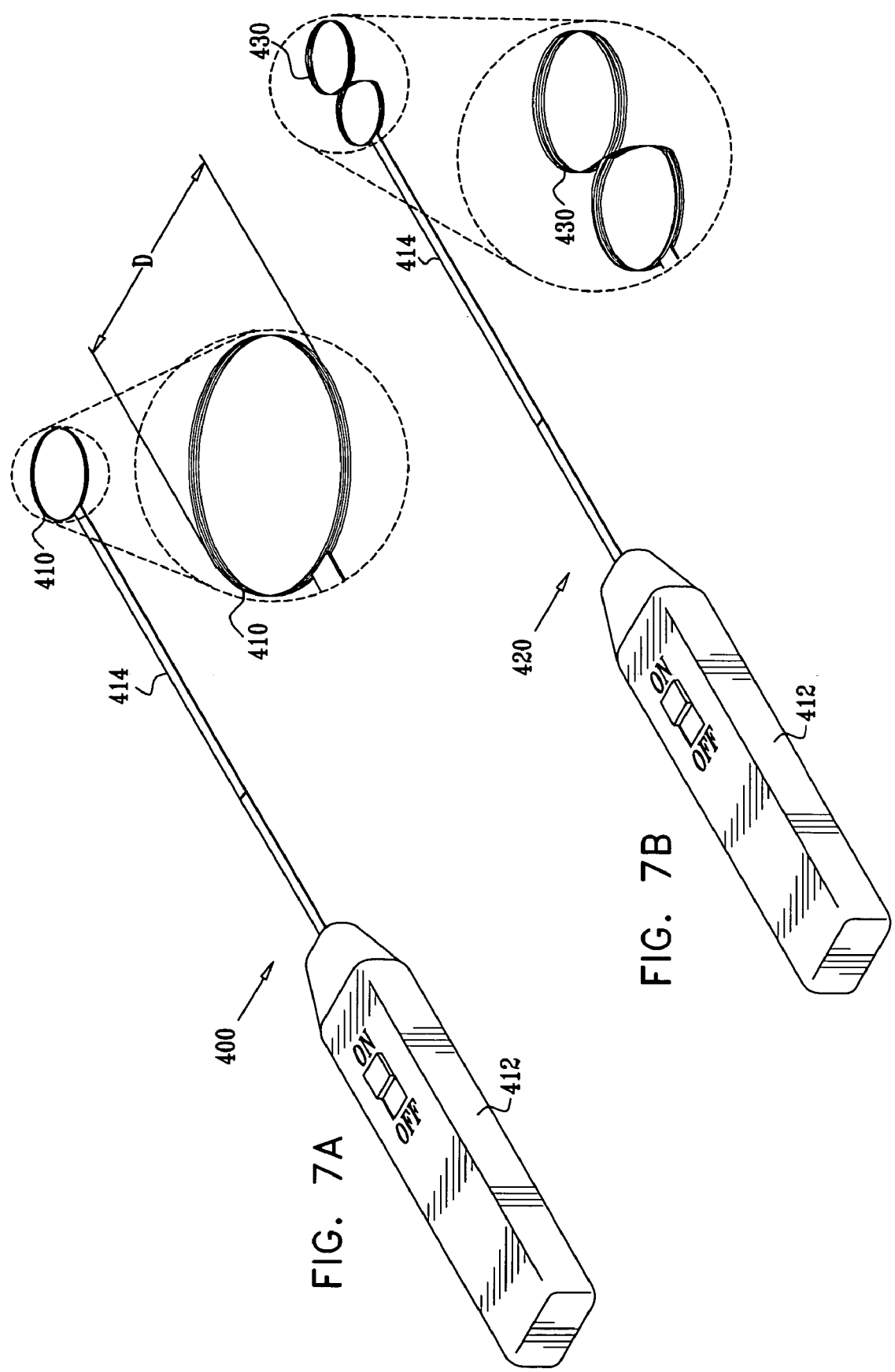
FIGS. 7A and 7B are schematic illustrations of nasal magnetic induction devices, in accordance with an embodiment of the present invention.

FIG. 7A is a schematic illustration of a nasal magnetic induction device 400, in accordance with an embodiment of the present invention. Nasal magnetic induction device 400 generates a magnetic field in the vicinity of an MTS. The magnetic field induces an electric current in the MTS, which temporarily depolarizes neurons therein, thereby electrically stimulating the MTS.

Nasal magnetic induction device 400 typically comprises a wire coil 410 adapted to be insertable into the nasal cavity, and a control unit 412 coupled to the coil. As appropriate, the coil may be compressed during insertion and expand at the target site, or it may be retracted during insertion within a supporting element 414 of device 400, and released when at the target site. Typically, coil 410 has a diameter D of between about 3 mm and about 12 mm, and comprises between about 4 and about 30 loops of wire. The wire typically has a diameter of between about 50 micrometers and about 200 micrometers. Upon activation, the control unit generates a pulsed electric current in the coil. Because of the close proximity of the coil to an MTS, e.g., an SPG, the control unit typically outputs power sufficient to stimulate the SPG but generally insufficient to substantially stimulate surrounding peripheral or brain tissue. For some applications, the nasal magnetic induction device further comprises a cooling element (e.g., a thermoelectric cooling element, a liquid cooling mechanism, or an air cooling mechanism), which is adapted to prevent excessive heating of the coil.

FIG. 7B is a schematic illustration of a nasal magnetic induction device 420, in accordance with an embodiment of the present invention. Nasal magnetic induction device 420 is similar to nasal magnetic induction device 400, described hereinabove with reference to FIG. 7A, except that nasal magnetic induction device 420 comprises a figure-eight-shaped wire coil 430, which may, for example, enhance focusing of the induced field. Alternatively, nasal magnetic induction device 420 comprises a 4-leaf-shaped wire coil, such as described in the above-cited article to Roth B J et al.

Figure 8A:
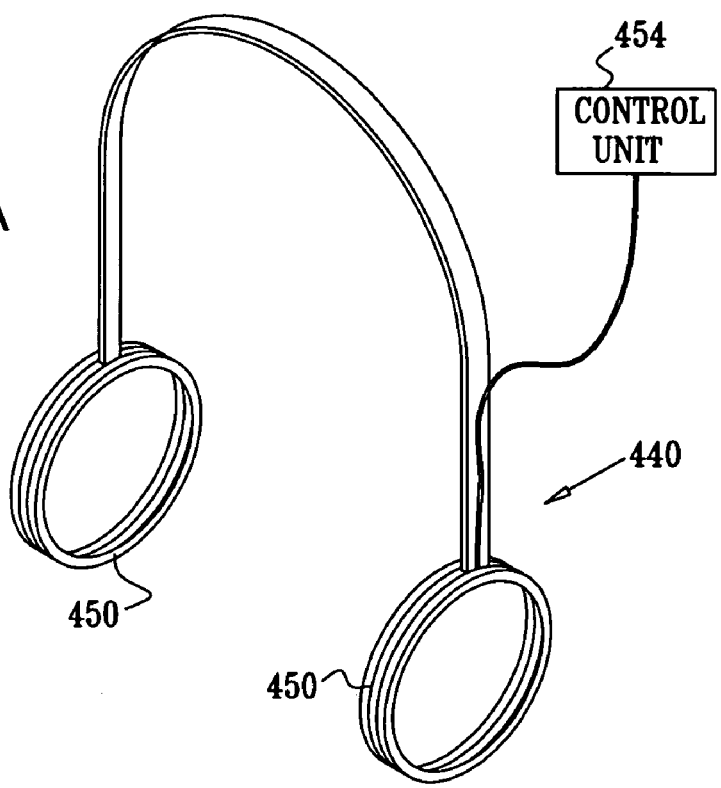
FIGS. 8A and 8B are schematic illustrations of an external magnetic induction device, in accordance with an embodiment of the present invention.
Figure 8B:
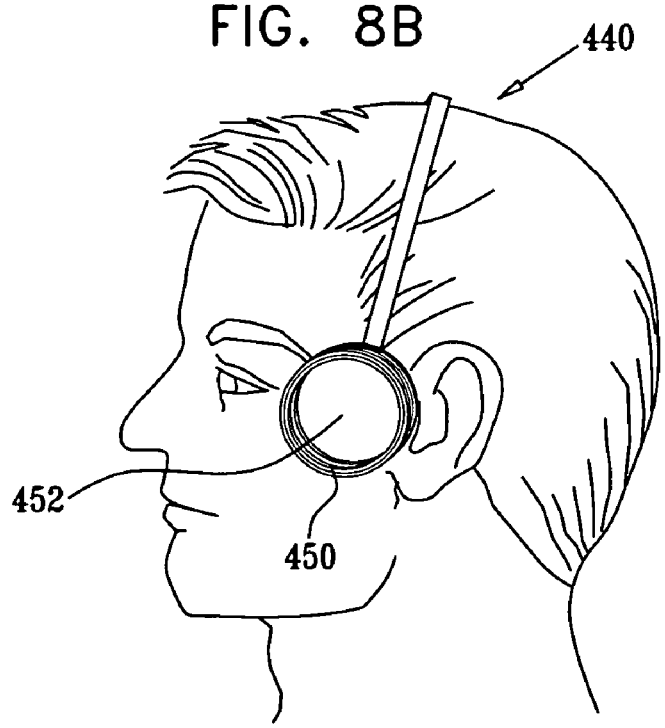

FIGS. 8A and 8B are schematic illustrations of an external magnetic induction device 440, in accordance with an embodiment of the present invention. External magnetic induction device 440 comprises (a) one or more (typically two) magnetic coils 450 adapted to be placed in a vicinity of a temporomandibular joint 452 of a subject, in a vicinity of an MTS, e.g., an SPG, and (b) a control unit 454 coupled to the coils. Typically, each coil 450 has a diameter of between about 30 mm and about 120 mm, and comprises between about 4 and about 30 loops of wire.

In an embodiment of the present invention, an external magnetic induction device comprises a coil adapted to be placed partially or completely around a head of the subject (not necessarily in the configuration shown in FIGS. 8A and 8B), and a control unit coupled to the coil. Typically, the coil has a diameter of between about 3 cm and about 12 cm, and comprises between about 4 and about 30 loops of wire. The coil is configured to focus the generated magnetic field on at least one MTS, e.g., the SPG.

Figure 9:
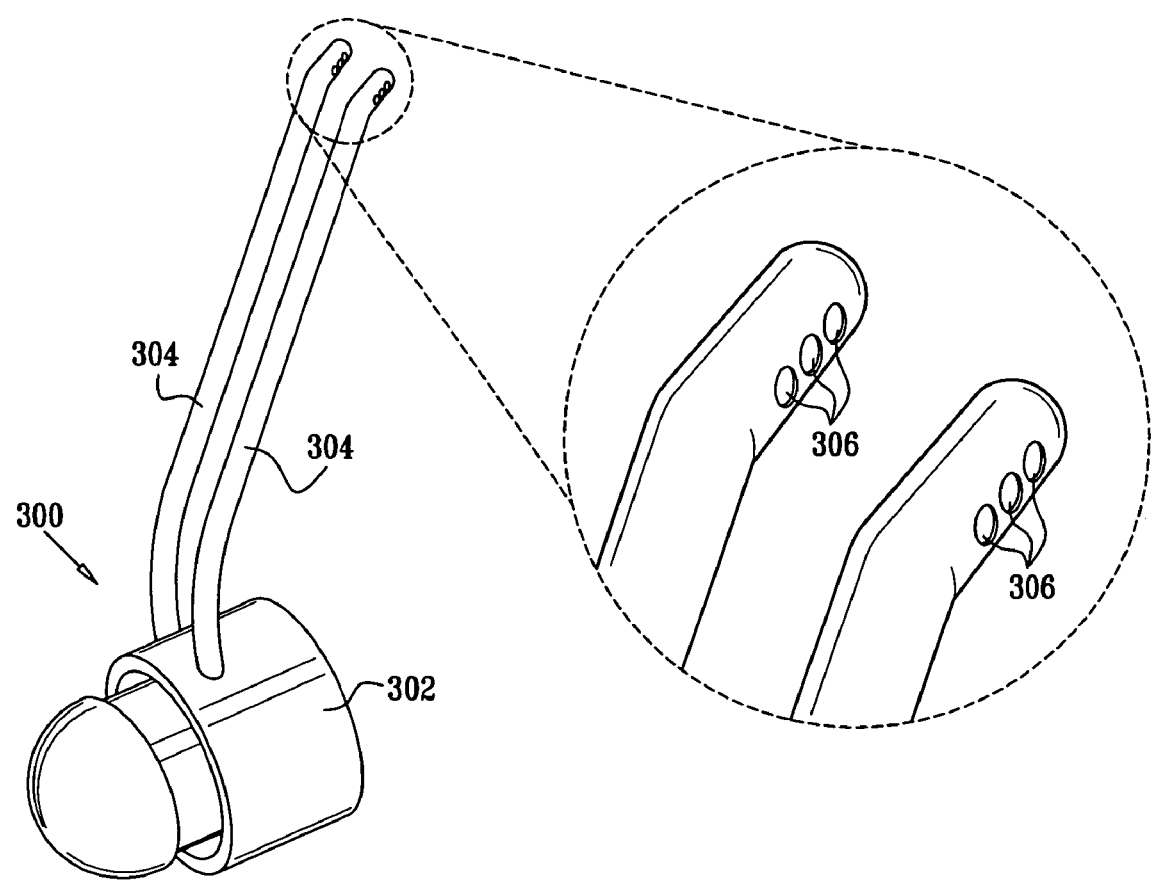
FIG. 9 is a schematic illustration of a nasal applicator, in accordance with an embodiment of the present invention.

FIG. 9 is a schematic illustration of a nasal applicator 300, for use in presenting chemicals to a nasal passage of a subject, in accordance with an embodiment of the present invention. In this embodiment, chemical stimulation of the SPG system (defined hereinabove), and/or of at least one other appropriate MTS, is achieved by presenting chemicals, for example in a liquid or gaseous state, to an air passage of the subject, such as a nasal cavity, a throat, a greater palatine canal, or a sphenopalatine foramen. The temporal profile and other quantitative characteristics of such chemical modulation are believed by the present inventors to have a mechanism of action that has a neuroanatomical basis overlapping with that of the electrical modulation of the MTS. Furthermore, experimental animal evidence collected by the inventors and described in U.S. Provisional Patent Application 60/368,657 to Shalev and Gross entitled, "SPG stimulation," filed Mar. 28, 2002, which is assigned to the assignee of the present invention and is incorporated herein by reference, suggest a correlation between the mechanisms of increasing CBF and increased cerebrovascular permeability. For some applications, chemical-presentation techniques described herein are practiced in combination with techniques described in U.S. Provisional Patent Application 60/376,048, filed Apr. 25, 2002, entitled, "Methods and apparatus for modifying properties of the BBB and cerebral circulation by using the neuroexcitatory and/or neuroinhibitory effects of odorants on nerves in the head," which is assigned to the assignee of the present patent application and is incorporated herein by reference.

Chemicals that may increase or decrease CBF and/or the permeability of the blood-brain barrier (BBB), include, but are not limited to, propionic acid, cyclohexanone, amyl acetate, acetic acid, citric acid, carbon dioxide, sodium chloride, ammonia, menthol, alcohol, nicotine, piperine, gingerol, zingerone, allyl isothiocyanate, cinnamaldehyde, cuminaldehyde, 2-propenyl/2-phenylethyl isothiocyanate, thymol, and eucalyptol. The chemicals reach the appropriate neural structures, excite (or inhibit) the structures, and consequently induce vasodilatation (or vasoconstriction) and/or cerebrovascular permeability changes.

Reference is again made to FIG. 9. In this illustrated embodiment, chemicals are stored in a storage vessel 302, and are delivered to the nasal passage using one or two typically elongated delivery elements 304, which are adapted to reach an upper region of the nasal cavity of the subject, such as in a vicinity of the sphenopalatine foramen or slightly past the sphenopalatine foramen. A distal end of each delivery element 304 is shaped so as to define one or more openings 306, through which the chemicals are released, either omnidirectionally, or in a directed fashion, such as in the direction of the SPG. (The particular configuration of openings 306 on delivery elements 304 is shown by way of illustration and not limitation; other configurations are also suitable.) As appropriate to the particular application, the chemicals may be delivered, for example, in a gaseous state, in a fine spray (e.g., an aerosol spray), or embedded in a viscous or non-viscous liquid matrix. Delivery of the chemicals to the upper region of the nasal cavity, which is in the vicinity of the SPG, typically facilitates the direct diffusion of the chemicals to the SPG.

Alternatively, for some applications, chemicals are presented to the nasal passage or throat using apparatus known in the art, such as an aqueous spray nasal inhaler, a metered dose nasal inhaler, or an air-dilution olfactometer. Further alternatively, nasal delivery devices are used that are described in: (a) a PCT patent application to Shalev, entitled, "Methods and apparatus for modifying properties of the BBB and cerebral circulation by using the neuroexcitatory and/or neuroinhibitory effects of odorants on nerves in the head," filed Apr. 25, 2003, which is assigned to the assignee of the present patent application and incorporated herein by reference, (b) the above-referenced U.S. Provisional Patent Application 60/376,048, (c) one or more of the above-referenced PCT Publications WO 03/084591, WO 03/020350, WO 03/000310, WO 02/068031, and WO 02/068029 to Djupesland, (d) the above-referenced U.S. Patent Application Publication 2003/0079742 to Giroux, and/or (e) the above-referenced patents and patent applications to Levin. Still further alternatively, chemical stimulation is applied to the SPG system, and/or to at least one other appropriate MTS using a transpalatine applicator inserted via the greater palatine canal (configuration not shown).

In an embodiment of the present invention, stimulation of the MTS is achieved by applying a neuroexcitatory agent to the MTS. Suitable neuroexcitatory agents include, but are not limited to acetylcholine and urocholine. For some applications, the MTS is stimulated by applying a neuroinhibitory agent, such as atropine, hexamethonium, or a local anesthetic (e.g., lidocaine).

In an embodiment of the present invention, stimulation of an MTS is achieved by applying mechanical stimulation to the MTS, e.g., vibration.

In an embodiment of the present invention, an acute and/or emergency medical condition of a subject is treated by stimulating at least one MTS by applying electrical, magnetic, electromagnetic, chemical, and/or mechanical stimulation to the site. Such treatment is typically applied as soon as possible after diagnosis of the condition, such as in an emergency room or at the location of the subject. Such stimulation is typically applied using:

one or more of the stimulation devices and/or methods described hereinabove;

techniques described in U.S. patent application Ser. No. 10/258,714, filed Oct. 25, 2002, entitled, "Method and apparatus for stimulating the sphenopalatine ganglion to modify properties of the BBB and cerebral blood flow," or the above-referenced PCT Patent Publication WO 01/85094, which are assigned to the assignee of the present application and are incorporated herein by reference;

techniques described in U.S. Provisional Patent Application 60/426,180, filed Nov. 14, 2002, entitled, "Surgical tools and techniques for stimulation," which is assigned to the assignee of the present application and is incorporated herein by reference;

techniques described in U.S. Provisional Patent Application 60/426,182, filed Nov. 14, 2002, entitled, "Stimulation circuitry and control of electronic medical device," which is assigned to the assignee of the present application and is incorporated herein by reference; and/or techniques known in the art.

In an embodiment of the present invention, an acute brain injury of a subject is treated by applying electrical, magnetic, electromagnetic, chemical, and/or mechanical stimulation to at least one MTS, and configuring the stimulation so as to increase CBF. Such increased CBF increases blood flow to affected brain tissue, which generally causes increased survival of neurons, and thus decreased damage from the injury. Such acute brain injuries include, but are not limited to, ischemic stroke, vasospasm following subarachnoid hemorrhage (SAH), traumatic brain injury (TBI), and seizure.

In an embodiment of the present invention, occlusion within the retinal circulation of a subject is treated by applying electrical, magnetic, electromagnetic, chemical, and/or mechanical stimulation to at least one MTS, and configuring the stimulation so as to induce vasodilation and/or increase retinal blood flow, and thereby treat the condition. For some conditions, increased retinal blood flow releases a block that caused the occlusion. Occlusions of the retinal circulation include retinal artery occlusion (RAO) and retinal venous occlusion (RVO). Optionally, stimulation techniques are used that are described in U.S. patent application Ser. No. 10/294,310 to Gross et al., which is assigned to the assignee of the present application and is incorporated herein by reference, such as techniques described with respect to FIG. 14 thereof.

In an embodiment of the present invention, a complication of SAH of a subject is treated by applying electrical, magnetic, electromagnetic, chemical, and/or mechanical stimulation to at least one MTS, and configuring the stimulation so as to dilate cerebral vessels of the subject. The currently-preferred conventional treatment for SAH includes a surgical procedure in which a medical vehicle is used to treat the SAH. The medical vehicle may comprise, for example: (a) a tool for treating the SAH such as by clipping the aneurysm that caused the SAH, and/or (b) a pharmaceutical treatment. However, the presence of blood in the subarachnoid space sometimes causes increased sensitization of large cerebral arteries, resulting at a later time in cerebral vasospasms. These late-onset vasospasms, in turn, cause brain ischemia and often irreversible damage (see the above-referenced article by Van Gijn J et al.). Therefore, the stimulation of the MTS of this embodiment of the present invention is typically applied in conjunction with such a treatment (e.g., before, during or after the treatment), typically to the SPG, in order to counteract the reduced CBF sometimes caused by blood passage into the subarachnoid space. For some applications, the stimulation of the MTS is initiated at a time after the treatment when the hemorrhage has already been substantially reduced (at which time, in the absence of MTS stimulation, CBF is frequently reduced below desired levels). Alternatively, the stimulation of the MTS is initiated prior to this point, but generally has its strongest elevating effect on CBF once the hemorrhage has been substantially reduced. In either case, the MTS is typically configured to generally improve the temporal profile of the cerebral blood flow.

Alternatively or additionally, the MTS stimulation is performed in conjunction with treatments for other medical conditions typically associated with a decrease in CBF, in order to minimize, eliminate, or even reverse the decrease. Such other treatments conditions include stroke and depression (it is believed by some researchers that some occurrences of depression are related to reduced CBF).

The passage of certain molecules from cerebral blood vessels into the brain is hindered by the BBB. The endothelium of the capillaries, the plasma membrane of the blood vessels, and the foot processes of the astrocytes all impede uptake by the brain of the molecules. The BBB generally allows only small molecules (e.g., hydrophilic molecules of molecular weight less than about 200 Da, and lipophilic molecules of less than about 500 Da) to pass from the circulation into the brain.

In an embodiment of the present invention, the short-term MTS stimulation techniques described herein are used in order to facilitate a diagnosis of a condition of the CNS. For some applications, stimulation of the MTS enhances delivery of diagnostic molecules across the BBB by modulation of at least one MTS and/or another parasympathetic center. These techniques typically stimulate the nerve fibers of the MTS, thereby inducing the middle and anterior cerebral arteries to dilate, and also result in increased CNS bioavailability of various compounds. In this manner, the movement of large diagnostic molecules from within blood vessels to the CNS parenchyma is substantially increased.

For other applications, short-term stimulation of the MTS enhances clearance of at least one constituent of the CNS, such as a protein, from the CNS, across the BBB, and into the systemic blood circulation of the subject. Once the constituent is in the blood circulation, a conventional blood assay is performed in order to detect the constituent. In the absence of the increased permeability of the BBB caused by the stimulation techniques described herein, these constituents do not generally cross the BBB to the blood circulation in quantities sufficient for accurate detection and diagnosis. The presence of specific proteins in unusually large quantities in the CNS is often an indication of a disorder of the CNS, such as Alzheimer's disease.

For some applications, the diagnostic techniques described herein are practiced in combination with the techniques described in (a) the above-referenced U.S. provisional patent application, filed Sep. 26, 2003, entitled, "Diagnostic applications of stimulation," and/or (b) U.S. Provisional Application 60/388,931, filed Jun. 14, 2002, entitled, "Methods and systems for management of Alzheimer's disease." Both of these applications are assigned to the assignee of the present application and are incorporated herein by reference.

In an embodiment of the present invention, the short-term MTS stimulation techniques described herein are used in order to facilitate delivery of a drug to the CNS. For some applications, stimulation of the MTS enhances delivery of therapeutic molecules across the BBB by modulation of at least one MTS and/or another parasympathetic center. These techniques typically excite the nerve fibers of the MTS, thereby inducing the middle and anterior cerebral arteries to dilate, and also causing the walls of these cerebral arteries to become more permeable to large molecules. In this manner, the movement of large therapeutic molecules from within blood vessels to tissue of the CNS is substantially increased. For some applications, these techniques are used to facilitate delivery of a drug that is infrequently administered, such as because of peripheral toxicity (e.g., Carmustine (BCNU) is typically administered once every few months).

It is hypothesized that at least two neurotransmitters play an important role in the change in properties of the BBB—vasoactive intestinal polypeptide (VIP) and nitric oxide (NO). (Acetylcholine may also be involved.) VIP is a short peptide, and NO is a gaseous molecule. VIP is believed to be a major factor in facilitating plasma protein extravasation (PPE), while NO is also considered to be related to vasodilation. For some applications, the parameters of electrical or magnetic stimulation applied to an MTS are varied, as appropriate, in order to selectively influence the activity of one or both of these neurotransmitters. For example, stimulation of the parasympathetic nerve at different frequencies can induce differential secretion—low frequencies cause secretion of NO, while high frequencies (e.g., above about 10 Hz) cause secretion of peptides (VIP).

For other applications of electrical stimulation (in this case, inhibition), a constant level DC signal, or a slowly varying voltage ramp is applied, in order to block parasympathetic neural activity in affected tissue. Alternatively, similar results can be obtained by electrically stimulating at a rate higher than about 10 Hz, because this tends to exhaust neurotransmitters. Thus, the stimulation may be configured to induce parasympathetic electrical block, in order to cause vasoconstriction by mimicking the overall effect of chemical block on the MTS. Conditions treatable in this manner include headaches, e.g., cluster headaches or migraine headaches, and multiple sclerosis.

In an embodiment of the present invention, acute conditions are treated by applying bipolar stimulation, in which a first electrode is applied to a first MTS, and a second electrode is applied to a second MTS.

In an embodiment of the present invention, a medical condition of a subject, such as an acute and/or emergency condition, is treated by electrically stimulating at least one MTS using one or more of the following stimulation parameters:

The total duration of stimulation is between about 0.25 and about 4 hours, such as about 3 hours.

Stimulation is applied with a duty cycle (intermittency) of about 5 minutes "active stimulation," and about 10 minutes "withholding from stimulation." (The active stimulation period is typically between about 2 and about 10 minutes, while the withholding from stimulation period is typically between about 5 and about 15 minutes.)

During the active stimulation period, stimulation is applied for an "on" period of about 90 seconds of each successive about 150-second period within the active stimulation period, and, thereafter, not applied during an "off" period, for about 60 seconds of the 150-second period. (Alternatively, instead of a 150-second period, the period may be between about 50 and 150 seconds, with the stimulation being applied for between about 30% and about 70% thereof.)

During the "on" periods, stimulation is applied as repeated DC pulses having a pulse width of about 1 ms, each typically followed by a duration of sufficient length to enable repolarization of nerve tissue of the MTS, e.g., about 99 ms. These example values represent an effective 10 Hz signal. Other suitable values range from about 2 Hz to about 50 Hz.

Each DC pulse typically has a magnitude less than about 8 V, such as between about 1 and about 7 V, for example, about 3.5 V. The current of the pulse is between about 0.2 and about 10 mA, such as between about 0.5 and about 5 mA, for example, between about 1 and about 2 mA.

In an embodiment of the present invention, an SPG of the subject is indirectly activated by stimulating a branch of cranial nerve V of the subject, including, for example, afferent fibers of the cranial nerve V, either electrically, magnetically, or electromagnetically. A reflex response to such stimulation leads to activation of the SPG. Such stimulation increases permeability of the BBB, and/or increases CBF. Typically, the stimulation is performed while the subject is under general anesthesia or sedation. For some applications, cranial nerve V is stimulated by non-invasively attaching electrodes to the surface of the face of the subject, typically using techniques commonly used for transcutaneous electrical nerve stimulation (TENS).

Figure 10:
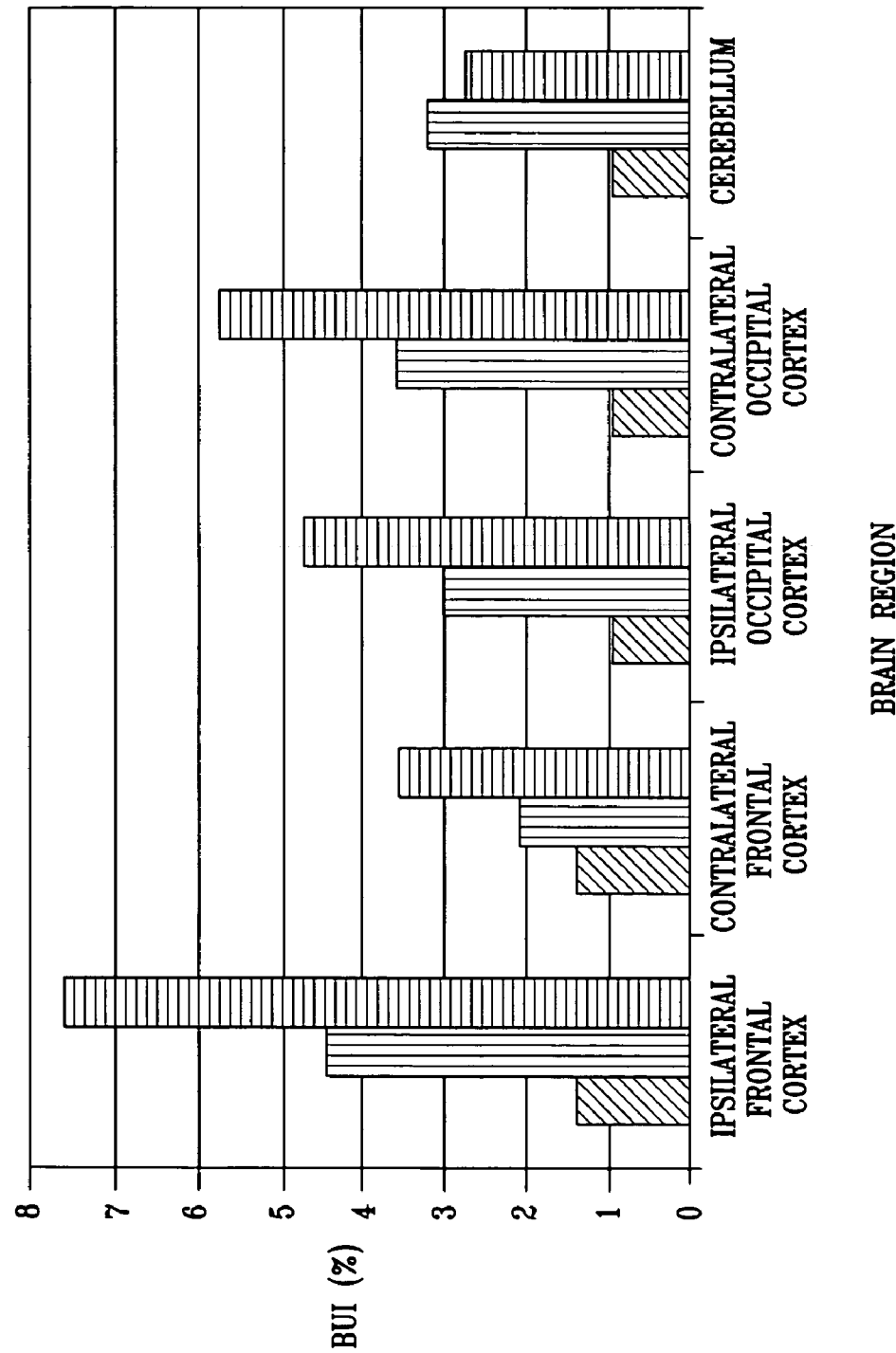
FIG. 10 is a graph showing in vivo experimental results, measured in accordance with an embodiment of the present invention.

Reference is now made to FIG. 10, which is a graph showing in vivo experimental results, measured in accordance with an embodiment of the present invention. Two pigs were anesthetized using 1 g pentobarbital, and anesthesia was maintained using inhaled isoflurane under spontaneous breathing. The oral mucosa in the greater palatine canal was exposed, and a bipolar concentric electrode was inserted into the canal and connected to a controller. The SPG was stimulated for two hours using the following signal parameters: a 90 second/60 second on/off pattern, 10 Hz, 1 ms pulse width, and varying voltage up to 8 V. During the first hour of stimulation, 400 mg of the fluorescent fluid-phase marker fluorescein isothiocyanate-labeled 40 kDa dextran (FITC dextran) was administered in 500 ml normal saline solution. A third pig, in which an electrode was not implanted, served as a control and also received 400 mg FITC dextran. The pigs were sacrificed an hour after the end of the stimulation. No perfusion was performed.

FIG. 10 shows the brain uptake index (BUI) of the FITC dextran conjugate in several locations of the brain of each of the three pigs. BUI is the ratio of the brain tissue concentration of the FITC dextran conjugate to the body weight-normalized dosage (i.e., [brain tissue concentration]/[total dosage/body weight]). As can be seen in the figure, uptake of the FITC dextran conjugate was substantially greater in all of the shown brain regions of both experimental pigs than in the corresponding regions of the control pig. These results demonstrate that SPG stimulation of the experimental pigs substantially increased the BBB permeability of these pigs to the FITC dextran conjugate compared to the BBB permeability of the control pig.

Figure 11:
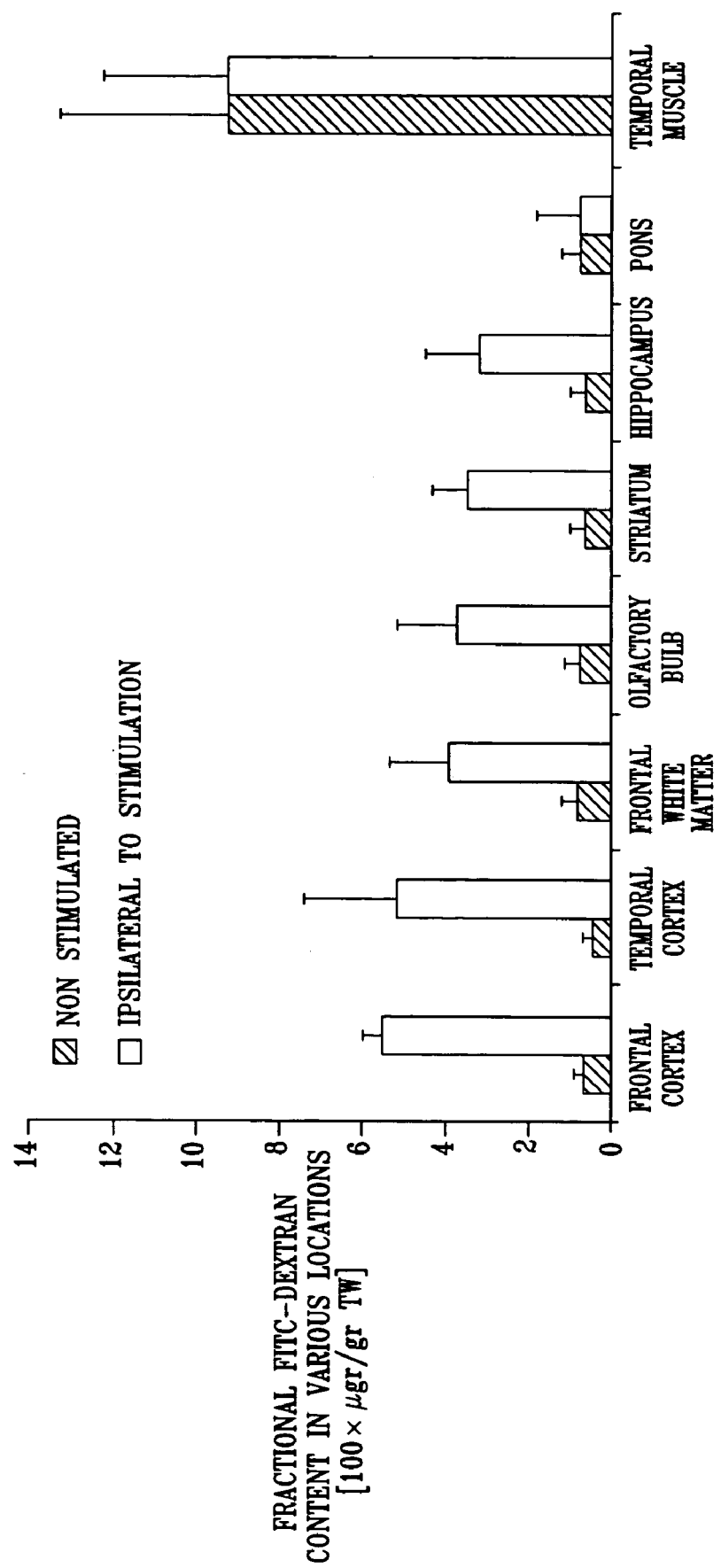
FIG. 11 is another graph showing in vivo experimental results, measured in accordance with an embodiment of the present invention.

Reference is now made to FIG. 11, which is a graph showing in vivo experimental results, measured in accordance with an embodiment of the present invention. Eight beagle dogs (body weight of 10–14 kg) were divided into an experimental group (five dogs) and a control group (three dogs). The dogs were anesthetized with 30 mg/kg pentobarbital. A bipolar concentric stimulating electrode was inserted into the right SPG of each dog, by excising the zygomatic arch and underlying muscles in order to reach the sphenopalatine fossa. Correct placement of the stimulation electrode was confirmed by performing a three-minute stimulation session, after which cholinergic indications (lacrimation and nasal discharge) were used as positive indications of proper electrode placement.

An additional setup procedure was performed to verify that the electrodes were properly positioned to activate SPG cerebrovascular efferents fibers. A 2 ml aliquot of iopamidol was autoinjected (Angiomat 6000, Liebel-Flarsheim Co., Ohio, USA) into the right vertebral artery, after which five consecutive angiographic images of the circle of Willis were taken each 200 ms, using a digital subtraction angiography system (DFA-3-30, Hitachi Medical Co., Tokyo, Japan). Subsequently, 15 seconds of SPG stimulation was performed, having the following signal parameters: 10 Hz, 6 V, pulse width of 1 ms, monophasic, and square wave. Seven seconds after commencement of stimulation, i.e., during the stimulation, the angiographic sequence was repeated. After 5 minutes, another angiographic sequence was performed without SPG stimulation. At each step, dimensions of the middle cerebral artery (MCA) and posterior communicating artery (PCOM) were recorded for later analysis of vasodilatation. This setup procedure confirmed proper electrode placement by observation of nasal discharge and ipsilateral lacrimation.

SPG stimulation was applied to the dogs of the experimental group, using the signal parameters used during the setup procedure. During the first 30 minutes following commencement of SPG stimulation, the dogs of the experimental group were continuously administered 190 mg of 10 kDa FITC dextran, intra-aortically via a transfemoral catheter, using a programmed syringe pump. Angiographic imaging was performed at 5, 15, and 25 minutes following commencement of SPG stimulation, and blood samples were collected at 10, 20, 30, and 40 minutes following commencement of SPG stimulation. The dogs of the control group, while not receiving SPG stimulation, were also administered 190 mg FITC dextran for 20 minutes.

At the conclusion of the experiment, the cephalic circulation of the experimental and control dogs was perfused using heparinized saline, through the aortic catheter, in conjunction with bilateral irrigation through both common carotid arteries. Five minutes following commencement of cephalic perfusion, each dog was sacrificed, and the perfusion was continued for an additional 15 minutes. The brain was removed, and biopsies were taken from the following regions: frontal cortex, temporal cortex, frontal white matter, olfactory bulb, striatum, hippocampus, pons, and the temporal muscle. Each tissue sample was homogenized in heparinized saline. The temporal muscle was also collected to serve as non-cerebral control tissue.

FIG. 11 shows the fractional FITC dextran content in several locations of the brain, ipsilateral to stimulation, in dogs of the experimental and control groups. As can be seen in the graph, the uptake of the FITC dextran conjugate was substantially greater in six of the shown brain regions of the stimulated dogs than in the corresponding regions of the control dogs: the frontal cortex, the temporal cortex, the frontal white matter, the olfactory bulb, the striatum, and the hippocampus. These brain regions are protected by the BBB.

In one control measurement shown in FIG. 11, the FITC dextran content was also measured in the pons, which is protected by the BBB but innervated by the otic ganglion rather than by the SPG. The graph shows that SPG stimulation did not increase uptake of the FITC dextran conjugate in the pons. (The vertical lines extending from the top of the bars represent standard deviation.) In another control measurement shown in FIG. 11, the FITC dextran content was also measured in the temporal muscle, which is not protected by the BBB. The graph shows that uptake in the temporal muscle was high and substantially equivalent with and without SPG stimulation. These results demonstrate that, regardless of the presence or absence of SPG stimulation, tissue that is not protected by the BBB shows a substantial increase in the measured quantity of the FITC dextran conjugate.

In addition, the effect of SPG stimulation on vasodilation of the MCA and PCOM was evaluated. The diameters of these arteries were on average 16.1% greater post-stimulation vs. pre-stimulation (with a standard deviation of 8.2%). These results demonstrate that SPG stimulation substantially increased vasodilation of these arteries.

Figure 12:
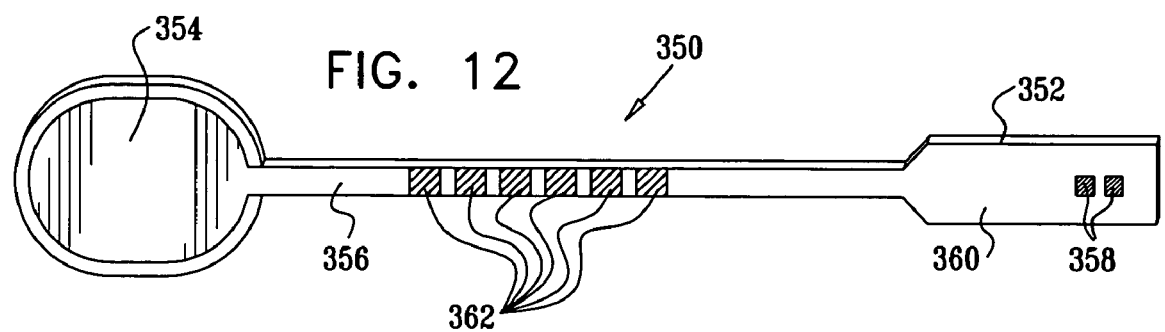
FIG. 12 is a schematic illustration of an implantable neural stimulator, in accordance with an embodiment of the present invention.

FIG. 12 is a schematic illustration of an implantable neural stimulator 350, in accordance with an embodiment of the present invention. Stimulator 350 comprises an electrode support 352, a receiver 354, and a connecting element 356, such as a connecting tube. (Other suitable structures for connecting element 356 will be apparent to one of ordinary skill in the art, having read the disclosure of the present patent application.) Electrode support 352 comprises one or more electrodes 358, positioned on an electrode surface 360 of the support, such that the electrodes are in contact with a target site (e.g., the SPG) when stimulator 350 is implanted. For some applications, electrodes 358 are arranged in the electrode configuration described hereinbelow with reference to FIG. 13. Receiver 354 receives power and control signals from a control unit and utilizes the power and control signals to drive current through electrodes 358. Optionally, connecting element 356 comprises one or more marks 362 that indicate the depth of insertion of stimulator 350 into an implantation site of the subject.

Figure 13:
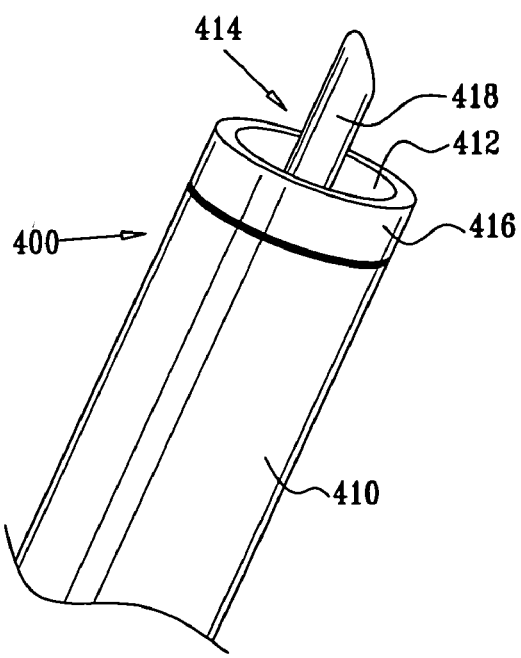
FIG. 13 shows an electrode configuration for use with an electrode support of the stimulator of FIGS. 1A and 1B, or with the stimulator of FIG. 12, in accordance with an embodiment of the present invention.

FIG. 13 shows an electrode configuration for use, for example, with electrical stimulator 4 of FIGS. 1A and 1B, in accordance with an embodiment of the present invention. In this configuration, distal end 9 of support element 8 of electrical stimulator 4 comprises an electrode support 400. Electrode support 400 comprises two insulated regions (i.e., regions having high electrical impedance): an insulated shaft region 410 and an insulated tip region 412. Electrodes 10 of electrical stimulator 4 comprise at least one bipolar electrode 414, comprising an annular electrode 416 and a rod electrode 418, electrically isolated from one another by insulated tip region 412. Alternatively, this configuration is used with stimulator 350 of FIG. 12, in which case electrode support 352 thereof comprises electrode support 400, and electrodes 358 comprise bipolar electrode 414.

Figure 14:
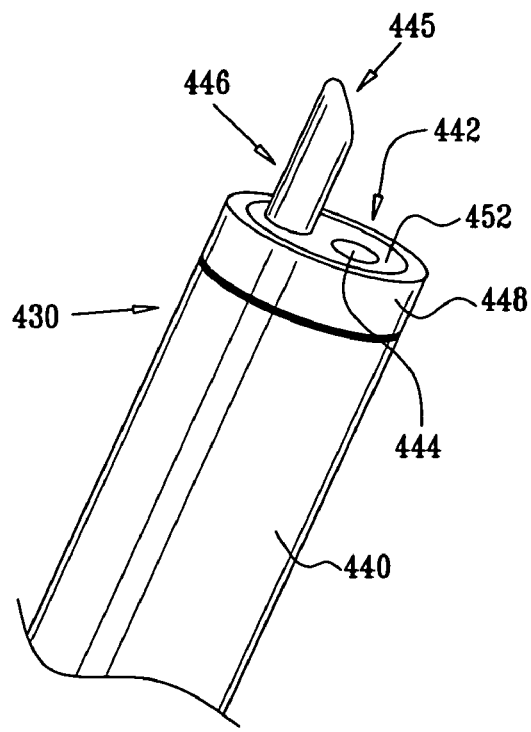
FIG. 14 is a schematic pictorial view of a distal portion of a stimulator for stimulation of a modulation target site, in accordance with an embodiment of the present invention.

FIG. 14 a schematic pictorial view of a distal portion of a stimulator 430, for stimulation of a sphenopalatine ganglion (SPG) system, as defined hereinabove, and/or at least one other appropriate "modulation target site" (MTS), as defined hereinabove, such as an SPG 6 (FIGS. 2A and 2B), in accordance with an embodiment of the present invention. Stimulator 430 comprises a semi-flexible catheter 440. A distal tip 442 of the catheter is shaped so as to define at least one opening 444. Stimulator 430 is adapted to apply a chemical substance through opening 444 to at least a portion of the SPG system, and/or to at least one MTS. Stimulator 430 is typically adapted for insertion via a transpalatine or a nasal approach to a vicinity of the SPG system or MTS.

Chemical substances that may stimulate the SPG system or an MTS include, but are not limited to, propionic acid, cyclohexanone, amyl acetate, acetic acid, citric acid, carbon dioxide, sodium chloride, ammonia, menthol, alcohol, nicotine, piperine, gingerol, zingerone, allyl isothiocyanate, cinnamaldehyde, cuminaldehyde, 2-propenyl/2-phenylethyl isothiocyanate, thymol, eucalyptol, a neuroexcitatory agent, such as acetylcholine or urecholine, and a neuroinhibitory agent, such as atropine, hexamethonium, or a local anesthetic (e.g., lidocaine). Alternatively or additionally, the chemical substance includes one or more substances described in one or more of the above-mentioned patents or patent application publications to Levin.

In an embodiment of the present invention, stimulator 430 additionally comprises at least one electrode 445, such as a bipolar electrode 446. Bipolar electrode 446 may, for example, comprise an annular electrode 448 and a rod electrode 450, electrically isolated from one another by an insulated tip region 452. Alternatively, electrode 445 is monopolar, and a ground, such as a ground patch, is placed elsewhere on or in the subject's body, such as on the face. For some applications, electrode 445 is recessed within catheter 440 or is flush with a surface of the catheter (configurations not shown).

For some applications, electrode 446 is activated in order to confirm accurate placement of distal tip 442 in the vicinity of the desired MTS or SPG system. After distal tip 442 has been inserted and initially positioned, electrode 446 is activated to apply an excitatory signal. Observation of an expected physiological response serves to confirm accurate placement. Typical physiological responses to excitation of an MTS or SPG system include, but are not limited to, increased lacrimation, increased nasal discharge, paresthesia (e.g., of the upper palate), or pain. If necessary, distal tip 442 is repositioned and this placement confirmation technique is repeated. After accurate placement has been confirmed, stimulator 430 applies the chemical substance. This technique for confirming placement may be useful, for example, when the chemical substance includes a neuroinhibitory agent, which would not itself induce the observed physiological response. It should be noted that, for these applications, the applied excitatory electrical signal typically does not provide a direct therapeutic benefit. (For other applications, however, the applied excitatory electrical signal may be applied in order to derive a direct therapeutic benefit.)

Alternatively or additionally, after distal tip 442 is inserted and initially positioned, stimulator 430 applies a neuroexcitatory agent, and observation of an expected physiological response serves to confirm accurate placement. After accurate placement has been confirmed, stimulator 430 applies a neuroinhibitory agent to achieve, for example, a direct therapeutic benefit (e.g., treatment of pain). For this application, a separate lumen and/or opening (not shown) may be used for the neuroexcitatory and neuroinhibitory agents, or a common lumen and/or opening may be used. Alternatively, after accurate placement has been confirmed, stimulator 430 applies an excitatory agent to achieve, for example, a direct therapeutic benefit (e.g., increased BBB permeability or cerebral blood flow).

Alternatively or additionally, after distal tip 442 is inserted and initially positioned, stimulator 430 applies an excitatory electrical signal, and observation of an expected physiological response serves to confirm accurate placement. After accurate placement has been confirmed, stimulator 430 applies an inhibitory electrical signal, and configures to the signal to treat a condition of the subject.

Figure 15:
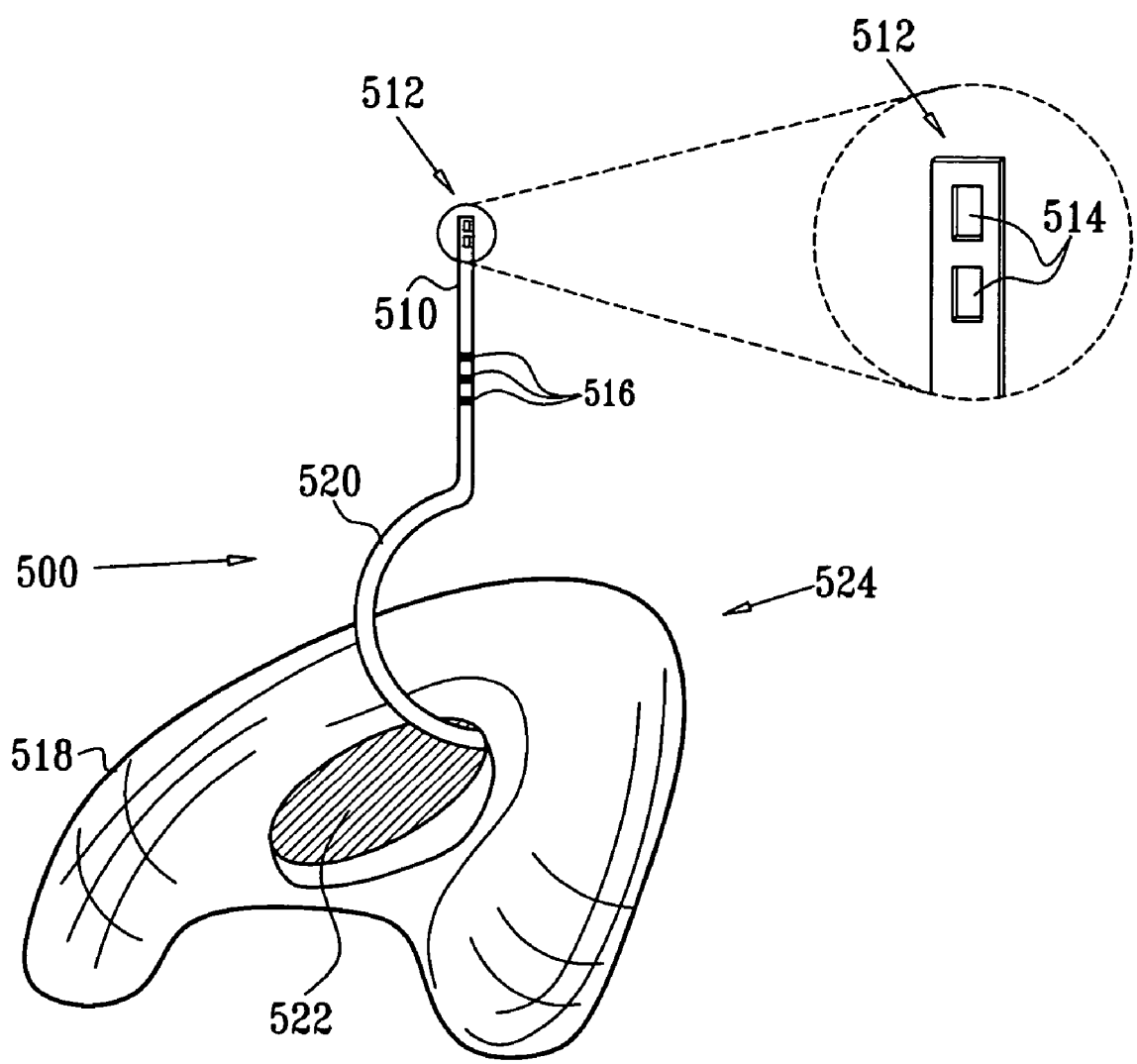
FIG. 15 is a schematic pictorial view of a stimulation syyystem for stimulation of a modulation target site, in accordance with an embodiment of the present invention.
Figure 16A:
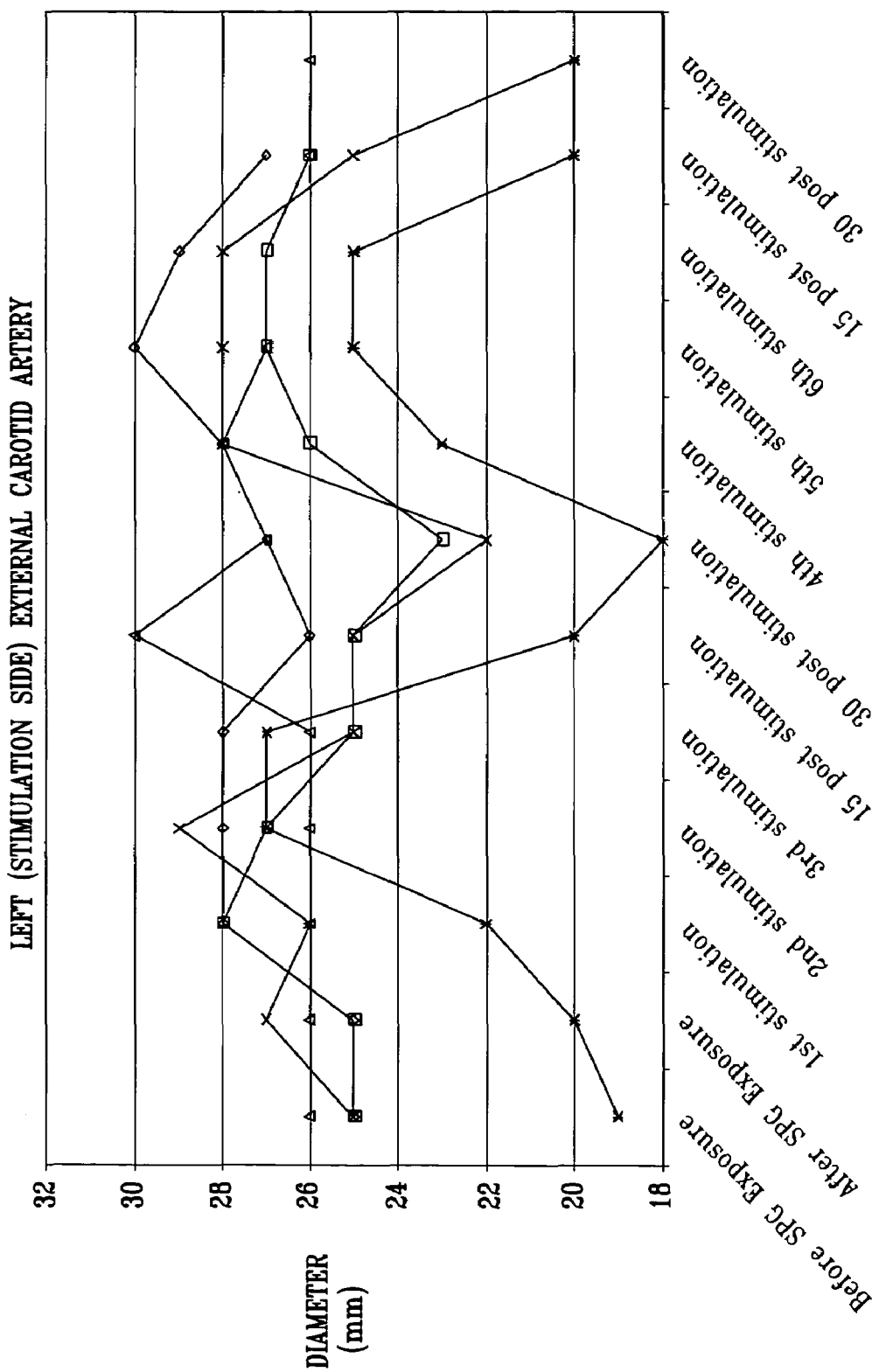
Figure 16B:
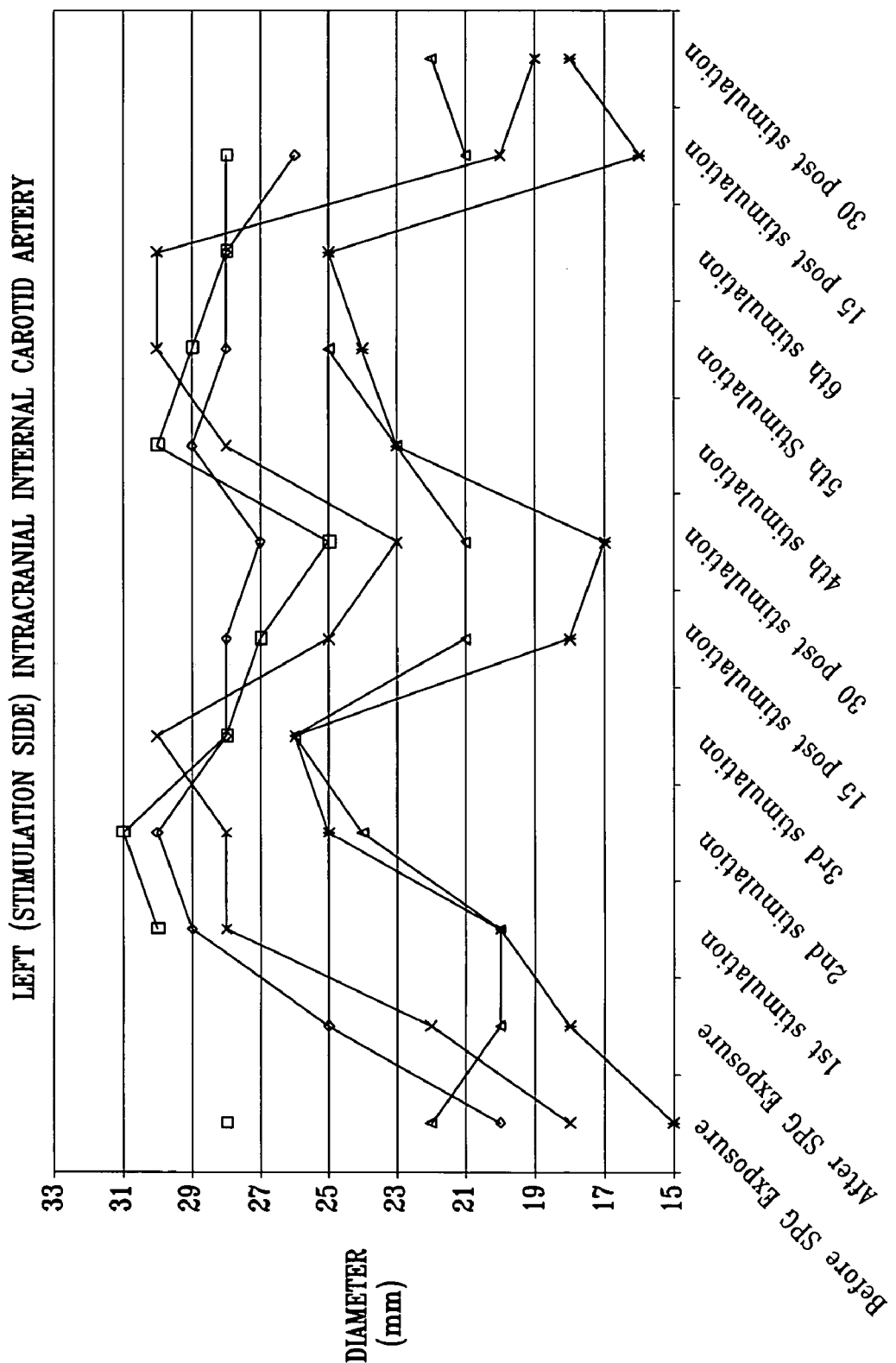
Figure 16C:
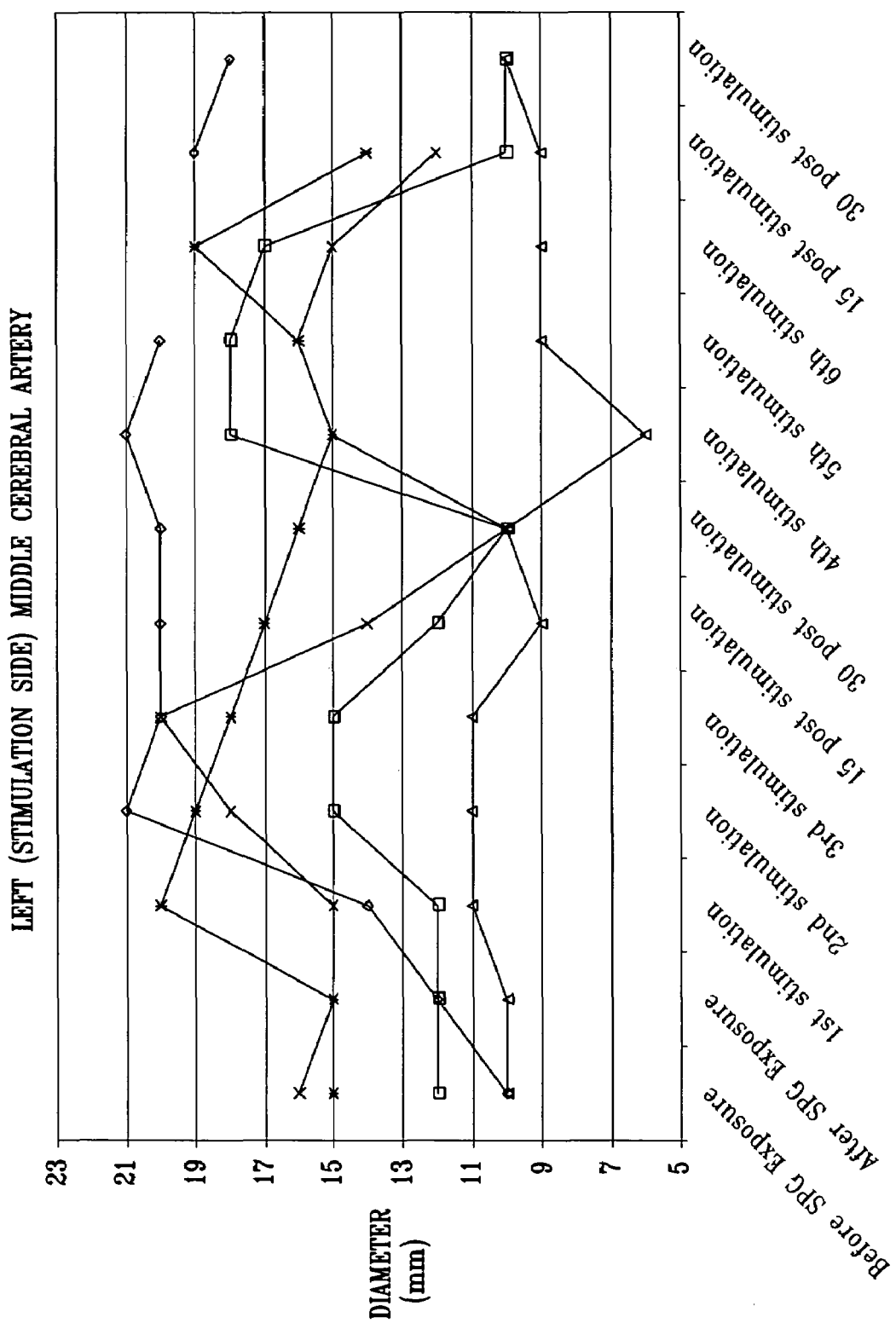
Figure 16D:
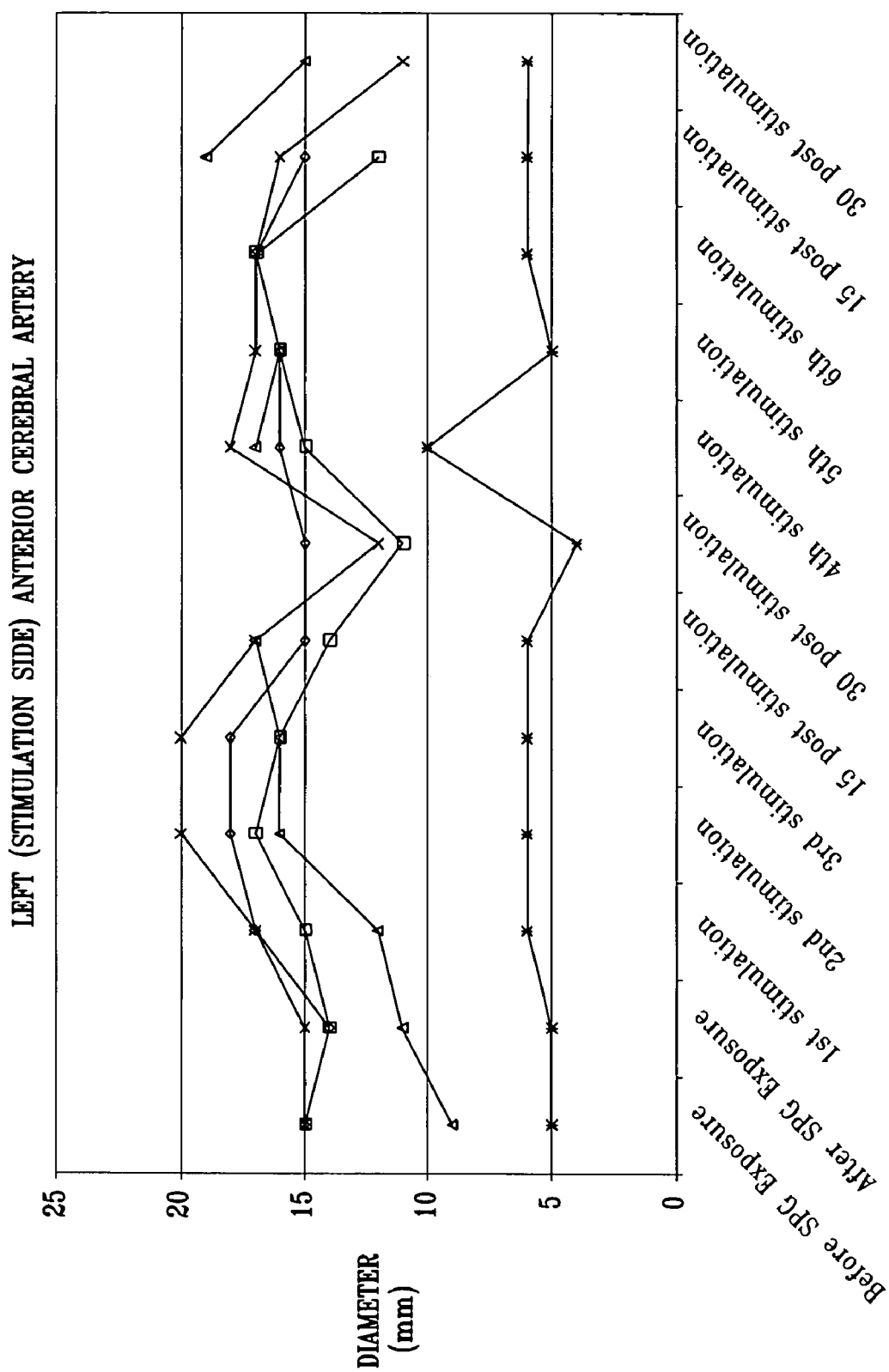
Figure 17A:
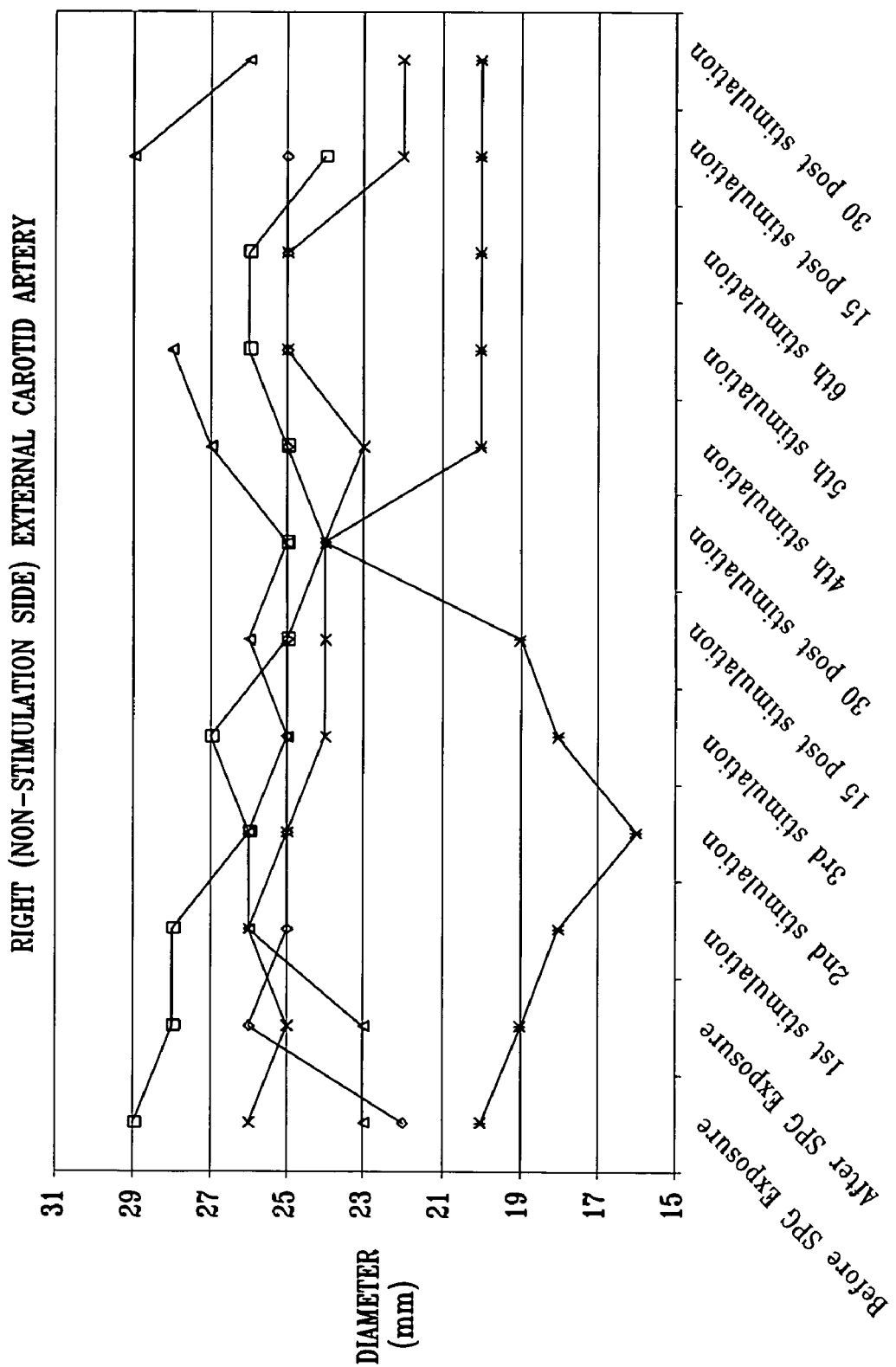
Figure 17B:
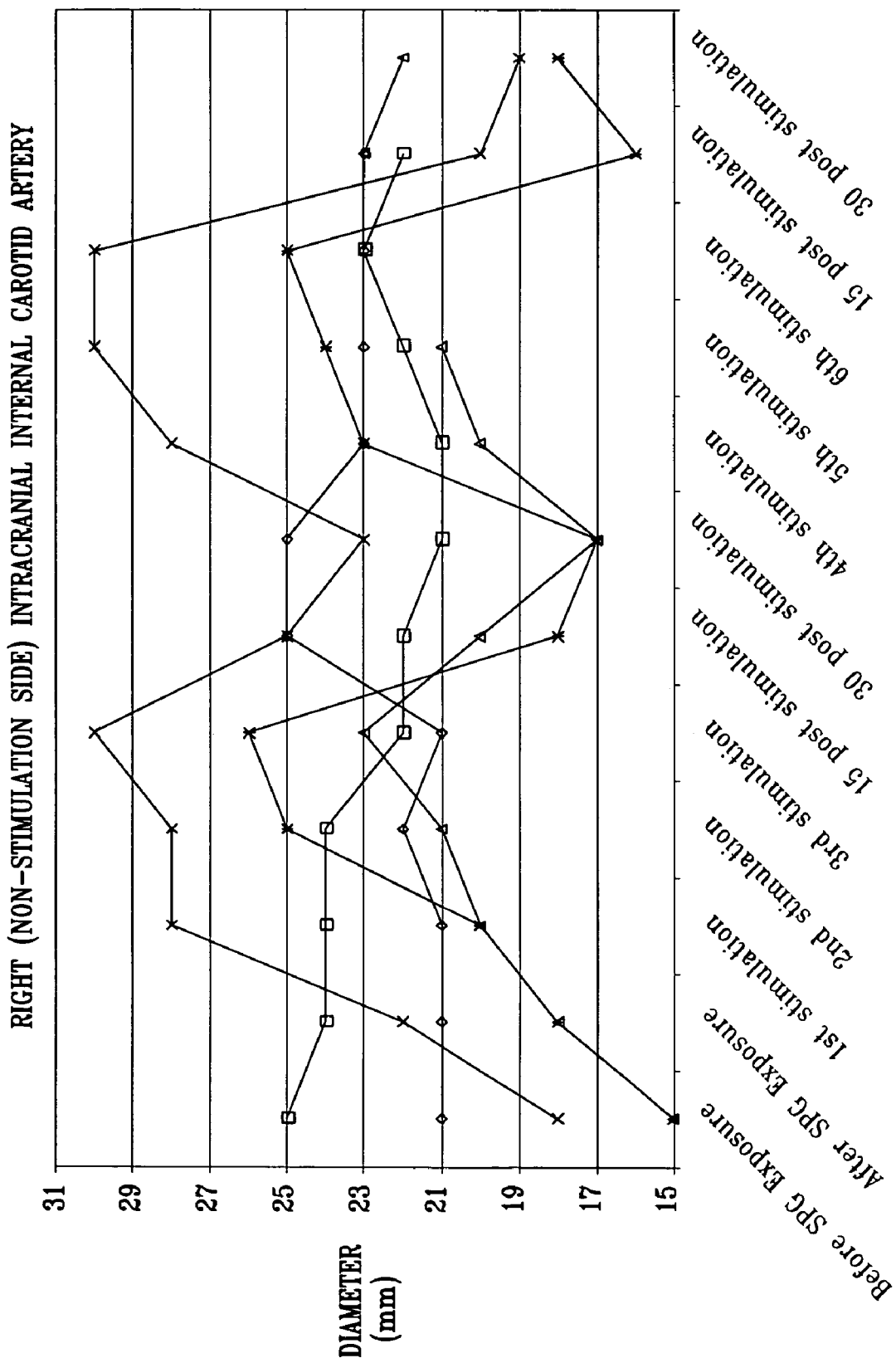
Figure 17D:
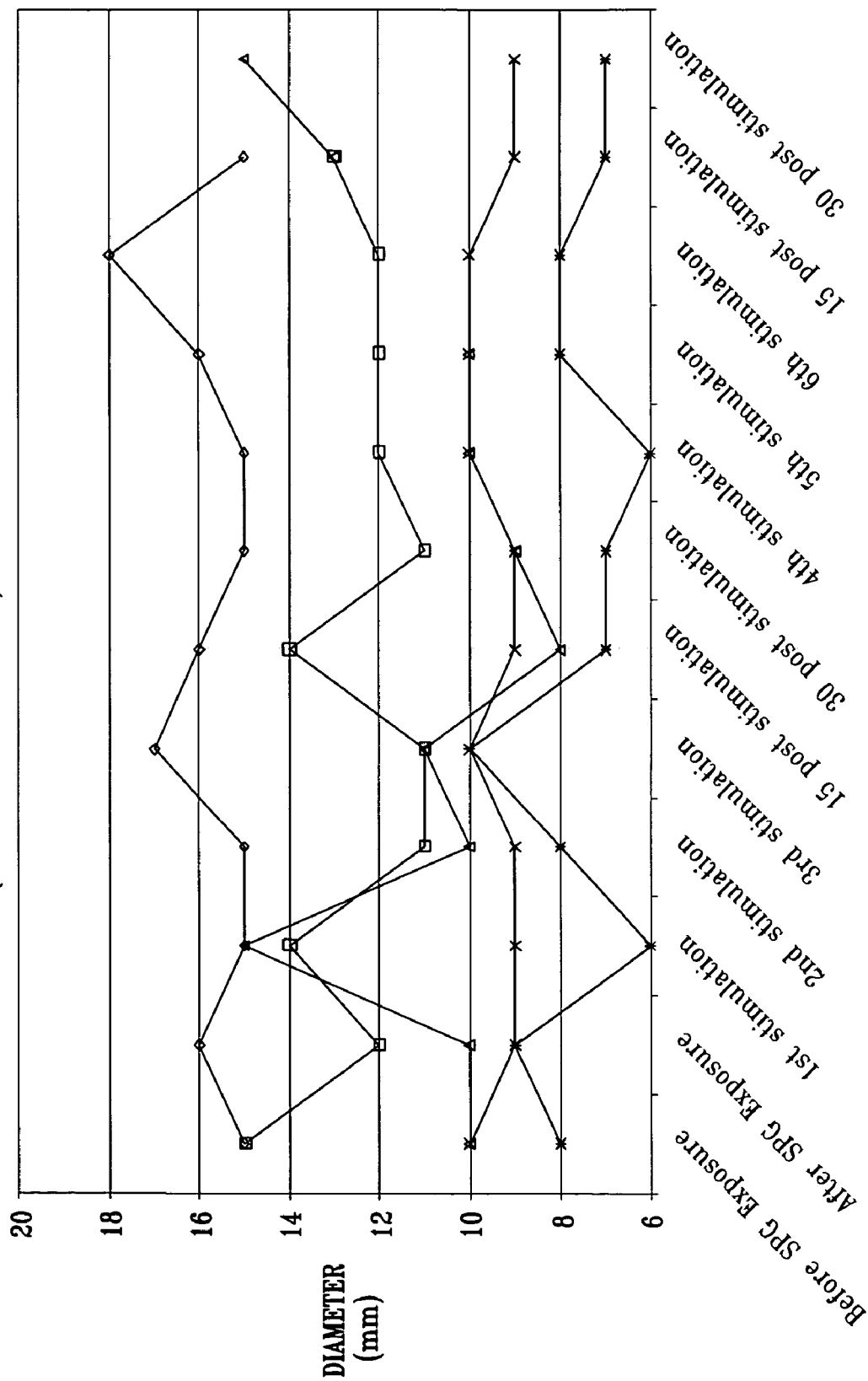
Figure 18A:
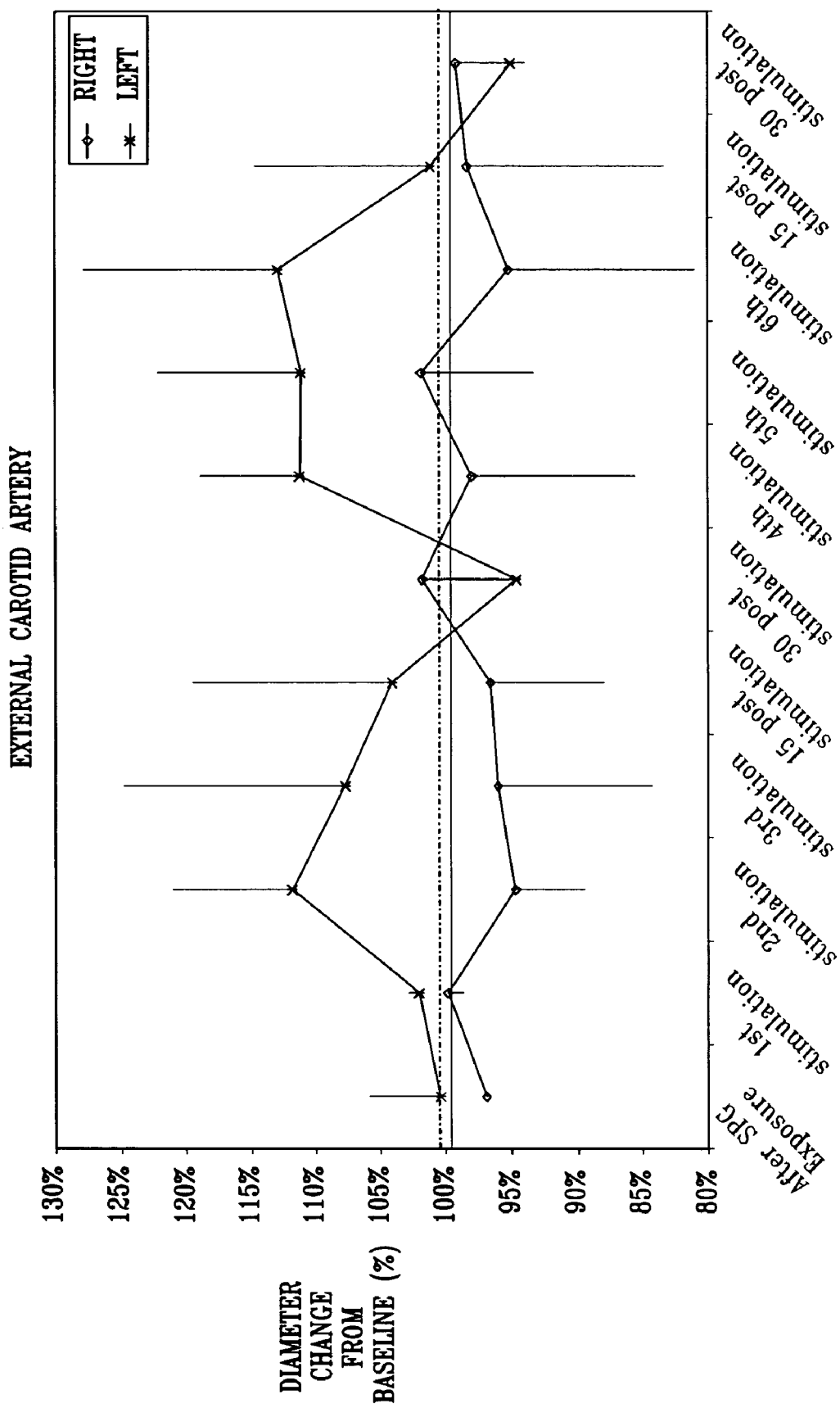
Figure 18B:
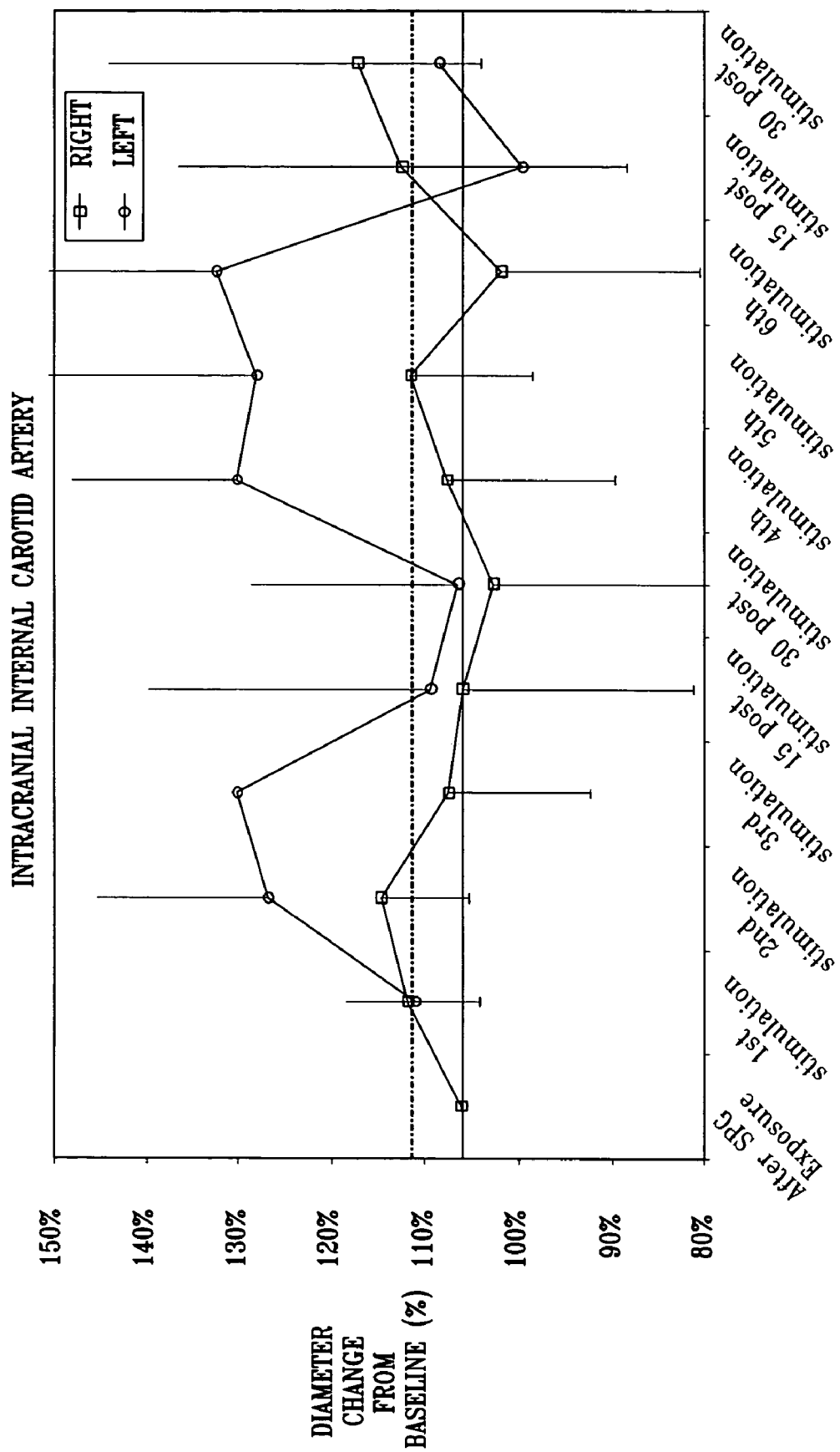
Figure 18C:
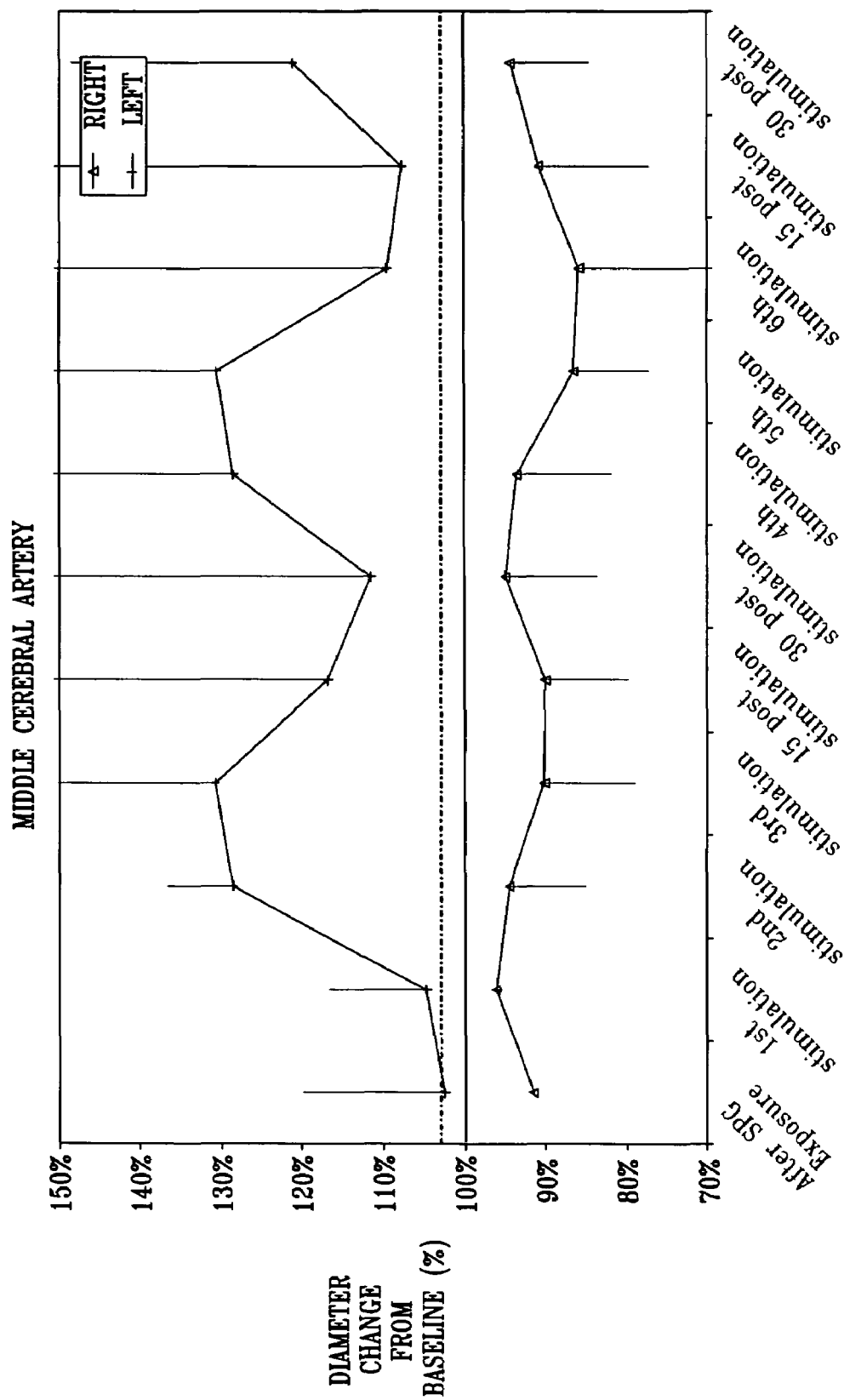
Figure 18D:
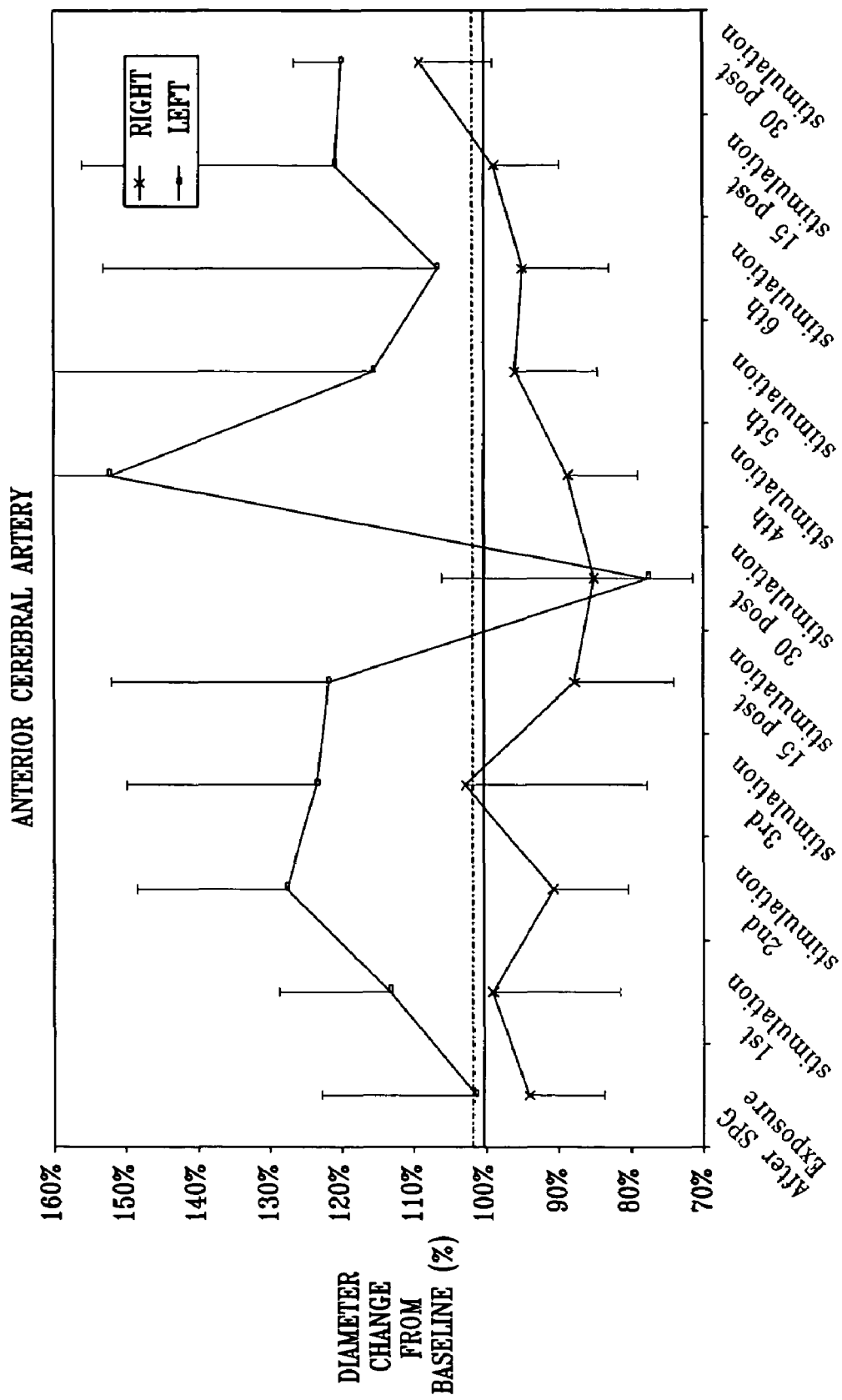

FIG. 15 a schematic pictorial view of a stimulation system 500, for stimulation of a sphenopalatine ganglion (SPG) system, as defined hereinabove, and/or at least one other appropriate "modulation target site" (MTS), as defined hereinabove, such as an SPG 6 (FIGS. 2A and 2B), in accordance with an embodiment of the present invention. Stimulation system 500 comprises a support element 510, which typically, but not necessarily, is generally rigid (i.e., it generally keeps its original shape during a placement procedure). A distal end 512 of support element 510 comprises one or more electrodes 514. For some applications, electrodes 514 are recessed within support element 510, as shown in the figure, while for other applications the electrodes are flush with the surface of the support element, or protrude therefrom. Alternatively, the electrodes are configured as shown in FIGS. 13 and 14.

Support element 510 is adapted to be inserted into a vicinity of an MTS or an SPG system of the subject, via a greater palatine canal in a roof of an oral cavity of the subject. Typically, support element 510 is substantially straight. Support element 510 typically comprises one or more marks 516 that indicate the point at which the support element has been sufficiently inserted into the greater palatine canal. Alternatively or additionally, support element 510 comprises a stopper (not shown) in a vicinity of marks 516, that mechanically prevents further insertion of the support element into the canal.

Stimulation system 500 further comprises a semi-flexible oral appliance 518, which is physically coupled to support element 510 by flexible leads 520. Oral appliance 518 comprises a neurostimulator 522, which is electrically coupled to electrodes 514 via leads 520. An upper surface 524 of oral appliance 518 is shaped to fit closely to the roof of the oral cavity, and is adapted to be coupled thereto. For example, oral appliance 518 may be shaped generally similarly to an orthodontic retainer. Neurostimulator 522 is typically battery-powered, and configurable to drive electrodes 514 to stimulate the MTS or SPG system. For some applications, the subject himself activates neurostimulator 522. Stimulation system 500 is typically adapted to remain in the oral cavity for between several hours and about two days.

In an embodiment of the present invention, a stimulation system for application to a subject comprises an elongated support element having a length of between about 1.8 cm and about 4 cm, such as a length of between about 1.8 cm and about 3 cm. The support element comprises one or more electrodes fixed thereto in a vicinity of a distal end thereof. The stimulation system further comprises a control unit, coupled to the support element in a vicinity of a proximal end thereof. The control unit typically comprises a battery, and is adapted to drive the electrodes to apply an electrical current to tissue of the subject, such as the SPG system and/or at least one MTS. The control unit typically configures the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes. (Together, the on and off periods define a duty cycle.) For example, the control unit may drive the electrodes to apply the current having on periods of between about 60 seconds and about 105 seconds, and off periods of between about 30 seconds and 90 seconds, e.g., on periods of about 90 seconds, and off periods of about 60 seconds.

For some applications, the support element is semi-rigid. For example, the support element and the electrodes together may be similar to conventional concentric needle electrodes, such as Medtronic, Inc. needle electrode model DCN50, or Oxford Instruments Plc. needle electrode models X53153, X53155, X53156, X53158, or X53159.

For some applications, the stimulation system comprises an oral appliance, coupled to the support element, and shaped so as to define a surface that fits closely to a roof of an oral cavity. For example, the oral appliance may be similar to oral appliance 518, described hereinabove with reference to FIG. 15. For some applications, the control unit has a volume, including the battery, of less than about 3 cm³.

In an embodiment of the present invention, a stimulation system for application to a subject comprises an elongated support element having a length of between about 1.8 cm and about 4 cm, such as a length of between about 1.8 cm and about 3 cm. The support element comprises one or more electrodes fixed thereto in a vicinity of a distal end thereof, and a receiver, fixed to the support element in a vicinity of the proximal end thereof. The stimulation system further comprises a control unit, adapted to be coupled to the receiver. The control unit is adapted to drive the electrodes via the receiver to apply an electrical current to tissue of the subject, such as the SPG system and/or at least one MTS. The control unit typically configures the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes. (Together, the on and off periods define a duty cycle.) For example, the control unit may drive the electrodes to apply the current having on periods of between about 60 seconds and about 105 seconds, and off periods of between about 30 seconds and 90 seconds, e.g., on periods of about 90 seconds, and off periods of about 60 seconds.

For some applications, the receiver comprises an electrical contact site, and the control unit is adapted to be coupled to the receiver by being brought into physical contact with the electrical contact site. For example, the control unit may be brought into physical contact by positioning the control unit inside an oral cavity of the subject. For some applications, the stimulation system comprises an oral appliance, adapted to be fixed to the control unit, and shaped so as to define a surface that fits closely to a roof of an oral cavity.

For example, the oral appliance may be similar to oral appliance 518, described hereinabove with reference to FIG. 15.

Alternatively, the receiver comprises a transducer, and the control unit comprises a wireless transmitter, which is adapted to couple the control unit to the receiver via wireless electromagnetic communication with the transducer. Typically, the transducer comprises a coil. For some applications, the control unit is adapted to be positioned outside of a head of the subject. Alternatively, the control unit is adapted to be placed in the oral cavity, such as by being fixed to an oral appliance. For some applications, the receiver has a volume of less than about 0.8 cm$^3$, such as less than about 0.15 cm$^3$.

In an embodiment of the present invention, a stimulation system for application to a subject comprises an ENT endoscope, having at least one working channel, and at least one electrode, adapted to be passed through the working channel, and positioned in a vicinity of tissue of the subject, such as the SPG system and/or at least one MTS. The stimulation system further comprises a control unit, coupled to the electrode, and adapted to drive the electrode to apply a non-ablating electrical signal to the tissue. For some applications, the control unit is adapted to configure the signal to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

For some applications, the ENT endoscope comprises a side-viewing scope having a viewing angle of between about 30 and about 120 degrees relative to a longitudinal axis of the endoscope. Typically, the electrode is adapted to be positioned so as to be viewable by the side-viewing scope.

Reference is now made to FIGS. 16A–D, 17A–D, and 18A–D, which are graphs showing in vivo experimental results, measured in accordance with an embodiment of the present invention. Baseline angiography was performed on six dogs. Subarachnoid hemorrhage (SAH) was simulated in all six dogs by injection of autologous blood into the cisterna magna. Two days later, the subarachnoid blood injection was repeated. Seven days later, angiography was repeated and the left SPG was exposed microsurgically. Angiography was repeated 15 minutes after exposure of the SPG. A bipolar electrode was directly attached to the SPG. The left SPG was then electrically stimulated three times (labeled the first, second, and third stimulations in the figures), and angiography was repeated during each stimulation, 15 minutes after the third stimulation, and 30 minutes after the third stimulation. Forty minutes after cessation of the third stimulation, the left SPG was electrically stimulated three additional times (labeled the fourth, fifth, and sixth stimulations in the figures), and angiography was repeated during each stimulation, 15 minutes after the sixth stimulation, and 30 minutes after the sixth stimulation. All stimulation was performed using the following parameters: 6 V, 10 Hz, and, in alternation, on periods of 90 seconds and off periods of 60 seconds. Adequacy of stimulation was confirmed by the presence of immediate ipsilateral nasal mucous production. Qualitative assessment of the distal intracranial vasculature was also performed.

Comparisons of diameters on day 0, prior to induction of SAH, and on day 7 before SPG exposure (n=4–6 per measurement) showed significant reduction in diameter of the right and left middle cerebral arteries on day 7 compared to day 0 (22±11% and 18±14%, respectively, P<0.05, paired t-tests, all values are given as means±standard deviation). Comparisons before and after SPG exposure on day 7 showed that there were no significant effects of exposure of the SPG on arterial diameters. Sham stimulation produced no substantial changes in arterial diameters compared to the diameters before stimulation and after SPG exposure (n=2 per measure, paired t-tests).

Reference is again made to FIGS. 16A–D, which show the measured diameters of the left (stimulation side) external carotid artery, intracranial internal carotid artery, middle cerebral artery, and anterior cerebral artery, respectively, of five of the dogs at several measurement points in time. (The sixth dog was used for calibration.) These results demonstrate that for the first series of stimulations (first, second, and third stimulations) there were marked increases in the diameters of the intracranial internal carotid, middle cerebral, and anterior cerebral arteries on the stimulation side (left) during stimulation. However, these increases were not statistically significant (ANOVA). For the second series of stimulations (fourth, fifth, and sixth stimulations), there was significant variance in the diameter of the left extracranial and intracranial internal carotid arteries (P<0.05, ANOVA) with pairwise differences between the maximal dilations during stimulation and the value 30 minutes after stimulation.

Reference is again made to FIGS. 17A–D, which show the measured diameters of the right (non-stimulation side) external carotid artery, intracranial internal carotid artery, middle cerebral artery, and anterior cerebral artery, respectively, of five of the dogs at several measurement points in time. As can be seen, stimulation of the left SPG had no substantial effect on the diameters of any of these right cerebral arteries.

In a further analysis of the experimental data, the two series of stimulations were combined (i.e., the first together with the fourth stimulations, the second together with the fifth stimulations, the third together with the sixth stimulations, the 15 minutes after the third stimulation together with the 15 minutes after the sixth stimulation, and the 30 minutes after the third stimulation together with the 30 minutes after the sixth stimulation). The combined data were analyzed over time. There was significant variance in diameters for the left extracranial internal carotid artery (P<0.05, ANOVA) with a significant pairwise difference between the maximal dilation and the diameter 30 minutes after stimulation. This variance was due to dilation, as well as in part to a trend for the diameter to be smaller 30 minutes after stimulation than it was before stimulation. For the left intracranial internal carotid there was significant variance (P<0.001, ANOVA) with pairwise differences between two of the series of stimulations and the diameter before and 30 minutes after stimulation. There were no significant effects of stimulation on the diameters of the left (stimulation side) middle and anterior cerebral arteries, or on any of the right (non-stimulation side) arteries at any time.

Reference is again made to FIGS. 18A–D, which show percentage changes from baseline of the diameters of the left (stimulation side) and right (non-stimulation side) external carotid artery, intracranial internal carotid artery, middle cerebral artery, and anterior cerebral artery, respectively, of five of the dogs in combination, at several measurement points in time. Vertical lines on data points indicate standard deviation. Comparisons were made between the right and left arteries at each time by paired t-tests for each separate series of stimulations and for the combined series of stimulations. At baseline on day 0, prior to induction of SAH, and on day 7 after SPG exposure, there were no significant differences between the right and left arteries. There were significant differences between the right and left arteries during the third, fourth, fifth and sixth stimulations for the intracranial internal carotid artery (P=0.007, 0.039, 0.01, 0.01, respectively), during the fourth stimulation for the anterior cerebral artery (P=0.05), and during the sixth stimulation for the extracranial internal carotid artery (P=0.047).

In a further analysis of the experimental data, the two series of stimulations were combined, as described above. Significant differences were found for: (a) the anterior cerebral artery during the first combined stimulation (P=0.05); (b) the extracranial internal carotid (P=0.005), intracranial internal carotid (P<0.001), and middle cerebral arteries (P=0.043) during the second combined stimulation; and (c) the extra- and intracranial internal carotid during the third combined stimulation (P=0.009 and <0.001, respectively). Finally, qualitative comparison of the distal vasculature showed marked dilation of the distal vasculature in response to stimulation.

Taken as a whole, these experimental data indicate that SPG stimulation, using the techniques described herein, reverses mild to moderate vasospasm after SAH in dogs.

In some embodiments of the present invention, techniques described herein are practiced in combination with techniques described in one or more of the references cited in the Background section hereinabove and/or in combination with techniques described in one or more of the patent applications cited hereinabove.

Techniques described in this application may be practiced in combination with methods and apparatus described in one or more of the following patent applications, which are assigned to the assignee of the present patent application and are incorporated herein by reference:

U.S. patent application Ser. No. 10/258,714, filed Oct. 25, 2002, entitled, "Method and apparatus for stimulating the sphenopalatine ganglion to modify properties of the BBB and cerebral blood flow," or the above-referenced PCT Publication WO 01/85094

U.S. Provisional Patent Application 60/364,451, filed Mar. 15, 2002, entitled, "Applications of stimulating the sphenopalatine ganglion (SPG)"

U.S. Provisional Patent Application 60/368,657, filed Mar. 28, 2002, entitled, "SPG Stimulation"

U.S. Provisional Patent Application 60/376,048, filed Apr. 25, 2002, entitled, "Methods and apparatus for modifying properties of the BBB and cerebral circulation by using the neuroexcitatory and/or neuroinhibitory effects of odorants on nerves in the head"

U.S. Provisional Patent Application 60/388,931, filed Jun. 14, 2002, entitled "Methods and systems for management of Alzheimer's disease"

U.S. Provisional Patent Application 60/400,167, filed Jul. 31, 2002, entitled, "Delivering compounds to the brain by modifying properties of the BBB and cerebral circulation"

U.S. Provisional Patent Application 60/426,180, filed Nov. 14, 2002, entitled, "Surgical tools and techniques for sphenopalatine ganglion stimulation"

U.S. Provisional Patent Application 60/426,182, filed Nov. 14, 2002, and a corresponding PCT application claiming priority therefrom, filed Nov. 13, 2003, entitled, "Stimulation circuitry and control of electronic medical device"

U.S. patent application Ser. No. 10/294,310, filed Nov. 14, 2002, entitled, "SPG stimulation for treating eye pathologies"

U.S. patent application Ser. No. 10/294,343, filed Nov. 14, 2002, and a corresponding PCT application claiming priority therefrom, filed Nov. 13, 2003, entitled, "Administration of anti-inflammatory drugs into the CNS"

U.S. Provisional Patent Application Ser. No. 60/426,181, filed Nov. 14, 2002, entitled, "Stimulation for treating ear pathologies"

U.S. Provisional Patent Application 60/448,807, filed Feb. 20, 2003, entitled, "Stimulation for treating autoimmune-related disorders of the CNS"

U.S. Provisional Patent Application 60/461,232 to Gross et al., filed Apr. 8, 2003, entitled, "Treating abnormal conditions of the mind and body by modifying properties of the blood-brain barrier and cephalic blood flow"

a PCT Patent Application to Shalev, filed Apr. 25, 2003, entitled, "Methods and apparatus for modifying properties of the BBB and cerebral circulation by using the neuroexcitatory and/or neuroinhibitory effects of odorants on nerves in the head"

a U.S. provisional patent application, filed Sep. 26, 2003, entitled, "Diagnostic applications of stimulation"

a U.S. patent application, filed Oct. 2, 2003, entitled, "Targeted release of nitric oxide in the brain circulation for opening the BBB"

a PCT patent application, filed Nov. 13, 2003, entitled, "Stimulation for treating ear pathologies"

a PCT patent application, filed Nov. 13, 2003, entitled, "Surgical tools and techniques for stimulation"

As used in the present application and in the claims, the BBB comprises the tight junctions opposing the passage of most ions and large molecular weight compounds between the blood and brain tissue.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. For example, elements which are shown in a figure to be housed within one integral unit may, for some applications, be disposed in a plurality of distinct units. Similarly, apparatus for communication and power transmission which are shown to be coupled in a wireless fashion may be, alternatively, be coupled in a wired fashion, and apparatus for communication and power transmission which are shown to be coupled in a wired fashion may be, alternatively, be coupled in a wireless fashion.

The invention claimed is:

1. Apparatus for application to a subject, comprising:
an elongated support element having a length of between about 1.8 cm and about 4 cm, and having a proximal end and a distal end;
one or more electrodes fixed to the support element in a vicinity of the distal end thereof;
a receiver, fixed to the support element in a vicinity of the proximal end thereof; and
a control unit, adapted to be coupled to the receiver, and adapted to:
drive the electrodes to apply an electrical current to tissue of the subject, and
configure the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes, wherein the control unit is adapted to be positioned inside an oral cavity of the subject, and comprising an oral appliance, adapted to be fixed to the control unit, and shaped so as to define a surface that fits closely to a roof of the oral cavity.

2. The apparatus according to claim 1, wherein the tissue is selected from the group consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject, and wherein the control unit is adapted to drive the electrodes to apply the current to the selected tissue.

3. The apparatus according to claim 2, wherein the tissue includes the SPG, and wherein the control unit is adapted to drive the electrodes to apply the current to the SPG.

4. The apparatus according to claim 2, wherein the tissue includes the greater palatine nerve, and wherein the control unit is adapted to drive the electrodes to apply the current to the greater palatine nerve.

5. The apparatus according to claim 1, wherein the support element has a length of between about 1.8 cm and about 3 cm.

6. The apparatus according to claim 1, wherein the receiver comprises an electrical contact site, and wherein the control unit is adapted to be coupled to the receiver by being brought into physical contact with the electrical contact site.

7. The apparatus according to claim 1, wherein the receiver comprises a transducer, and wherein the control unit comprises a wireless transmitter, which is adapted to couple the control unit to the receiver via wireless communication with the transducer.

8. The apparatus according to claim 7, wherein the transducer comprises a coil.

9. The apparatus according to claim 7, wherein the wireless transmitter is adapted to wirelessly couple the control unit to the receiver via wireless electromagnetic communication with the transducer.

10. The apparatus according to claim 1, wherein the receiver has a volume of less than about 0.8 cm$^3$.

11. The apparatus according to claim 10, wherein the receiver has a volume of less than about 0.15 cm$^3$.

12. The apparatus according to claim 1, wherein the control unit is adapted to apply the current having on periods of between about 60 seconds and about 105 seconds, and off periods of between about 30 seconds and 90 seconds.

13. The apparatus according to claim 12, wherein the control unit is adapted to apply the current having on periods of about 90 seconds, and off periods of about 60 seconds.

14. The apparatus according to claim 1, wherein at least a portion of the support element is adapted to be placed in a greater palatine canal of the subject.

15. A method comprising:
inserting an elongated support element into a body of a subject, the element having a length of between about 1.8 cm and about 4 cm, and having a distal end;
applying, from a vicinity of the distal end, an electrical current to tissue of the subject; and
configuring the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

16. The method according to claim 15, wherein applying the current comprises receiving energy at the support element, and, using the energy, applying the current to the tissue.

17. The method according to claim 16, wherein receiving the energy comprises transmitting the energy from inside an oral cavity of the subject, and receiving the transmitted energy.

18. The method according to claim 16, wherein receiving the energy comprises receiving the energy from inside an oral cavity of the subject via an electrical contact site of the support element.

19. The method according to claim 16, wherein receiving the energy comprises wirelessly receiving the energy.

20. The method according to claim 19, wherein wirelessly receiving the energy comprises wirelessly receiving electromagnetic energy.

21. The method according to claim 19, wherein wirelessly receiving the energy comprises wirelessly transmitting the energy from outside of a head of the subject, and wirelessly receiving the transmitted energy.

22. The method according to claim 19, wherein wirelessly receiving the energy comprises wirelessly transmitting the energy from inside an oral cavity of the subject, and wirelessly receiving the transmitted energy.

23. The method according to claim 15, wherein the tissue is selected from the group consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject, and wherein applying the current comprises applying the current to the selected tissue.

24. The method according to claim 23, wherein the tissue includes the SPG, and wherein applying the current comprises applying the current to the SPG.

25. The method according to claim 23, wherein the tissue includes the greater palatine nerve, and wherein applying the current comprises applying the current to the greater palatine nerve.

26. The method according to claim 15, wherein the support element has a length of between about 1.8 cm and about 3 cm, and wherein inserting the support element comprises inserting the support element having the length of between about 1.8 cm and about 3 cm.

27. The method according to claim 15, wherein configuring the current comprises configuring the current to have on periods of between about 60 seconds and about 105 seconds, and off periods of between about 30 seconds and 90 seconds.

28. The method according to claim 27, wherein configuring the current comprises configuring the current to have on periods of about 90 seconds, and off periods of about 60 seconds.

29. The method according to claim 15, wherein inserting the support element comprises inserting at least a portion of the support element into a greater palatine canal of the subject.

30. The method according to claim 29, wherein inserting the at least a portion of the support element into the greater palatine canal comprises inserting the at least a portion of the support element into the greater palatine canal via a roof of an oral cavity of the subject.

* * * * *

UNITED STATES PATENT AND TRADEMARK OFFICE
CERTIFICATE OF CORRECTION

| | |
|---|---|
| PATENT NO. | : 7,117,033 B2 |
| APPLICATION NO. | : 10/783113 |
| DATED | : October 3, 2006 |
| INVENTOR(S) | : Alon Shalev and Amir Natan |

Page 1 of 1

It is certified that error appears in the above-identified patent and that said Letters Patent is hereby corrected as shown below:

On Cover Page, item [57], ABSTRACT, insert --at-- between "at least"

On page 3, OTHER PUBLICATIONS,

U.S. Application No. 10/428,743, filed May 24, 2002 for Treatment of Epilepsy by Brian Stimulation..."Brian" should read --Brain--

Suzuki, N. et al., Selective Stimulation of Postganglionic Cerebrovascular... insert --Electrical-- after "Selective"

Signed and Sealed this

Thirtieth Day of January, 2007

JON W. DUDAS
*Director of the United States Patent and Trademark Office*